(12) United States Patent
Mori et al.

(10) Patent No.: US 7,273,710 B2
(45) Date of Patent: Sep. 25, 2007

(54) METHOD FOR SCREENING MCH RECEPTOR ANTAGONIST/AGONIST

(75) Inventors: Masaaki Mori, Tsukuba (JP); Yukio Shimomura, Tsukuba (JP); Mioko Harada, Tsukuba (JP); Tsukasa Sugo, Tsukuba (JP); Yasushi Shintani, Toyonaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 518 days.

(21) Appl. No.: 10/332,082

(22) PCT Filed: Jul. 4, 2001

(86) PCT No.: PCT/JP01/05809

§ 371 (c)(1),
(2), (4) Date: Jan. 2, 2003

(87) PCT Pub. No.: WO02/03070

PCT Pub. Date: Jan. 10, 2002

(65) Prior Publication Data

US 2004/0086941 A1    May 6, 2004

(30) Foreign Application Priority Data

Jul. 5, 2000 (JP) .............................. 2000-208254

(51) Int. Cl.
*C07K 11/02* (2006.01)
*C07K 14/705* (2006.01)
*G01N 33/566* (2006.01)

(52) U.S. Cl. .................. 435/7.21; 436/501; 530/317; 530/350

(58) Field of Classification Search .................... None
See application file for complete search history.

(56) References Cited

U.S. PATENT DOCUMENTS 6,593,108 B1 * 7/2003 Liu et al. .................... 435/69.1

FOREIGN PATENT DOCUMENTS

| WO | WO99/28492 | 6/1999 |
| WO | WO 00/40725 | 7/2000 |
| WO | WO 00/49046 | 8/2000 |
| WO | WO 01/07606 | 2/2001 |
| WO | WO 01/36479 | 5/2001 |
| WO | WO 01/57070 | 8/2001 |
| WO | WO 01/70975 | 9/2001 |

OTHER PUBLICATIONS

Lembo et al. "The receptor for the orexigenic peptide melanin-concentrating hormone is a G-protein-coupled receptor" Nature Cell Biol 1:267-271 (1999).
Bachner et al. "Identification of melanin concentrating hormone (MCH) as the natural ligand for the orphan somatostatin-like receptor 1 (SLC-1)" FEBS Letters 457:522-524 (1999).
Saito et al. "Molecular Characterization of the melanin-concentrating-hormone receptor" Nature 400: 265-269 (1999).
Chambers et al. "Melanin-concentrating hormone is the cognate ligand for the orphan G-protein-coupled receptor SLC-1" Nature 400: 261-265 (1999).
Shimomura et al. "Isolation and identification of Melanin-concentrating hormone as the endogenous ligand of the SLC-1 receptor" Biochemical and Biophysical Research Commun 261: 622-626 (1999).
MacDonald, D., et al., "Molecular Characterization of the Melanin-Concentrating Hormone/Receptor Complex: Identification of Critical Residues Involved in Binding and Activation", *Molecular Pharmacology*, (2000), vol. 58, No. 1, pp. 217-225.
Hintermann, E., et al., "Synthesis and Receptor Binding Activity of Analogues and Fragments of Human Melanin-Concentrating Hormone (MCH)", *Database CA Online*, Database Accession No. 132:203272, XP002346918, 1997.

* cited by examiner

*Primary Examiner*—John Ulm
(74) *Attorney, Agent, or Firm*—David G. Conlin; Edwards Angell Palmer & Dodge

(57) ABSTRACT

The present invention relates to a screening method for a compound or a salt thereof that alters the binding property of MCH or a salt thereof to SLT or a salt thereof, or a partial peptide thereof, an amide or an ester thereof, or a salt thereof, characterized by using MCH, a derivative or a salt thereof and SLT or a salt thereof, or a partial peptide thereof, an amide or an ester thereof, or a salt thereof. The screening method of the present invention is useful for screening an SLT agonist, which can be used as an agent for promoting appetite (eating), and an SLT antagonist, which can be used as a prophylactic and/or therapeutic agent for obesity.

14 Claims, 6 Drawing Sheets

Fig. 1

ATG AAT CCA TTT CAT GCA TCT TGT TGG AAC ACC TCT GCC GAA CTT TTA AAC AAA TCC TGG
Met Asn Pro Phe His Ala Ser Cys Trp Asn Thr Ser Ala Glu Leu Leu Asn Lys Ser Trp

AAT AAA GAG TTT GCT TAT CAA ACT GCC AGT GTG GTA GAT ACA GTC ATC CTC CCT TCC ATG
Asn Lys Glu Phe Ala Tyr Gln Thr Ala Ser Val Val Asp Thr Val Ile Leu Pro Ser Met

ATT GGG ATT ATC TGT TCA ACA GGG CTG GTT GGC AAC ATC CTC ATT GTA TTC ACT ATA ATA
Ile Gly Ile Ile Cys Ser Thr Gly Leu Val Gly Asn Ile Leu Ile Val Phe Thr Ile Ile

AGA TCC AGG AAA AAA ACA GTC CCT GAC ATC TAT ATC TGC AAC CTG GCT GTG GCT GAT TTG
Arg Ser Arg Lys Lys Thr Val Pro Asp Ile Tyr Ile Cys Asn Leu Ala Val Ala Asp Leu

GTC CAC ATA GTT GGA ATG CCT TTT CTT ATT CAC CAA TGG GCC CGA GGG GGA GAG TGG GTG
Val His Ile Val Gly Met Pro Phe Leu Ile His Gln Trp Ala Arg Gly Gly Glu Trp Val

TTT GGG GGG CCT CTC TGC ACC ATC ATC ACA TCC CTG GAT ACT TGT AAC CAA TTT GCC TGT
Phe Gly Gly Pro Leu Cys Thr Ile Ile Thr Ser Leu Asp Thr Cys Asn Gln Phe Ala Cys

AGT GCC ATC ATG ACT GTA ATG AGT GTG GAC AGG TAC TTT GCC CTC GTC CAA CCA TTT CGA
Ser Ala Ile Met Thr Val Met Ser Val Asp Arg Tyr Phe Ala Leu Val Gln Pro Phe Arg

CTG ACA CGT TGG AGA ACA AGG TAC AAG ACC ATC CGG ATC AAT TTG GGC CTT TGG GCA GCT
Leu Thr Arg Trp Arg Thr Arg Tyr Lys Thr Ile Arg Ile Asn Leu Gly Leu Trp Ala Ala

TCC TTT ATC CTG GCA TTG CCT GTC TGG GTC TAC TCG AAG GTC ATC AAA TTT AAA GAC GGT
Ser Phe Ile Leu Ala Leu Pro Val Trp Val Tyr Ser Lys Val Ile Lys Phe Lys Asp Gly

GTT GAG AGT TGT GCT TTT GAT TTG ACA TCC CCT GAC GAT GTA CTC TGG TAT ACA CTT TAT
Val Glu Ser Cys Ala Phe Asp Leu Thr Ser Pro Asp Asp Val Leu Trp Tyr Thr Leu Tyr

TTG ACG ATA ACA ACT TTT TTT TTC CCT CTA CCC TTG ATT TTG GTG TGC TAT ATT TTA ATT
Leu Thr Ile Thr Thr Phe Phe Phe Pro Leu Pro Leu Ile Leu Val Cys Tyr Ile Leu Ile

TTA TGC TAT ACT TGG GAG ATG TAT CAA CAG AAT AAG GAT GCC AGA TGC TGC AAT CCC AGT
Leu Cys Tyr Thr Trp Glu Met Tyr Gln Gln Asn Lys Asp Ala Arg Cys Cys Asn Pro Ser

GTA CCA AAA CAG AGA GTG ATG AAG TTG ACA AAG ATG GTG CTG GTG CTG GTG GTA GTC TTT
Val Pro Lys Gln Arg Val Met Lys Leu Thr Lys Met Val Leu Val Leu Val Val Val Phe

ATC CTG AGT GCT GCC CCT TAT CAT GTG ATA CAA CTG GTG AAC TTA CAG ATG GAA CAG CCC
Ile Leu Ser Ala Ala Pro Tyr His Val Ile Gln Leu Val Asn Leu Gln Met Glu Gln Pro

ACA CTG GCC TTC TAT GTG GGT TAT TAC CTC TCC ATC TGT CTC AGC TAT GCC AGC AGC AGC
Thr Leu Ala Phe Tyr Val Gly Tyr Tyr Leu Ser Ile Cys Leu Ser Tyr Ala Ser Ser Ser

ATT AAC CCT TTT CTC TAC ATC CTG CTG AGT GGA AAT TTC AGA AAA CGT CTG CCT CAA ATC
Ile Asn Pro Phe Leu Tyr Ile Leu Leu Ser Gly Asn Phe Gln Lys Arg Leu Pro Gln Ile

CAA AGA AGA GCG ACT GAG AAG GAA ATC AAC AAT ATG GGA AAC ACT CTG AAA TCA CAC TTT
Gln Arg Arg Ala Thr Glu Lys Glu Ile Asn Asn Met Gly Asn Thr Leu Lys Ser His Phe

TAG

SEQUENCE LISTING

```
<160> NUMBER OF SEQ ID NOS: 19

<210> SEQ ID NO 1
<211> LENGTH: 26
<212> TYPE: DNA
<213> ORGANISM: Artificial Sequence
<220> FEATURE:
<223> OTHER INFORMATION: primer

<400> SEQUENCE: 1
gtcgacatga atccatttca tgcatc                                          26

<210> SEQ ID NO 2
<211> LENGTH: 26
<212> TYPE: DNA
<213> ORGANISM: Artificial Sequence
<220> FEATURE:
<223> OTHER INFORMATION: primer

<400> SEQUENCE: 2
actagtctaa aagtgtgatt tcagag                                          26

<210> SEQ ID NO 3
<211> LENGTH: 340
<212> TYPE: PRT
<213> ORGANISM: Human

<400> SEQUENCE: 3

Met Asn Pro Phe His Ala Ser Cys Trp Asn Thr Ser Ala Glu Leu Leu
                 5                  10                  15
```

-continued

```
Asn Lys Ser Trp Asn Lys Glu Phe Ala Tyr Gln Thr Ala Ser Val Val
         20                  25                  30
Asp Thr Val Ile Leu Pro Ser Met Ile Gly Ile Ile Cys Ser Thr Gly
             35                  40                  45
Leu Val Gly Asn Ile Leu Ile Val Phe Thr Ile Ile Arg Ser Arg Lys
 50                  55                  60
Lys Thr Val Pro Asp Ile Tyr Ile Cys Asn Leu Ala Val Ala Asp Leu
 65                  70                  75                  80
Val His Ile Val Gly Met Pro Phe Leu Ile His Gln Trp Ala Arg Gly
                 85                  90                  95
Gly Glu Trp Val Phe Gly Gly Pro Leu Cys Thr Ile Ile Thr Ser Leu
            100                 105                 110
Asp Thr Cys Asn Gln Phe Ala Cys Ser Ala Ile Met Thr Val Met Ser
        115                 120                 125
Val Asp Arg Tyr Phe Ala Leu Val Gln Pro Phe Arg Leu Thr Arg Trp
130                 135                 140
Arg Thr Arg Tyr Lys Thr Ile Arg Ile Asn Leu Gly Leu Trp Ala Ala
145                 150                 155                 160
Ser Phe Ile Leu Ala Leu Pro Val Trp Val Tyr Ser Lys Val Ile Lys
                165                 170                 175
Phe Lys Asp Gly Val Glu Ser Cys Ala Phe Asp Leu Thr Ser Pro Asp
            180                 185                 190
Asp Val Leu Trp Tyr Thr Leu Tyr Leu Thr Ile Thr Thr Phe Phe Phe
        195                 200                 205
Pro Leu Pro Leu Ile Leu Val Cys Tyr Ile Leu Ile Leu Cys Tyr Thr
    210                 215                 220
Trp Glu Met Tyr Gln Gln Asn Lys Asp Ala Arg Cys Cys Asn Pro Ser
225                 230                 235                 240
Val Pro Lys Gln Arg Val Met Lys Leu Thr Lys Met Val Leu Val Leu
                245                 250                 255
Val Val Val Phe Ile Leu Ser Ala Ala Pro Tyr His Val Ile Gln Leu
            260                 265                 270
Val Asn Leu Gln Met Glu Gln Pro Thr Leu Ala Phe Tyr Val Gly Tyr
        275                 280                 285
Tyr Leu Ser Ile Cys Leu Ser Tyr Ala Ser Ser Ser Ile Asn Pro Phe
    290                 295                 300
Leu Tyr Ile Leu Leu Ser Gly Asn Phe Gln Lys Arg Leu Pro Gln Ile
305                 310                 315                 320
Gln Arg Arg Ala Thr Glu Lys Glu Ile Asn Asn Met Gly Asn Thr Leu
                325                 330                 335
Lys Ser His Phe
            340

<210> SEQ ID NO 4
<211> LENGTH: 1035
<212> TYPE: DNA
<213> ORGANISM: Human

<400> SEQUENCE: 4
gtcgacatga atccatttca tgcatcttgt tggaacacct ctgccgaact tttaaacaaa    60
tcctggaata aagagtttgc ttatcaaact gccagtgtgg tagatacagt catcctccct   120
tccatgattg ggattatctg ttcaacaggg ctggttggca acatcctcat tgtattcact   180
ataataagat ccaggaaaaa aacagtccct gacatctata tctgcaacct ggctgtggct   240
```

```
gatttggtcc acatagttgg aatgcctttt cttattcacc aatgggcccg aggggagag      300 tgggtgtttg gggggcctct ctgcaccatc atcacatccc tggatacttg taaccaattt      360
gcctgtagtg ccatcatgac tgtaatgagt gtggacaggt actttgccct cgtccaacca      420
tttcgactga cacgttggag aacaaggtac aagaccatcc ggatcaattt gggcctttgg      480
gcagcttcct ttatcctggc attgcctgtc tgggtctact cgaaggtcat caaatttaaa      540
gacggtgttg agagttgtgc ttttgatttg acatcccctg acgatgtact ctggtataca      600
ctttatttga cgataacaac ttttttttc cctctaccct tgattttggt gtgctatatt       660
ttaattttat gctatacttg ggagatgtat caacagaata aggatgccag atgctgcaat      720
cccagtgtac caaaacagag agtgatgaag ttgacaaaga tggtgctggt gctggtggta      780
gtctttatcc tgagtgctgc ccctatcat gtgatacaac tggtgaactt acagatggaa       840
cagcccacac tggccttcta tgtgggttat tacctctcca tctgtctcag ctatgccagc      900
agcagcatta acccttttct ctacatcctg ctgagtggaa atttccagaa acgtctgcct      960
caaatccaaa gaagagcgac tgagaaggaa atcaacaata tgggaaacac tctgaaatca      1020
cacttttaga ctagt                                                      1035
```

<210> SEQ ID NO 5
<211> LENGTH: 757
<212> TYPE: RNA
<213> ORGANISM: Human
<220> FEATURE:
<223> OTHER INFORMATION: riboprobe

<400> SEQUENCE: 5

```
caaaagcugg agcuccaccg cgguggcggc cgcucuagcc ccuaaaagug ugauuucaga       60
guguuuccca uauguugau uccuucuca gucgcucuuc uuuggauuug aggcagacgu        120
uucuggaaau uuccacucag caggauguag agaaaagggu uaaugcugcu gcuggcauag      180
cugagacaga uggagaggua auaacccaca uagaaggcca guguggcug uuccaucugu       240 aaguucacca guuguaucac augauaaggg gcagcacuca ggauaaagac uaccaccagc      300
accagcacca ucuuugucaa cuucaucacu cucuguuuug guacacuggg auugcagcau     360
cuggcauccu uauucuguug auacaucuuc caaguauagc auaaaauuaa aauauagcac      420
accaaaauca agguagagg gaaaaaaaa guuguuaucg ucaauaaag uguauaccag         480 aguacaucgu caggaugu caaucaaaa gcacaacucu caaccgucu uuuaaauuug         540 augaccuucg aguagaccca gacaggcaau gccaggauaa aggaagcugc ccaaaggccc      600
aaauugaucc ggauggucuu guaccuuguu cuccaacgug ucagucgaaa ugguuggacg      660
agggcaaagu accuguccac acucauuaca gucaugaugg cacuacaggc aaauugguua     720 caaguauucca gggaugugau gaugugcag agaggcc                              757
```

<210> SEQ ID NO 6
<211> LENGTH: 19
<212> TYPE: PRT
<213> ORGANISM: Human
<220> FEATURE:
<221> NAME/KEY: DISULFID
<222> LOCATION: 7..16
<223> OTHER INFORMATION: The 7th Cys and the 16th Cys form an
      intramolecular disulfide bond.

<400> SEQUENCE: 6

Asp Phe Asp Met Leu Arg Cys Met Leu Gly Arg Val Tyr Arg Pro Cys
1               5                   10                  15

Trp Gln Val
      19

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
atgaatccat tcatgcatc ttgt                                          24

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
ctaaaagtgt gatttcagag tgttt                                        25

<210> SEQ ID NO 9
<211> LENGTH: 1023
<212> TYPE: DNA
<213> ORGANISM: Human

<400> SEQUENCE: 9
atgaatccat tcatgcatc ttgttggaac acctctgccg aacttttaaa caaatcctgg    60
aataaagagt ttgcttatca aactgccagt gtggtagata cagtcatcct cccttccatg   120
attgggatta tctgttcaac agggctggtt ggcaacatcc tcattgtatt cactataata   180
agatccagga aaaaacagt ccctgacatc tatatctgca acctggctgt ggctgatttg    240
gtccacatag ttggaatgcc ttttcttatt caccaatggg cccgaggggg agagtgggtg   300 tttgggggc ctctctgcac catcatcaca tccctggata cttgtaacca atttgcctgt    360
agtgccatca tgactgtaat gagtgtggac aggtactttg ccctcgtcca accatttcga   420
ctgacacgtt ggagaacaag gtacaagacc atccggatca atttgggcct ttgggcagct   480
tcctttatcc tggcattgcc tgtctgggtc tactcgaagg tcatcaaatt taaagacggt   540
gttgagagtt gtgcttttga tttgacatcc cctgacgatg tactctggta tacactttat   600
ttgacgataa caacttttt tttccctcta cccttgattt tggtgtgcta tatttttatt    660
ttatgctata cttgggagat gtatcaacag aataaggatg ccagatgctg caatcccagt   720
gtaccaaaac agagagtgat gaagttgaca aagatggtgc tggtgctggt ggtagtcttt   780
atcctgagtg ctgcccctta tcatgtgata caactggtga acttacagat ggaacagccc   840
acactggcct tctatgtggg ttattacctc tccatctgtc tcagctatgc cagcagcagc   900
attaaccctt ttctctacat cctgctgagt ggaaatttcc agaaacgtct gcctcaaatc   960
caaagaagag cgactgagaa ggaaatcaac aatatgggaa acactctgaa atcacacttt  1020
tag                                                               1023

<210> SEQ ID NO 10
<211> LENGTH: 18
<212> TYPE: PRT
<213> ORGANISM: Human
<220> FEATURE:
<221> NAME/KEY: DISULFID

```
<222> LOCATION: 6..15
<223> OTHER INFORMATION: The 6th Cys and the 15th Cys form an
      intramolecular disulfide bond.

<400> SEQUENCE: 10

Phe Asp Met Leu Arg Cys Met Leu Gly Arg Val Tyr Arg Pro Cys Trp
1               5                   10                  15
Gln Val
    18

<210> SEQ ID NO 11
<211> LENGTH: 17
<212> TYPE: PRT
<213> ORGANISM: Human
<220> FEATURE:
<221> NAME/KEY: DISULFID
<222> LOCATION: 5..14
<223> OTHER INFORMATION: The 5th Cys and the 14th Cys form an
      intramolecular disulfide bond.

<400> SEQUENCE: 11

Asp Met Leu Arg Cys Met Leu Gly Arg Val Tyr Arg Pro Cys Trp Gln
1               5                   10                  15  16
Val
17

<210> SEQ ID NO 12
<211> LENGTH: 16
<212> TYPE: PRT
<213> ORGANISM: Human
<220> FEATURE:
<221> NAME/KEY: DISULFID
<222> LOCATION: 4..13
<223> OTHER INFORMATION: The 4th Cys and the 13th Cys form an
      intramolecular disulfide bond.

<400> SEQUENCE: 12

Met Leu Arg Cys Met Leu Gly Arg Val Tyr Arg Pro Cys Trp Gln Val
1               5                   10                  15  16

<210> SEQ ID NO 13
<211> LENGTH: 15
<212> TYPE: PRT
<213> ORGANISM: Human
<220> FEATURE:
<221> NAME/KEY: DISULFID
<222> LOCATION: 3..12
<223> OTHER INFORMATION: The 3rd Cys and the 12th Cys form an
      intramolecular disulfide bond.

<400> SEQUENCE: 13

Leu Arg Cys Met Leu Gly Arg Val Tyr Arg Pro Cys Trp Gln Val
1               5                   10                  15

<210> SEQ ID NO 14
<211> LENGTH: 14
<212> TYPE: PRT
<213> ORGANISM: Human
<220> FEATURE:
<221> NAME/KEY: DISULFID
<222> LOCATION: 2..11
<223> OTHER INFORMATION: The 2nd Cys and the 11th Cys form an
      intramolecular disulfide bond.

<400> SEQUENCE: 14

Arg Cys Met Leu Gly Arg Val Tyr Arg Pro Cys Trp Gln Val
1               5                   10              14
```

```
<210> SEQ ID NO 15
<211> LENGTH: 13
<212> TYPE: PRT
<213> ORGANISM: Human
<220> FEATURE:
<221> NAME/KEY: DISULFID
<222> LOCATION: 1..10
<223> OTHER INFORMATION: The 1st Cys and the 10th Cys form an
      intramolecular disulfide bond.

<400> SEQUENCE: 15

Cys Met Leu Gly Arg Val Tyr Arg Pro Cys Trp Gln Val
1               5                   10          13

<210> SEQ ID NO 16
<211> LENGTH: 353
<212> TYPE: PRT
<213> ORGANISM: Rat

<400> SEQUENCE: 16

Met Asp Leu Gln Thr Ser Leu Ser Thr Gly Pro Asn Ala Ser Asn
1               5                   10                  15

Ile Ser Asp Gly Gln Asp Asn Leu Thr Leu Pro Gly Ser Pro Arg
                20                  25                  30

Thr Gly Ser Val Ser Tyr Ile Asn Ile Ile Met Pro Ser Val Phe Gly
                35                  40                  45

Thr Ile Cys Leu Leu Gly Ile Val Gly Asn Ser Thr Val Ile Phe Ala
        50                  55                  60

Val Val Lys Lys Ser Lys Leu His Trp Cys Ser Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
            115                 120                 125

Thr Ser Thr Tyr Ile Leu Thr Ala Met Thr Ile Asp Arg Tyr Leu Ala
    130                 135                 140

Thr Val His Pro Ile Ser Ser Thr Lys Phe Arg Lys Pro Ser Met Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Lys Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
```

```
                    290                 295                 300
Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Thr
                325                 330                 335

Val Ser Asn Ala Gln Thr Ala Asp Glu Glu Arg Thr Glu Ser Lys Gly
                340                 345                 350

Thr
353

<210> SEQ ID NO 17
<211> LENGTH: 422
<212> TYPE: PRT
<213> ORGANISM: Human

<400> SEQUENCE: 17

Met Ser Val Gly Ala Met Lys Lys Gly Val Gly Arg Ala Val Gly Leu
1               5                   10                  15

Gly Gly Gly Ser Gly Cys Gln Ala Thr Glu Glu Asp Pro Leu Pro Asn
                20                  25                  30

Cys Gly Ala Cys Ala Pro Gly Gln Gly Gly Arg Arg Trp Arg Leu Pro
            35                  40                  45

Gln Pro Ala Trp Val Glu Gly Ser Ser Ala Arg Leu Trp Glu Gln Ala
50                  55                  60

Thr Gly Thr Gly Trp Met Asp Leu Glu Ala Ser Leu Leu Pro Thr Gly
65                  70                  75                  80

Pro Asn Ala Ser Asn Thr Ser Asp Gly Pro Asp Asn Leu Thr Ser Ala
                85                  90                  95

Gly Ser Pro Pro Arg Thr Gly Ser Ile Ser Tyr Ile Asn Ile Ile Met
                100                 105                 110

Pro Ser Val Phe Gly Thr Ile Cys Leu Leu Gly Ile Ile Gly Asn Ser
            115                 120                 125

Thr Val Ile Phe Ala Val Val Lys Lys Ser Lys Leu His Trp Cys Asn
130                 135                 140

Asn Val Pro Asp Ile Phe Ile Ile Asn Leu Ser Val Val Asp Leu Leu
145                 150                 155                 160

Phe Leu Leu Gly Met Pro Phe Met Ile His Gln Leu Met Gly Asn Gly
                165                 170                 175

Val Trp His Phe Gly Glu Thr Met Cys Thr Leu Ile Thr Ala Met Asp
            180                 185                 190

Ala Asn Ser Gln Phe Thr Ser Thr Tyr Ile Leu Thr Ala Met Ala Ile
            195                 200                 205

Asp Arg Tyr Leu Ala Thr Val His Pro Ile Ser Ser Thr Lys Phe Arg
210                 215                 220

Lys Pro Ser Val Ala Thr Leu Val Ile Cys Leu Leu Trp Ala Leu Ser
225                 230                 235                 240

Phe Ile Ser Ile Thr Pro Val Trp Leu Tyr Ala Arg Leu Ile Pro Phe
                245                 250                 255

Pro Gly Gly Ala Val Gly Cys Gly Ile Arg Leu Pro Asn Pro Asp Thr
            260                 265                 270

Asp Leu Tyr Trp Phe Thr Leu Tyr Gln Phe Phe Leu Ala Phe Ala Leu
            275                 280                 285

Pro Phe Val Val Ile Thr Ala Ala Tyr Val Arg Ile Leu Gln Arg Met
290                 295                 300
```

```
Thr Ser Ser Val Ala Pro Ala Ser Gln Arg Ser Ile Arg Leu Arg Thr
305                 310                 315                 320

Lys Arg Val Thr Arg Thr Ala Ile Ala Ile Cys Leu Val Phe Phe Val
            325                 330                 335

Cys Trp Ala Pro Tyr Tyr Val Leu Gln Leu Thr Gln Leu Ser Ile Ser
        340                 345                 350

Arg Pro Thr Leu Thr Phe Val Tyr Leu Tyr Asn Ala Ala Ile Ser Leu
            355                 360                 365

Gly Tyr Ala Asn Ser Cys Leu Asn Pro Phe Val Tyr Ile Val Leu Cys
        370                 375                 380

Glu Thr Phe Arg Lys Arg Leu Val Leu Ser Val Lys Pro Ala Ala Gln
385                 390                 395                 400

Gly Gln Leu Arg Ala Val Ser Asn Ala Gln Thr Ala Asp Glu Glu Arg
                405                 410                 415

Thr Glu Ser Lys Gly Thr
                420         422

<210> SEQ ID NO 18
<211> LENGTH: 1074
<212> TYPE: DNA
<213> ORGANISM: Rat

<400> SEQUENCE: 18
gtcgacatgg atctgcaaac ctcgttgctg tccactggcc ccaatgccag caacatctcc     60
gatggccagg ataatctcac attgccgggg tcacctcctc gcacagggag tgtctcctac    120
atcaacatca ttatgccttc cgtgtttggt accatctgtc tcctgggcat cgtgggaaac    180
tccacggtca tctttgctgt ggtgaagaag tccaagctac actggtgcag caacgtcccc    240
gacatcttca tcatcaacct ctctgtggtg gatctgctct tcctgctggg catgcctttc    300
atgatccacc agctcatggg gaacggcgtc tggcactttg ggaaaccat gtgcacccctc    360 atcacagcca tggacgccaa cagtcagttc actagcacct acatcctgac tgccatgacc    420
attgaccgct acttggccac cgtccaccce atctcctcca ccaagttccg gaagccctcc    480
atggccaccc tggtgatctg cctcctgtgg gcgctctcct tcatcagtat caccectgtg    540 tggctctacg ccaggctcat tcccttccca gggggtgctg tgggctgtgg catccgcctg    600
ccaaacccgg acactgacct ctactggttc actctgtacc agttttttcct ggcctttgcc    660 cttccgtttg tggtcattac cgccgcatac gtgaaaatac tacagcgcat gacgtcttcg    720
gtggccccag cctcccaacg cagcatccgg cttcggacaa agagggtgac ccgcacggcc    780
attgccatct gtctggtctt ctttgtgtgc tgggcaccct actatgtgct gcagctgacc    840
cagctgtcca tcagccgccc gaccctcacg tttgtctact gtacaacgc ggccatcagc    900 ttgggctatg ctaacagctg cctgaacccc tttgtgtaca gtgctctctg tgagaccttt    960
cgaaaacgct tggtgttgtc agtgaagcct gcagcccagg ggcagctccg cacggtcagc   1020
aacgctcaga cagctgatga ggagaggaca gaaagcaaag gcacctgaac tagt          1074

<210> SEQ ID NO 19
<211> LENGTH: 1275
<212> TYPE: DNA
<213> ORGANISM: Human

<400> SEQUENCE: 19
taggtgatgt cagtgggagc catgaagaag ggagtgggga gggcagttgg gcttggaggc     60
ggcagcggct gccaggctac ggaggaagac ccccttccca actgcggggc ttgcgctccg    120
```

-continued

```
ggacaaggtg gcaggcgctg gaggctgccg cagcctgcgt gggtggaggg gagctcagct      180
cggttgtggg agcaggcgac cggcactggc tggatggacc tggaagcctc gctgctgccc      240
actggtccca acgccagcaa cacctctgat ggccccgata acctcacttc ggcaggatca      300
cctcctcgca cggggagcat ctcctacatc aacatcatca tgccttcggt gttcggcacc      360
atctgcctcc tggcatcat cgggaactcc acggtcatct tcgcggtcgt gaagaagtcc       420
aagctgcact ggtgcaacaa cgtccccgac atcttcatca tcaacctctc ggtagtagat      480
ctcctctttc tcctgggcat gcccttcatg atccaccagc tcatgggcaa tggggtgtgg      540
cactttgggg agaccatgtg caccctcatc acggccatgg atgccaatag tcagttcacc      600
agcacctaca tcctgaccgc catggccatt gaccgctacc tggccactgt ccaccccatc      660
tcttccacga agttccggaa gccctctgtg gccaccctgg tgatctgcct cctgtgggcc      720
ctctccttca tcagcatcac ccctgtgtgg ctgtatgcca gactcatccc cttcccagga      780
ggtgcagtgg gctgcggcat acgcctgccc aacccagaca ctgacctcta ctggttcacc      840
ctgtaccagt ttttcctggc ctttgccctg ccttttgtgg tcatcacagc cgcatacgtg      900
aggatcctgc agcgcatgac gtcctcagtg gcccccgcct cccagcgcag catccggctg      960
cggacaaaga gggtgacccg cacagccatc gccatctgtc tggtcttctt tgtgtgctgg     1020
gcaccctact atgtgctaca gctgacccag ttgtccatca gccgcccgac cctcaccttt     1080
gtctacttat acaatgcggc catcagcttg ggctatgcca acagctgcct caaccccttt     1140
gtgtacatcg tgctctgtga gacgttccgc aaacgcttgg tcctgtcggt gaagcctgca     1200
gcccaggggc agcttcgcgc tgtcagcaac gctcagacgg ctgacgagga gaggacagaa     1260
agcaaaggca cctga                                                      1275
```

METHOD FOR SCREENING MCH RECEPTOR ANTAGONIST/AGONIST

This application is the National Phase filing of International Patent Application No. PCT/JP01/05809, filed 04 Jul. 2001.

TECHNICAL FIELD

The present invention relates to a method for screening an anti-obesity agent or an agent for controlling appetite, which is characterized by using an orphan receptor protein represented by SEQ ID NO: 3 (WO 00/49046 (PCT/JP00/00927)) or a salt thereof and MCH (Melanin Concentrating Hormone)(Endocrinology, vol. 125, 1660-1665 (1989), etc), a derivative or a salt thereof.

BACKGROUND ART

Regulations of important biological functions, such as homeostasis, reproduction, individual development, metabolism, growth, regulations of nervous system, cardiovascular system, immunological system, digestive system and metabolic system, and sensory system are conducted through corresponding responses of cells which accept various endogenous factors such as hormones and neurotransmitter, or organoleptic stimulants such as light and odor via receptors specific thereto on cell membranes. Many receptors of hormones and neurotransmitters involved in these regulations of functions are coupled with guanine nucleotide-binding proteins (hereinafter sometimes referred to as G-proteins) and activate the G-proteins to transmit signals into cells, which then express a variety of functions. In addition, these receptor proteins possess commonly seven transmembrane domains and are thus generically referred to as G-protein-coupled receptors or seven-transmembrane-type receptors. It is known that the interaction of various existing hormones and neurotransmitters with receptor proteins thereof plays a significant role in such regulations of biological functions. However, there are still many unclear points as to the existence of unidentified active substances (e.g. hormones, neurotransmitters) and receptors thereof.

In recent years, sequence information have been accumulated by determination of human genome DNAs or cDNAs derived from various human tissues, and genetically analytical techniques have also been advanced, and as a result, human genes have been elucidated at an accelerating pace. Correspondingly, there are many genes detected, which are predicted to encode proteins with their functions still unknown. G-protein-coupled receptors can be clearly selected from these proteins on the basis of not only presence of seven transmembrane domains, but also presence of many common nucleic acid sequences or amino acid sequences. On the other hand, such G-protein-coupled receptors have also been obtained by Polymerase Chain Reaction (PCR) using the structural similarity as described above. Among G-protein-coupled receptors thus obtained until now, some are a subtype receptor having high structural similarity to known receptors, and thus their ligands may be easily predicted. In most cases, however, it is impossible to predict their endogenous ligands, and the ligands of these receptors have not been found yet. In this connection, these receptors are referred to as orphan receptors. The unidentified endogenous ligands of these orphan receptors may be involved in biological phenomena, which are not well characterized due to the unidentification of the ligands. Thus, if such ligands are associated with important physiological actions and pathological conditions, it is expected that development of agonists or antagonists of the receptors may lead to creation of innovative pharmaceuticals (Stadel, J. et al., TiPS 18, 430-437, 1997; Marchese, A. et al., TiPS 20, 370-375, 1999; Civelli, O. et al., Brain Res. 848, 63-65, 1999). But, not so many ligands of orphan G protein-coupled receptors are actually identified until now.

Recently, some research groups made an attempt to search for ligands of these orphan receptors, and reported isolation of new physiologically active peptides and/or determination of their structures. Reinsheid et al. and Meunier et al. separately isolated a novel peptide called orphanin FQ or nociceptin from pig brain extract or rat brain extract using as an index the response in animal cells expressing an orphan G-protein-coupled receptor LC132 or ORL1 by induction of cDNA encoding either into the cells, and determined the sequence thereof (Reinsheid, R. K. et al., Science 270, 792-794, 1995; Meunier, J. C. et al., Nature 377, 532-535, 1995). It was reported that this peptide was involved in pain sensation, and further shown that the peptide was involved in memory as the result of investigation of the receptor-knockout mice.

Then, until now, novel peptides such as PrRP (prolactin releasing peptide), orexin, apelin, ghrelin, and GALP (galanin-like peptide) have been isolated as ligands of orphan G-protein-coupled receptors by the same methods as described above (Hinuma, S. et al., Nature 393, 272-276, 1998; Sakurai, T. et al., Cell 92, 573-585, 1998; Tatemoto, K. et al., Bichem. Biophys. Res. Commun. 251, 471-476, 1998; Kojima, M. et al., Nature 402, 656-660, 1999; Ohtaki, T. et al., J. Biol. Chem. 274, 37041-37045, 1999).

On the other hand, some of receptors of physiologically active peptides, which had not been clarified before, were identified in a similar way. GPR38 was found as a receptor of motilin which was involved in intestinal contraction (Feighner, S. D. et al., Science 284, 2184-2188, 1999). In addition, SLC-1 was identified as a receptor of Melanin Concentrating Hormone (MCH) (Chambers, J. et al., Nature 400, 261-265, 1999; Saito, Y. et al., Nature 400, 265-269, 1999; Shimomura, Y. et al., Biochem. Biophys. Res. Commun. 261, 622-626, 1999; Lembo, P. M. C. et al., Nature Cell Biol. 1, 267-271, 1999; Bachner, D. et al., FEBS Lett. 457, 522-524, 1999), and GPR14 (SENR) was reported as a receptor of urotensin II (Ames, R. S. et al., Nature 401, 282-286, 1999; Mori, M. et al., Biochem. Biophys. Res. Commun. 265, 123-129, 1999; Nothacker, H.-P. et al., Nature Cell Biol. 1, 383-385, 1999; Liu, Q. et al., Biochem. Biophys. Res. Commun. 266, 174-178, 1999). MCH knock-out mice showed the wasting phenotype, indicating that MCH may be involved in obesity (Shimada, M. et al., Nature 396, 670-674, 1998), and identification of MCH receptor have made it possible to search for an antagonist of MCH receptor, which may serve as an anti-obesity agent. Further, it is also reported that urotensin II elicits heart ischemia when administered intravenously to a monkey, and thus it has a strong action on cardiovascular system (Ames, R. S. et al., Nature 401, 282-286, 1999).

As described above, in many cases, orphan receptors and their ligands are involved in novel physiological functions, and thus it is expected that the elucidation thereof may lead to development of a new pharmaceutical. However, because of many difficulties in searching for a ligand of an orphan receptor, even though plenty of orphan receptors have been discovered, only a few thereof are made clear in light of ligand.

Watanabe et al. found a novel receptor SLT as an orphan G-protein-coupled receptor (a protein having the amino acid sequence shown by SEQ ID NO: 3 in the present specification; hereinafter referred to simply as SLT), but it has been unclear until now what is the ligand of the receptor.

DISCLOSURE OF THE INVENTION

The present inventors produced a CHO cell highly expressing a receptor protein SLT, and investigated a response of the receptor-expressing cell when a variety of animal tissue extracts or known peptides were added to the cell. As a result, it was unexpectedly found that MCH shows an inhibitory action on intracellular cAMP production in the CHO cell expressing the receptor SLT, indicating that MCH is an endogenous ligand of SLT.

Based on the finding, the present inventors first found a possibility of screening a therapeutic agent for diseases associated with MCH (e.g. MCH receptor antagonists or agonists, specifically, anti-obesity agent) using a screening system using MCH and SLT, more preferably, further in combination of a screening system using MCH and SLC-1.

Thus, the present invention provides:

(1) A method for screening a compound or a salt thereof that alters the binding property of MCH or a salt thereof to a protein shown by SEQ ID NO: 3 or a salt thereof, or a partial peptide thereof, an amide, an ester or a salt thereof, the method which comprises using Melanin Concentrating Hormone (MCH), a derivative or a salt thereof, and a protein shown by SEQ ID NO: 3 or a salt thereof, or a partial peptide thereof, an amide, an ester or a salt thereof;

(2) The screening method described in (1), which further comprises using SLC-1 or a salt thereof, or a partial peptide thereof, an amide, an ester or a salt thereof;

(3) A kit for screening a compound or a salt thereof that alters the binding property of MCH or a salt thereof to a protein shown by SEQ ID NO: 3 or a salt thereof, or a partial peptide thereof, an amide, an ester or a salt thereof, the kit which comprises MCH, a derivative or a salt thereof, and a protein shown by SEQ ID NO: 3 or a salt thereof, or a partial peptide thereof, an amide, an ester or a salt thereof;

(4) The screening kit described in (3), which further comprises SLC-1 or a salt thereof, or a partial peptide thereof, an amide, an ester or a salt thereof;

(5) A compound or a salt thereof that alters the binding property of MCH or a salt thereof to a protein shown by SEQ ID NO: 3 or a salt thereof, or a partial peptide thereof, an amide, an ester or a salt thereof, which is obtainable using the screening method described in (1) or the screening kit described in (3);

(6) A pharmaceutical agent comprising the compound or the salt thereof described in (5);

(7) The pharmaceutical agent described in (6), which is an anti-obesity agent;

(8) The screening method described in (1), wherein MCH is a peptide comprising the same or substantially the same amino acid sequence as the sequence shown by SEQ ID NO: 6;

(9) The screening kit described in (3), wherein MCH is a peptide comprising the same or substantially the same amino acid sequence as the sequence shown by SEQ ID NO: 6;

(10) The screening method described in (1), wherein said derivative is a peptide comprising the 5th residue through the 19th residue from the N-terminal of the amino acid sequence shown by SEQ ID NO: 6, an amide or an ester thereof;

(11) The screening kit described in (3), wherein said derivative is a peptide comprising the 5th residue through the 19th residue from the N-terminal of the amino acid sequence shown by SEQ ID NO: 6, an amide or an ester thereof;

(12) The screening method described in (1), wherein said derivative is a derivative of MCH, which is prepared using Bolton-Hunter reagent, or a derivative of a peptide comprising the 5th residue through the 19th residue from the N-terminal of the amino acid sequence shown by SEQ ID NO: 6, an amide or an ester thereof, which is prepared using Bolton-Hunter reagent;

(13) The screening kit described in (3), wherein said derivative is a derivative of MCH, which is prepared using Bolton-Hunter reagent, or a derivative of a peptide comprising the 5th residue through the 19th residue from the N-terminal of the amino acid sequence shown by SEQ ID NO: 6, an amide or an ester thereof, which is prepared using Bolton-Hunter reagent;

(14) The screening method described in (1), wherein said MCH, derivative or salt thereof is [$^{125}$I]-[N-(3-(4-hydroxy-3-iodophenyl)propionyl)-Met$^4$]-MCH(4-19) or a salt thereof;

(15) The screening kit described in (3), wherein said MCH, derivative or salt thereof is [$^{125}$I]-[N-(3-(4-hydroxy-3-iodophenyl)propionyl)-Met$^4$]-MCH(4-19) or a salt thereof;

(16) A method for screening a compound or a salt thereof that alters the binding property of (1) MCH, a derivative or a salt thereof to (2) (i) SLC-1 or a salt thereof, or a partial peptide thereof, an amide, an ester or a salt thereof, and/or (ii) a protein shown by SEQ ID NO: 3 or a salt thereof, or a partial peptide thereof, an amide, an ester or a salt thereof, which comprises using (i) MCH, a derivative or a salt thereof; (ii) SLC-1 or a salt thereof, or a partial peptide thereof, an amide, an ester or a salt thereof; and (iii) a protein shown by SEQ ID NO: 3 or a salt thereof, or a partial peptide thereof, an amide, an ester or a salt thereof;

(17) The screening method described in (16), which is for screening a compound or a salt thereof that alters preferentially the binding property of MCH, a derivative or a salt thereof to a protein shown by SEQ ID NO: 3 or a salt thereof, or a partial peptide thereof, an amide, an ester or a salt thereof;

(18) The screening method described in (16), which is for screening a compound or a salt thereof that alters preferentially the binding property of MCH, a derivative or a salt thereof to SLC-1 or a salt thereof, or a partial peptide thereof, an amide, an ester or a salt thereof;

(19) The screening method described in (16), which is for screening a compound or a salt thereof that alters preferentially the binding property of MCH, a derivative or a salt thereof to (i) a protein shown by SEQ ID NO: 3 or a salt thereof, or a partial peptide thereof, an amide, an ester or a salt thereof, and (ii) SLC-1 or a salt thereof, or a partial peptide thereof, an amide, an ester or a salt thereof;

(20) A kit for screening a compound or a salt thereof that alters the binding property of (1) MCH, a derivative or a salt thereof to (2) (i) SLC-1 or a salt thereof, or a partial peptide thereof, an amide, an ester or a salt thereof, and/or (ii) a protein shown by SEQ ID NO: 3 or a salt thereof, or a partial peptide thereof, an amide, an ester or a salt thereof, which comprises (i) MCH, a derivative or a salt thereof; (ii) SLC-1 or a salt thereof, or a partial peptide thereof, an amide, an ester or a salt thereof; and (iii) a protein shown by SEQ ID NO: 3 or a salt thereof, or a partial peptide thereof, an amide, an ester or a salt thereof.

BRIEF DESCRIPTION OF THE DRAWINGS

FIG. 1 shows the nucleic acid sequence of the DNA encoding a novel G-protein-coupled receptor protein hSLT (SEQ ID NO.: 9), which is derived from human hippocampus, and the amino acid sequence (SEQ ID NO.: 3) deduced therefrom.

Figure 2:
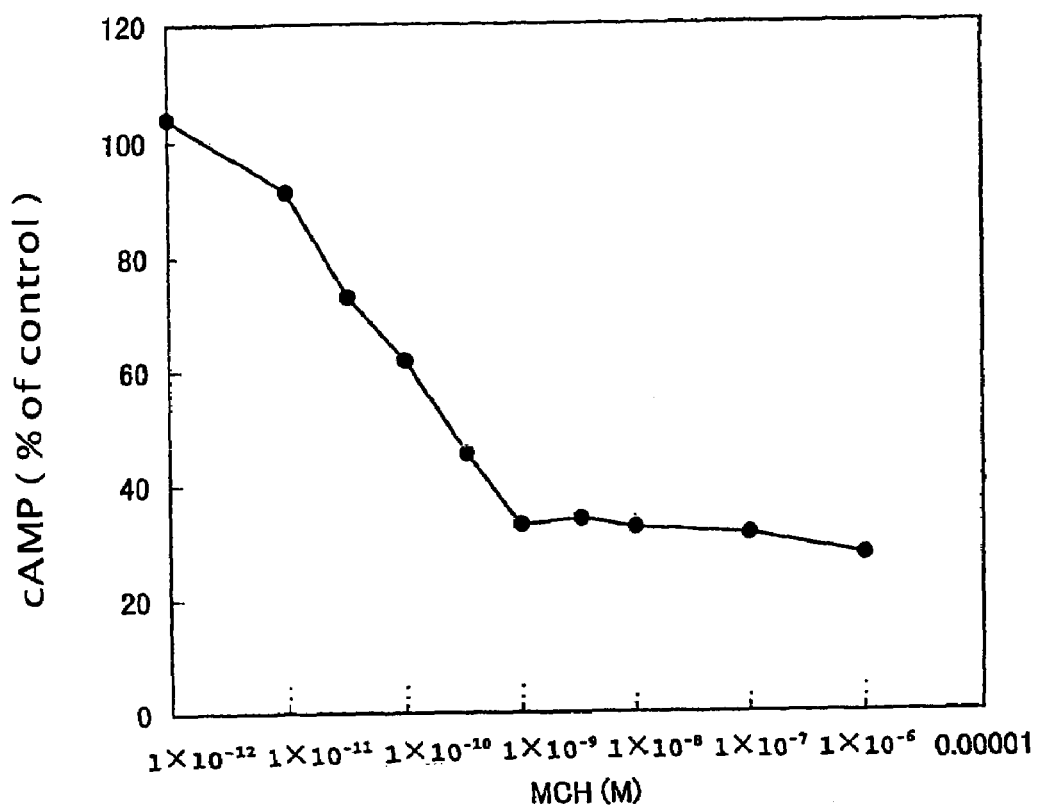
FIG. 2 shows the activity of MCH at various concentrations to inhibit cAMP production in CHO cells expressing human SLT.

In the specification, a term "substantially the same" means the substantial equivalence in activity of the polypeptide, for example, the binding activity of a ligand (MCH) to a receptor (SLT), a physiological property, or the like.

The methods for producing SLT or a salt thereof (hereinafter simply referred to as SLT) and MCH, a derivative or a salt thereof (hereinafter simply referred to as MCH) are described below in detail.

SLC-1 or a salt thereof (hereinafter sometimes simply referred to as SLC-1) is a MCH receptor, and can be used in the screening method of the present invention comprising use of SLT and MCH. It can be obtained using production methods described in e.g. Chambers, J. et al., Nature, vol. 400, 261-265, 1999; Saito, Y. et al., Nature, vol. 400, 265-269, 1999; Shimomura, Y. et al., Biochem. Biophys. Res. Commun., vol. 261, 622-626, 1999; Lembo, P. M. C. et al., Nature Cell Biol., vol. 1, 267-271, 1999; Bachner, D. et al., FEBS Lett., vol. 457, 522-524, 1999; and WO00/40725 (PCT/JP99/07336). The method for producing SLC-1 is also described below.

SLT, SLC-1 and MCH used in the present invention may be polypeptides derived from any tissues (e.g. hypophysis, pancreas, brain, kidney, liver, gonad, thyroid, gallbladder, bone marrow, adrenal gland, skin, muscle, lung, gastrointestinal tract, blood vessel, heart, etc.) or any cells from a human, a warm-blooded animal (e.g. guinea pig, rat, mouse, swine, sheep, bovine, monkey), and a fish.

SLT may be any polypeptides comprising the same or substantially the same amino acid sequence as that shown by SEQ ID NO: 3; SLC-1 may be any polypeptides comprising the same or substantially the same amino acid sequence as that shown by SEQ ID NO: 16 or NO: 17; MCH may be any polypeptides comprising the same or substantially the same amino acid sequence as that shown by SEQ ID NO: 6.

SLT includes a polypeptide comprising the amino acid sequence shown by SEQ ID NO: 3, and also a polypeptide having substantially the same activity as that of a polypeptide comprising the amino acid sequence shown by SEQ ID NO: 3. Herein, said activity includes ligand-binding activity, signal-transducing activity, and the like. The term "substantially the same" means qualitative equivalence, for example, in the ligand-binding activity. Therefore, quantitative factors, such as level of ligand binding activity, molecular weight of polypeptide may be different.

SLC-1 includes a polypeptide comprising the amino acid sequence shown by SEQ ID NO: 16 or NO: 17, and also a polypeptide having substantially the same activity as that of a polypeptide comprising the amino acid sequence shown by SEQ ID NO: 16 or NO: 17. Herein, said activity includes ligand-binding activity, signal-transducing activity, and the like. The term "substantially the same" means qualitative equivalence, for example, in the ligand-binding activity. Therefore, quantitative factors, such as level of ligand binding activity, molecular weight of polypeptide may be different.

MCH includes a polypeptide comprising the amino acid sequence shown by SEQ ID NO: 6, and also a polypeptide having substantially the same activity as that of a polypeptide comprising the amino acid sequence shown by SEQ ID NO: 6. Herein, said activity includes ligand-binding activity, signal-transducing activity, and the like. The term "substantially the same" means qualitative equivalence, for example, in the ligand-binding activity. Therefore, quantitative factors, such as level of ligand binding activity, molecular weight of polypeptide may be different.

In the present specification, SLT, SLC-1 and MCH are represented in accordance with a conventional peptide notation system, so that the N-terminal (amino terminal) is placed on the left side and the C-terminal (carboxyl terminal) on the right side. The polypeptide having the amino acid sequence shown by SEQ ID NO: 3, NO: 16, NO: 17 or NO: 6 usually has a carboxyl group (—COOH) or carboxylate (—COO$^-$) at the C-terminal, but may have an amide (—CONH$_2$) or ester (—COOR) at the C-terminal. R in said ester includes, for example, C$_{1-6}$ alkyl groups such as methyl, ethyl, n-propyl, isopropyl and n-butyl; C$_{3-8}$ cycloalkyl groups such as cyclopentyl and cyclohexyl; C$_{6-12}$ aryl groups such as phenyl and α-naphthyl; C$_{7-14}$ aralkyl groups such as phenyl-C$_{1-2}$ alkyl, such as benzyl, phenethyl and benzhydryl, and α-naphthyl-C$_{1-2}$ alkyl, such as α-naphthylmethyl; and also pivaloyloxymethyl groups generally used in an ester suitable for oral administration.

Examples of salts of SLT, SLC-1 and MCH used in the present invention include salts with physiologically acceptable bases (e.g., alkali metals) or acids (e.g., inorganic acids, organic acids). Especially, physiologically acceptable acid addition salts are preferred. Such salts include, for example, salts with inorganic acids (e.g., hydrochloric acid, phosphoric acid, hydrobromic acid, sulfuric acid) or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

SLT, SLC-1 and MCH used in the present invention can be produced by a known method (the method described in FEBS Letters, 398(1996), 253-258, or WO 96/18651) or a variant method thereof. Thus, it can be produced by a method of purify a polypeptide from cells or tissues of a human or a warm-blooded animal, or can be produced according to a peptide synthesis method described below. Alternatively, it can be produced by culturing a transformant containing the DNA encoding the protein (peptide) described below.

When the proteins are produced from tissues or cells of human, warm-blooded animal, amphibian or fish, the tissues or cells are homogenized, then extracted with an acid, an organic solvent or the like, and then the target protein is isolated and purified from the extract by a combination of salting out, dialysis, gel filtration and chromatography techniques such as reverse-phase chromatography, ion-exchange chromatography, affinity chromatography, etc.

SLT, SLC-1 and MCH used in the present invention can be produced according to a known method for protein (peptide) synthesis or by cleaving a protein (peptide) containing SLT, SLC-1 and/or MCH with a suitable peptidase. For example, the protein (peptide) synthesis method may be the solid- or liquid-phase synthesis method. That is, the desired protein (peptide) can be produced by condensing a partial peptide or an amino acid composing SLT, SLC-1 and/or MCH to the remaining part, followed by elimination of protecting groups, if any, from the product. The known methods for condensation and elimination of protecting groups can be found in e.g. the following (1) to (5):

(1) M. Bodanszky and M. A. Ondetti, Peptide Synthesis, Interscience Publisher, New York (1966);

(2) Schroeder and Luebke, The Peptide, Academic Press, New York (1965);

(3) Nobuo Izumiya et al., Basis and Experiments in Peptide Synthesis, Maruzen Co., Ltd. (1975);

(4) Haruaki Yajima and Shunpei Sakakibara, Biochemical Experimental Course 1, Protein Chemistry IV, 205, (1977); and (5) Haruaki Yajima (supervisor), Development of medicines, a second series, vol. 14, Peptide Synthesis, Hirokawashoten.

After the reaction, the protein (peptide) can be isolated and purified by a combination of conventional purification techniques such as solvent extraction, distillation, column chromatography, liquid chromatography and recrystallization. If the protein (peptide) is obtained in a free form by these methods, the product can be converted into a suitable salt form by a known method, or if the protein (peptide) is obtained in a salt form, it can be converted into a free form by a known method.

For synthesis of amide derivatives of SLT, SLC-1 and MCH, commercially available resins for protein synthesis, ones suitable for amide formation, can be used. Such resin includes, for example, chloromethyl resin, hydroxymethyl resin, benzhydryl amine resin, aminomethyl resin, 4-benzyloxybenzyl alcohol resin, 4-methylbenzhydryl amine resin, PAM resin, 4-hydroxymethylmethylphenylacetamidemethyl resin, polyacrylamide resin, 4-(2',4'-dimethoxyphenyl-hydroxymethyl) phenoxy resin, 4-(2',4'-dimethoxyphenyl-Fmoc aminoethyl)phenoxy resin, and so forth. Each amino acid with the α-amino group and side-chain functional group properly protected is condensed sequentially on the resin described above in accordance with the sequence of the desired peptide by a known condensation method. At the end of the reaction, the protein (peptide) is cleaved off from the resin, and various protecting groups are removed, and the product is subjected to a reaction of forming intramolecular disulfide bonds in a highly dilute solution to give the desired protein (peptide).

A wide variety of activating reagents usable for protein synthesis can be used for condensation of the protected amino acids described above, and carbodiimides are particularly preferable. Examples of such carbodiimides include DCC, N,N'-diisopropylcarbodiimide, N-ethyl-N'-(3-dimethylaminoprolyl)carbodiimide, etc. For activation by these reagents, the protected amino acids along with racemization inhibitors (e.g., HOBt, HOOBt) can be added to the resin directly or after the protected amino acids were previously activated as symmetric acid anhydrides or HOBt esters or HOOBt esters. The solvent used for activation of each protected amino acid or for condensation thereof with the resin can be selected as necessary from those solvents known to be usable in protein ((poly)peptide) condensation reaction. Examples of such solvent include acid amides such as N,N-dimethylformamide, N,N-dimethylacetamide and N-methylpyrrolidone; halogenated hydrocarbons such as methylene chloride and chloroform; alcohols such as trifluoroethanol; sulfoxides such as dimethyl sulfoxide; tertiary amines such as pyridine; ethers such as dioxane and tetrahydrofuran; nitrites such as acetonitrile and propionitrile; esters such as methyl acetate and ethyl acetate, or a suitable mixture thereof. The reaction temperature is usually selected as necessary within the range known to be usable in the reaction of forming peptide bonds, and usually the reaction temperature is selected within the range of about −20° C. to 50° C. The activated amino acid derivatives are used usually in excess (1.5- to 4-fold). When the condensation is insufficient as a result of a ninhydrin reaction test, the sufficient condensation is achieved by repeatedly carrying out the condensation reaction without elimination of the protecting groups. When the sufficient condensation is not achieved even by repeatedly carrying out the reaction, the unreacted amino acids are acetylated with acetic anhydride or acetyl imidazole to avoid adverse effect on the subsequent reaction.

The protecting groups for amino groups in amino acids as the starting materials include, for example, Z, Boc, t-pentyloxycarbonyl, isobornyloxycarbonyl, 4-methoxybenzyloxycarbonyl, Cl—Z, Br-Z, adamantyloxycarbonyl, trifluoroacetyl, phthaloyl, formyl, 2-nitrophenylsulphenyl, diphenylphosfinothioyl, Fmoc etc. The protecting groups for carboxyl groups include, for example, $C_{1-6}$ alkyl, $C_{3-8}$ cycloalkyl, $C_{7-14}$ aralkyl as above described for, or 2-adamantyl, 4-nitrobenzyl, 4-methoxybenzyl, 4-chlorobenzyl, phenacyl, benzyloxycarbonylhydrazide, t-butoxycarbonylhydrazide, tritylhydrazide, etc.

The hydroxyl group in serine and threonine can be protected by, for example, esterification or etherification. A suitable group used in this esterification includes, for example, lower alkanoyl groups such as acetyl group; alloyl groups such as benzoyl group; and carbonic acid-derived groups such as benzyloxycarbonyl group and ethoxycarbonyl group. A suitable group for etherification includes, for example, a benzyl group, tetrahydropyranyl group, t-butyl group, etc.

The protecting group used for the phenolic hydroxyl group in tyrosine includes, for example, Bzl, $Cl_2$-Bzl, 2-nitrobenzyl, Br-Z, t-butyl group, etc.

The protecting group used for imidazole in histidine includes, for example, Tos, 4-methoxy-2,3,6-trimethylbenzenesulfonyl, DNP, benzyloxymethyl, Bum, Boc, Trt, Fmoc, etc.

The activated carboxyl groups in the starting materials include, for example, the corresponding acid anhydrides, azides and active esters (i.e. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide and HOBt). The activated amino groups in the starting materials include, for example, the corresponding phosphoric acid amides.

Methods for removing (leaving) of the protecting groups include, for example, catalytic reduction in a hydrogen stream in the presence of a catalyst such as Pd-black or Pd-carbon; acid treatment using anhydrous hydrogen fluoride, methane sulfonic acid, trifluoromethane sulfonic acid, trifluoroacetic acid or a mixed solution thereof; base treatment using diisopropylethylamine, triethylamine, piperidine or piperazine; and reduction using sodium in liquid ammonia. The leaving reaction by the acid treatment is carried out generally at a temperature of about −20° C. to 40° C., and it is useful in the acid treatment to add a cation scavenger such as anisole, phenol, thioanisole, m-cresol, p-cresol, dimethylsulfide, 1,4-butanedithiol and 1,2-ethanedithiol. A 2,4-dinitrophenyl group used as a protecting group for imidazole in histidine can also be removed by treatment with thiophenol, while a formyl group used as a protecting group for indole in tryptophan can be removed for deprotection by acid treatment in the presence of 1,2-ethanedithiol or 1,4-butanedithiol above, or also by alkali treatment using dilute sodium hydroxide solution or dilute ammonia.

Protection and protecting groups for functional groups which should not participate in the reaction of the starting materials, elimination of the protecting groups, and activation of functional groups participating in the reaction can be selected as necessary from known groups and known methods.

Another method of obtaining amide derivatives of SLT, SLC-1 and MCH includes, for example, amidating the α-carboxyl group of the C-terminal amino acid, then extending a peptide chain at the amino terminal side until it attains desired chain length, and thereafter preparing the peptide from which the protecting group of the N-terminal α-amino group is removed, and a peptide (or an amino acid) from which the protecting group of the C-terminal carboxyl group is removed, and then condensing both the peptides in the mixed solvent as described above. The details of the condensation reaction are the same as described above. The protected peptide obtained by the condensation is purified, and all protecting groups are removed by the method descried above, whereby the desired crude protein (peptide) can be obtained. This crude protein (peptide) is purified by a wide variety of known purification techniques, and by lyophilizing its primary fraction, the desired amide derivative of the protein (peptide) can be obtained.

To obtain ester derivatives of SLT, SLC-1 and MCH, for example, the α-carboxyl group of a C-terminal amino acid is condensed with desired alcohol to form an amino acid ester, from which the desired ester derivative of the protein (peptide) can be obtained in the same manner as for the amide derivative of the protein (peptide).

The derivatives of MCH used in the present invention may include (1) partial peptides of MCH; (2) peptides of MCH wherein the constitutive amino acids are deleted, wherein amino acids is added to the constitutive amino acid sequence, or wherein the constitutive amino acids are substituted with other amino acids; or (3) a labeled form of MCH, the partial peptides described in (1) or the peptides described in (2). Those having a binding activity with SLT and SLC-1 are preferred.

Specifically, the partial peptides of MCH includes peptides comprising the partial sequence of the 5th through 19th residues from N-terminal of the amino acid sequence shown by SEQ ID NO: 6, amide derivatives, ester derivatives or salts thereof. More specifically, peptides having the amino acid sequence shown by SEQ ID NO:10, NO:11, NO:12, NO:13, NO:14, or NO:15, amide derivatives, ester derivatives or salts thereof are included.

Furthermore, for the screening with SLT and/or SLC-1 as described later, in particular, the peptide having the amino acid sequence shown by SEQ ID NO:12, amide derivatives, ester derivatives or salts thereof is preferably used.

Said peptides of MCH which have deletion of the constitutive amino acids, addition of amino acids to the constitutive amino acid sequence, or substitution of the constitutive amino acids with other amino acids may include those wherein one or more (preferably about 1 to 10, more preferably several (1 or 2)) amino acids of the amino acid sequence shown by SEQ ID NO: 6 are deleted, one or more (preferably about 1 to 10, more preferably about 1 to 5, even more preferably several (1 or 2)) amino acids are added to the amino acid sequence, and one or more (preferably about 1 to 10, more preferably about 1 to 5, even more preferably several (1 or 2)) amino acids of the amino acid sequence are substituted with other amino acids.

The substituent for an amino acid present in said amino acid sequence may be substantially the same one as the amino acid, and may be selected from amino acids of the group that the amino acid belongs to. Non-polar (hydrophobic) amino acid includes alanine, leucine, isoleucine, valine, proline, phenylalanine, tryptophan, methionine, etc. Polar (neutral) amino acid includes glycine, serine, threonin, cycteine, thyrosine, asparagine, glutamine, etc. Positively charged (basic) amino acid includes arginine, lysine, histidine, etc. Negatively charged (acidic) amino acid includes aspartic acid, glutamic acid, etc.

It is preferable that amino acids other than Cys in the constitutive amino acids of MCH are deleted or substituted.

The labeled form of MCH, the partial peptides described in (1) above or the peptides described in (2) above include those labeled with an isotope, those labeled with fluorescence (e.g. fluorescein), those biotinylated, and those labeled with enzyme according to a known method.

Specifically, MCH labeled with a radioisotope such as [$^{3}$H], [$^{125}$I], [$^{14}$C], [$^{35}$S] in a known manner may be used. The labeled form of MCH or a derivative thereof, which is prepared using Bolton-Hunter reagent according to a known method, may also be used.

Examples of the labeled form of MCH or its derivative include:

(1)

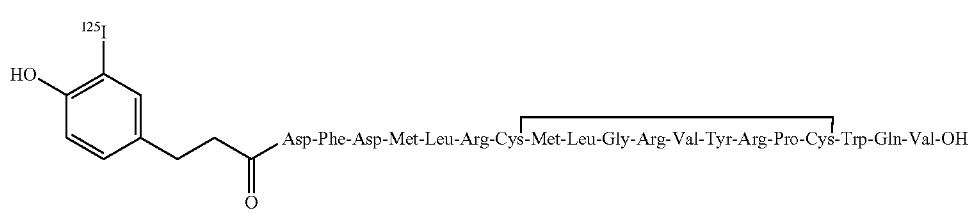

[$^{125}$I]——[N-(3-(4-hydroxy-3-iodophenyl)propionyl)-Asp$^{1}$]-MCH (2)
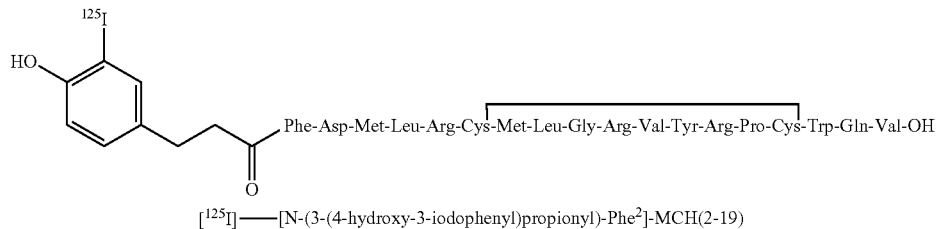
[125I]——[N-(3-(4-hydroxy-3-iodophenyl)propionyl)-Phe²]-MCH(2-19)
(3)
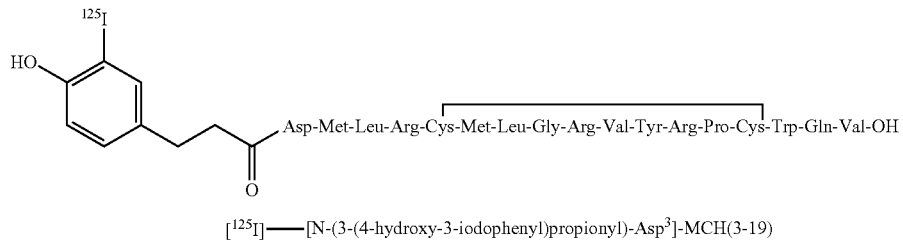
[125I]——[N-(3-(4-hydroxy-3-iodophenyl)propionyl)-Asp³]-MCH(3-19)
(4)
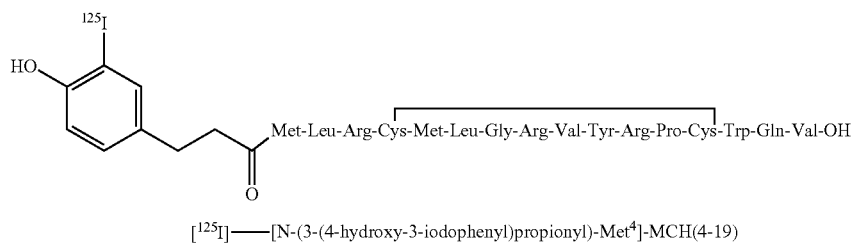
[125I]——[N-(3-(4-hydroxy-3-iodophenyl)propionyl)-Met⁴]-MCH(4-19)
(5)
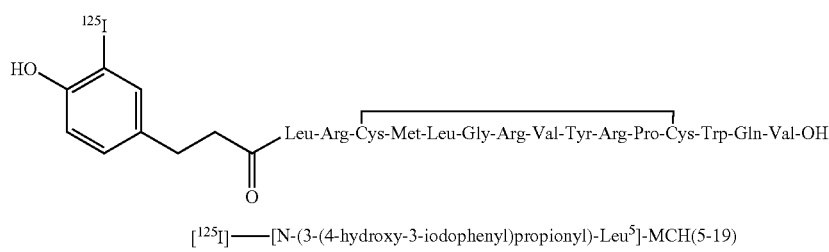
[125I]——[N-(3-(4-hydroxy-3-iodophenyl)propionyl)-Leu⁵]-MCH(5-19)
(6)
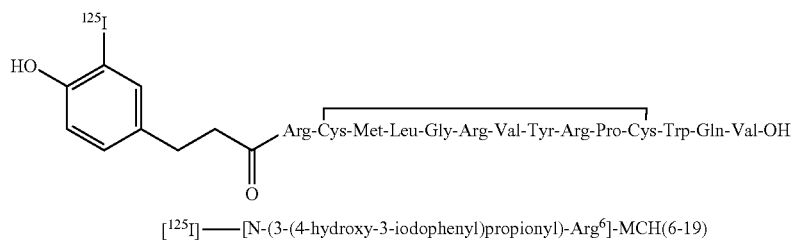
[125I]——[N-(3-(4-hydroxy-3-iodophenyl)propionyl)-Arg⁶]-MCH(6-19)
(7)
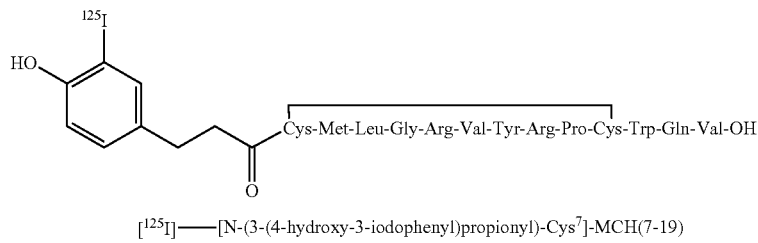
[125I]——[N-(3-(4-hydroxy-3-iodophenyl)propionyl)-Cys⁷]-MCH(7-19)

Among them, in particular,

[$^{125}$I]-[N-(3-(4-hydroxy-3-iodophenyl)propionyl)-Met$^4$]-MCH(4-19) is preferred.

A salt of MCH or its derivatives includes the same salt form as described on salts of SLT, SLC-1 and MCH mentioned above.

Partial peptides of SLT and/or SLC-1 used in the present invention (hereinafter sometimes referred to as the partial peptides) may be any of partial peptides composing the above-mentioned SLT and/or SLC-1, and include a part of SLT and/or SLC-1 which is exposed to the outside of cell membrane and retains a receptor binding activity.

Specifically, a peptide containing a part found to be an extracellular domain (hydrophilic domain) by the hydrophobic plotting analysis in SLT and/or SLC-1 can be used. Such a peptide may also contain a hydrophobic domain in part. Such a peptide may contain a single domain or plural domains together.

The partial peptides of SLT and/or SLC-1 contain at least 20, preferably at least 50, and more preferably at least 100 amino acids of the amino acid sequence which constitutes SLT and/or SLC-1.

The partial peptides of SLT and/or SLC-1 may include ones wherein one or more (preferably about 1 to 10, more preferably several (1 or 2)) amino acids of the amino acid sequence of SLT and/or SLC-1 are deleted, one or more (preferably about 1 to 20, more preferably about 1 to 10, even more preferably several (1 or 2)) amino acids are added to the amino acid sequence, and one or more (preferably about 1 to 10, more preferably about 1 to 5, even more preferably several (1 or 2)) amino acids of the amino acid sequence are substituted with other amino acids.

Hereinafter, SLT and a partial peptide thereof may be referred to simply as SLT. SLC-1 and a partial peptide thereof may be referred to simply as SLC-1.

The DNA encoding SLT used in the present invention may be any DNA comprising a DNA having the nucleotide sequence encoding a protein comprising the same or substantially the same amino acid sequence as that shown by SEQ ID NO: 3. The DNA encoding SLC-1 used in the present invention may be any DNA comprising a DNA having the nucleotide sequence encoding a protein comprising the same or substantially the same amino acid sequence as that shown by SEQ ID NO: 16 or NO: 17. The DNA encoding MCH used in the present invention may be any DNA comprising a DNA having the nucleotide sequence encoding a peptide comprising the same or substantially the same amino acid sequence as that shown by SEQ ID NO: 6. These DNAs may be derived from any of genomic DNA, genomic DNA library, cDNA derived from the cells and tissues described above, cDNA library derived from the cells and tissues described above, and synthetic DNA. Vectors to be used for the library may be any of bacteriophage, plasmid, cosmid and phagemid. The DNAs may also be directly amplified by reverse transcriptase polymerase chain reaction (RT-PCR) using a total RNA fraction prepared from the cells and tissues described above.

More Specifically, used are (1) a DNA hybridizing under high stringent conditions with a DNA sequence comprising a DNA sequence encoding a protein or peptide comprising the same or substantially the same amino acid sequence as that shown by SEQ ID NO: 3, NO: 16, NO: 17, or NO: 6; (2) a DNA which does not hybridize with the DNA sequence comprising a DNA sequence encoding the protein or peptide comprising the same or substantially the same amino acid sequence as that shown by SEQ ID NO: 3, NO: 16, NO: 17, or NO: 6, and the DNA sequence defined in (1) due to degeneracy of genetic code, but which encodes the protein or peptide. Hybridization can be carried out according to a known method or a modified method thereof. The high stringent conditions used herein refer to the conditions, for example, 50% formaldehyde, 4×SSPE (1×SSPE=150 mM NaCl, 10 mM NaH$_2$PO$_4$/H$_2$O, 1 mM EDTA, pH7.4), 5×Denhardt's solution and 0.1% of SDS at a temperature of 42° C.

An example of the DNA encoding SLT, or the DNA comprising a DNA having the nucleotide sequence encoding a protein comprising the same or substantially the same amino acid sequence as that shown by SEQ ID NO: 3 includes a DNA comprising a DNA having the nucleotide sequence shown by SEQ ID NO: 9.

An example of the DNA encoding SLC-1, or the DNA comprising a DNA having the nucleotide sequence encoding a protein comprising the same or substantially the same amino acid sequence as that shown by SEQ ID NO: 16 or NO: 17 includes a DNA comprising a DNA having the nucleotide sequence shown by SEQ ID NO: 18 or NO: 19.

An example of the DNA encoding MCH includes the DNA comprising a DNA having the nucleotide sequence encoding a peptide comprising the same or substantially the same amino acid sequence as that shown by SEQ ID NO: 6.

The DNAs encoding SLT, SLC-1 and MCH used in the present invention can be produced according to a genetic engineering method described below.

For cloning the DNA fully encoding SLT, SLC-1 or MCH of the present invention, the desired DNA may be amplified by the known PCR method using synthetic DNA primers having a part of the nucleotide sequence encoding SLT, SLC-1 or MCH from the above-mentioned DNA library. Alternatively, the DNA inserted into an appropriate vector can be selected by hybridization with a labeled DNA fragment or synthetic DNA having a part or whole of the nucleotide sequence encoding SLT, SLC-1 or MCH. The hybridization can be carried out, for example, according to the method described in Molecular Cloning, 2nd, J. Sambrook et al., Cold Spring Harbor Lab. Press, 1989. The hybridization may also be performed using commercially available library in accordance with the protocol described in the attached instructions.

The cloned DNA encoding SLT, SLC-1 or MCH used in the present invention can be used depending upon purpose, as it is or if desired, after digestion with a restriction enzyme or after addition of a linker thereto. The DNA may contain ATG as a translation initiation codon at the 5' end thereof and may further contain TAA, TGA or TAG as a translation termination codon at the 3' end thereof. These translation initiation and termination codons can also be added using an appropriate synthetic DNA adapter.

The expression vector for SLT, SLC-1 or MCH used in the present invention can be produced, for example, by (a) excising the desired DNA fragment from the DNA encoding SLT, SLC-1 or MCH used in the present invention, and then (b) ligating the DNA fragment into an appropriate expression vector downstream of a promoter.

Examples of the vector include plasmids derived form *E. coli* (e.g. pBR322, pBR325, pUC12, pUC13), plasmids derived from Bacillus subtilis (e.g. pUB110, pTP5, pCl94), plasmids derived from yeast (e.g. pSH19, pSH15), bacteriophages such as λ phage, etc., animal viruses such as retrovirus, vaccinia virus, baculovirus, etc. The promoter used in the present invention may be any promoter suitable for a host to be used for gene expression.

When the host for transformation is animal cells, SV40 promoter, a retrovirus promoter, a metallothionein promoter, a heat shock promoter, a cytomegalovirus promoter, SRα promoter, etc can be used. When the host is *Escherichia* bacteria, preferred are trp promoter, T7 promoter, lac promoter, recA promoter, $\lambda P_L$ promoter, lpp promoter, etc. When the host is *Bacillus* bacteria, preferred are SPO1 promoter, SPO2 promoter and penP promoter, etc. When the host is yeast, preferred are PHO5 promoter, PGK promoter, GAP promoter and ADH1 promoter, GAL promoter, etc. When the host is insect cells, preferred are polyhedrin prompter and P10 promoter, etc.

In addition, the expression vector may further optionally contain an enhancer, a splicing signal, a poly-A addition signal, a selection marker, SV40 replication origin (hereinafter sometimes abbreviated as SV40ori), etc. Examples of the selection marker include dihydrofolate reductase gene (hereinafter sometimes abbreviated as dhfr) [methotrexate (MTX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker in CHO(dhfr⁻) cell, selection can also be carried out in a thymidine-free medium.

If necessary, a signal sequence suitable for a host is added to the N-terminal of the polypeptide or the partial peptide. Examples of the signal sequence that can be used are Pho A signal sequence, OmpA signal sequence, etc. for an *Escherichia* bacterium host; α-amylase signal sequence, subtilisin signal sequence, etc. for a *Bacillus* bacterium host; MF-α signal sequence, invertase signal sequence, etc. for a yeast host; and insulin signal sequence, α-interferon signal sequence, antibody molecule signal sequence, etc. for an animal cell host.

Using the vector containing the DNA encoding SLT, SLC-1 or MCH thus constructed, a transformant can be produced.

Examples of the host which may be employed, are *Escherichia* bacteria, *Bacillus* bacteria, yeast, insect cells, insects and animal cells, etc.

Examples of the *Escherichia* bacteria include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of the *Bacillus* bacteria include *Bacillus subtilis* MI114 (Gene, 24, 255 (1983)), 207-21 (Journal of Biochemistry, 95, 87 (1984)), etc.

Examples of yeast include *Saccharomyces cereviseae* AH22, AH22R⁻, NA87-11A, DKD-5D, 20B-12, etc.

Examples of insect include a larva of *Bombyx mori* (Maeda, et al., Nature, 315, 592 (1985)).

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc.; and for the virus BmNPV, *Bombyx mori* N cells (BmN cells), etc. Examples of the Sf cell which can be used are Sf9 cells (ATCC CRL1711) and Sf21 cells (both cells are described in Vaughn, J. L. et al., In Vitro, 13, 213-217 (1977).

Examples of animal cells include monkey cells COS-7, Vero cells, Chinese hamster cells CHO (hereinafter referred to as CHO cells), dhfr gene deficient Chinese hamster cells CHO (hereinafter simply referred to as CHO(dhfr⁻) cell), mouse L cells, mouse 3T3, mouse myeloma cells, human HEK293 cells, human FL cells, 293 cells, C127 cells, BALB3T3 cells, Sp-2/O cells, etc.

*Escherichia* bacteria can be transformed, for example, by the method described in Proc. Natl. Acad. Sci. U.S.A., 69, 2110 (1972) or Gene, 17, 107 (1982).

Bacillus bacteria can be transformed, for example, by the method described in Molecular & General Genetics, 168, 111 (1979).

Yeast can be transformed, for example, by the method described in Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in Virology, 52, 456 (1973).

The method of introducing the expression vector into the cells includes, for example, lipofection (Felgner, P. L. et al. Proc. Natl. Acad. Sci. U.S.A., 84, 7413 (1987)), calcium phosphate method (Graham, F. L. and van der Eb, A. J. Virology, 52, 456-467 (1973)), electroporation (Nuemann, E. et al. Embo J., 1, 841-845 (1982)), etc.

Thus, the transformant transformed with the expression vector containing the DNA encoding SLT, SLC-1 or MCH used in the present invention can be obtained.

Furthermore, to express SLT, SLC-1 or MCH used in the present invention in a stable manner using animal cells, the animal cell clone can be selected, the chromosome of which the introduced expression vector is incorporated into. To be more specific, using the above selection marker as an index, a transformant can be selected. From these animal cells obtained by use of the selection marker, it is possible to obtain a stable animal cell strain having a highly expressed SLT, SLC-1 or MCH used in the present invention by repeating the clonal selection. Moreover, when using dhfr gene as a selection marker, the cells are cultured in gradually increased concentrations of MTX, and the resistant cell strain is selected. In this way, it is possible to obtain the highly expression animal cell strain by amplifying the DNA encoding SLT, SLC-1 or MCH as well as dhfr gene in the cell.

SLT, SLC-1 or MCH used in the present invention can be produced by cultivating the above-mentioned transformant under condition allowing the expression of the DNA encoding SLT, SLC-1 or MCH used in the present invention; and producing and accumulating SLT, SLC-1 or MCH used in the present invention.

When the host is Escherichia or Bacillus bacteria, the transformant can be appropriately cultured in a liquid medium, which contains materials required for growth of the transformant, such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may be added to the medium. Preferably, pH of the medium is about 5 to 8.

A preferred example of the medium for culturing *Escherichia* bacteria is M9 medium supplemented with glucose and Casamino acids (Miller, Journal of Experiments in Molecular Genetics, 431-433, Cold Spring Harbor Laboratory, New York, 1972). If necessary, a chemical such as 3β-indolylacrylic acid can be added to the medium to work the promoter efficiently.

When the host is *Escherichia* bacteria, the transformant is usually cultivated at about 15° C. to 43° C. for about 3 to 24 hours. If necessary, the culture may be aerated or agitated.

When the host is *Bacillus* bacteria, the transformant is cultivated generally at about 30° C. to 40° C. for about 6 to 24 hours. If necessary, the culture can be aerated or agitated.

When the host is yeast, the transformant is cultivated, for example, in Burkholder's minimal medium (Bostian, K. L. et al., Proc. Natl. Acad. Sci. U.S.A., 77, 4505 (1980)) or in SD medium supplemented with 0.5% Casamino acids (Bitter, G. A. et al., Proc. Natl. Acad. Sci. U.S.A., 81, 5330 (1984)). Preferably, pH of the medium is about 5 to 8. In general, the transformant is cultivated at about 20° C. to 35° C. for about 24 to 72 hours. If necessary, the culture can be aerated or agitated.

When the host is insect cells, the transformant is cultivated in, for example, Grace's Insect Medium (Grace, T. C. C., Nature, 195, 788 (1962)) to which an appropriate additive such as 10% inactivated bovine serum is added. Preferably, pH of the medium is about 6.2 to 6.4. Normally, the transformant is cultivated at about 27° C. for about 3 to 5 days and, if necessary, the culture can be aerated or agitated.

When the host is animal cells, the transformant is cultivated in, for example, MEM medium (Science, 122, 501 (1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1 (1950)), which contain about 5% to about 20% fetal bovine serum. Preferably, pH of the medium is about 6 to 8. The transformant is usually cultivated at about 30° C. to 40° C. for about 15 to 60 hours and, if necessary, the culture can be aerated or agitated.

When using CHO(dhfr$^-$)cells and dhfr gene as a selection marker, a thymidine-free DMEM medium containing dialyzed fetal bovine serum- is preferred.

SLT, SLC-1 or MCH used in the present invention can be separated and purified from the culture described above by the following procedures.

When SLT, SLC-1 or MCH used in the present invention is extracted from the cultured transformants or cells, after cultivation, the transformants or cells are collected by a well-known method, suspended in a appropriate buffer, and then disrupted by publicly known methods such as ultrasonication, a treatment with lysozyme and/or freeze-thaw cycling. Then by centrifugation, filtration, etc., the crude extract of SLT, SLC-1 or MCH used in the present invention can be obtained. The buffer for the extraction may contain a protein denaturizing agent, such as urea or guanidine hydrochloride, or a surfactant, such as Triton X-100™, etc.

When SLT, SLC-1 or MCH used in the present invention is secreted to the culture medium, after the cultivation, the transformants or cells can be separated to collect the supernatant by a well-known method.

SLT, SLC-1 or MCH present in the supernatant or the extract thus obtained can be purified by an appropriate combination of well-known methods for separation and purification. Such publicly known methods for separation and purification include a method utilizing difference in solubility such as salting out, solvent precipitation, etc.; a method utilizing difference mainly in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing, chromatofocusing; and the like.

When SLT, SLC-1 or MCH used in the present invention is obtained in a free form, it can be converted into a salt form by well-known methods or modifications thereof. On the other hand, when SLT, SLC-1 or MCH is obtained in a salt form, it can be converted into the free form or another salt form by well-known methods or modifications thereof.

SLT, SLC-1 or MCH used in the present invention produced by a recombinant can be treated, before or after the purification, with an appropriate protein modifying enzyme so that SLT, SLC-1 or MCH can be appropriately modified or be deprived of a partial (poly)peptide. Examples of the protein-modifying enzyme include trypsin, chymotrypsin, arginyl endopeptidase, protein kinase, glycosidase or the like. It is possible to use the well-known Edman method using Edman reagent (phenyl iso-thiocyanate) to delete the N-terminal amino acid.

The presence of the thus produced SLT, SLC-1 or MCH used in the present invention can be determined by an enzyme immunoassay using an antibody specific thereto, or the like.

The screening method for a compound or its salt that alters the binding property of MCH or a salt thereof to SLT or a salt thereof, characterized by using MCH, a derivative or a salt thereof and SLT or a salt thereof, and the screening kit for a compound or its salt that alters the binding property of MCH or a salt thereof to SLT or a salt thereof, characterized by comprising MCH, a labeled form or a salt thereof and SLT or a salt thereof, are described in detail below.

Using the binding assay system of SLT or a salt thereof (ligand/receptor assay system), or of the constructed recombinant SLT expression system, to MCH, a derivative or a salt thereof, a compound or a salt thereof that alters the binding property of MCH or a salt thereof to SLT or a salt thereof (e.g., peptides, proteins, non-peptide compounds, synthetic compounds, fermentation products, etc.) can be screened.

The compounds include a compound (SLT (MCH receptor) agonist) having SLT-mediated cell-stimulating activities (e.g., activities of enhancing or inhibiting arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation and pH decrease), and a compound (SLT (MCH receptor) antagonist) having no such cell-stimulating activities. The wording "alter the binding property of MCH or a salt thereof to SLT or a salt thereof" means either of properties of inhibiting or enhancing the binding of MCH or a salt thereof to SLT or a salt thereof.

Thus, the present invention provides a method for screening a compound or a salt thereof that alters the binding property of MCH or a salt thereof to SLT or a salt thereof, characterized by comparing (i) a case where MCH, a derivative or a salt thereof is brought in contact with SLT or a salt thereof and (ii) a case where MCH, a derivative or a salt thereof and a test compound are brought in contact with SLT or a salt thereof.

In the screening method of the present invention, for example, a binding amount of the ligand to SLT or a salt thereof, a level of cell-stimulating activity, and the like are measured and compared in (i) a case where MCH, a derivative or a salt thereof is brought in contact with SLT or a salt thereof and (ii) a case where MCH, a derivative or a salt thereof and a test compound are brought in contact with SLT or a salt thereof.

Specifically, the screening method of the present invention includes:

(1) A method for screening a compound or a salt thereof that alters the binding property of MCH or a salt thereof to SLT or a salt thereof, which comprises measuring and comparing the binding amounts of a labeled form of MCH, a derivative or a salt thereof ("a derivative of MCH or a salt thereof" needs to be no longer labeled if it refers to "a labeled MCH or a salt thereof" by itself.) to SLT or a salt thereof in a case where a labeled form of MCH, a derivative or a salt thereof is brought in contact with SLT or a salt thereof and a case where a labeled form of MCH, a derivative or a salt thereof and a test compound are brought in contact with SLT or a salt thereof;

(2) A method for screening a compound or a salt thereof that alters the binding property of MCH or a salt thereof to SLT, which comprises measuring and comparing the binding amounts of a labeled form of MCH, a derivative or a salt thereof to a cell containing SLT or a membrane fraction of the cell in a case where a labeled form of MCH, a derivative or a salt thereof is brought in contact with the cell containing SLT or membrane fraction thereof and a case where a labeled form of MCH, a derivative or a salt thereof and a test compound are brought in contact with the cell containing SLT or membrane fraction thereof;

(3) A method for screening a compound or a salt thereof that alters the binding property of MCH or a salt thereof to SLT, which comprises measuring and comparing the binding amounts of a labeled form of MCH, a derivative or a salt thereof to SLT in a case where a labeled form of MCH, a derivative or a salt thereof is brought in contact with SLT expressed on cell membrane of a cultured transformant containing a DNA encoding SLT and a case where a labeled form of MCH, a derivative or a salt thereof and a test compound are brought in contact with SLT expressed on cell membrane of a cultured transformant containing a DNA encoding SLT;

(4) A method for screening a compound or a salt thereof that alters the binding property of MCH or a salt thereof to SLT, which comprises measuring and comparing SLT-mediated cell-stimulating activities (e.g., activities of enhancing or inhibiting arachidonic acid release, acetylcholine release, intracellular $Ca^{2+}$ release, intracellular cAMP production, intracellular cGMP production, inositol phosphate production, change in cell membrane potential, phosphorylation of intracellular proteins, c-fos activation and pH decrease) in a case where a compound which activates SLT (e.g. MCH, a derivative or a salt thereof) is brought in contact with a cell containing SLT and a case where a compound which activates SLT and a test compound are brought in contact with the cell containing SLT; and (5) A method for screening a compound or a salt thereof that alters the binding property of MCH or a salt thereof to SLT, which comprises measuring and comparing SLT-mediated cell-stimulating activities (e.g., activities of enhancing or inhibiting arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation and pH decrease) in a case where a compound which activates SLT (e.g. MCH, a derivative or a salt thereof) is brought in contact with SLT expressed on cell membrane of a cultured transformant containing a DNA encoding SLT and a case where a compound which activates SLT and a test compound are brought in contact with SLT expressed on the cell membrane of cultured transformant containing a DNA encoding SLT.

The specific description of the screening methods of the present invention is as follows.

SLT used in the screening method of the present invention may be any substance which contains the above-mentioned SLT. Because human organs in particular are very difficult to obtain, it is preferable to use SLT produced by a recombinant in a large scale.

The above-mentioned methods may be employed to produce SLT.

In the screening method of the present invention, the cell containing SLT or the cell membrane fraction thereof can be prepared according to the preparation method described below.

When the cells containing SLT are used, the cells may be fixed using glutaraldehyde, formalin, etc. The fixation can be made by a well-known method.

The cells containing SLT include host cells that express SLT. Such host cells include *Escherichia coli*, *Bacillus subtilis*, yeast, insect cells, animal cells, and the like, as described above.

The cell membrane fraction refers to a fraction abundant in cell membrane, obtained by cell disruption and subsequent fractionation by a well-known method. The cell disruption methods include cell squashing using a Potter-Elvehjem homogenizer, disruption using a Waring blender or Polytron (produced by Kinematica Inc.), disruption by ultrasonication, and disruption by cell spraying through thin nozzles under an increased pressure using a French press or the like. Fractionation of cell membrane is carried out mainly by fractionation method using a centrifugal force, such as centrifugal fractionation or density gradient centrifugation. For example, after the disrupted cell solution is centrifuged at a low speed (500 rpm to 3,000 rpm) for a short period (normally about 1 to 10 minutes), the resulting supernatant is centrifuged at a higher speed (15,000 rpm to 30,000 rpm) normally for 30 minutes to 2 hours. The precipitate thus obtained is used as the membrane fraction. The membrane fraction is rich in expressed SLT and also membrane components, such as cell-derived phospholipids and membrane proteins.

The amount of SLT in the cell containing SLT and in the membrane fraction is preferably $10^3$ to $10^8$ molecules per cell, more preferably $10^5$ to $10^7$ molecules per cell. As the amount of expressed SLT increases, the ligand binding activity per unit of membrane fraction (specific activity) increases so that not only the highly sensitive screening system can be constructed but also large quantities of samples can be assayed with the same lot.

To perform the methods (1) through (3) described above for screening a compound that alters the binding property of MCH or a salt thereof to SLT, an appropriate SLT fraction and a labeled form of a ligand or a compound having a ligand activity (MCH or a derivative thereof) are used. SLT fraction is preferably a fraction of a naturally occurring SLT or a recombinant SLT having an activity equivalent to that of the natural protein. Herein, the equivalent activity is intended to mean a ligand binding activity. The labeled form of a ligand or a compound having a ligand activity includes a labeled form of MCH or a derivative thereof. For example, a ligand (MCH or a derivative thereof) labeled with [$^3$H], [$^{125}$I], [$^{14}$C], [$^{35}$S], etc. can be used. In particular, the labeled form of MCH or a derivative thereof, which is prepared using Bolton-Hunter reagent according to a known method, may also be used.

Examples of the labeled MCH derivative include the compounds (1) to (7) described above.

More specifically, to perform the screening for a compound that alters the binding property of MCH or a salt thereof to SLT, first, a receptor preparation is prepared by suspending cells containing SLT or the membrane fraction thereof in a buffer appropriate for the screening method. Any buffer can be used so long as it does not inhibit the ligand-receptor binding, such buffers including a phosphate buffer or a Tris-HCl buffer having pH of 4 to 10 (preferably pH of 6 to 8). For the purpose of minimizing non-specific binding, a surfactant such as CHAPS, Tween-80™ (Kao-Atlas Inc.), digitonin or deoxycholate, may optionally be added to the buffer. Further for the purpose of suppressing the degradation of SLT and MCH or a derivative thereof by proteases, a protease inhibitor such as PMSF, leupeptin, E-64 (Peptide Institute, Inc.) and pepstatin may also be added. A given amount (5,000 to 500,000 cpm) of labeled form of MCH or a derivative thereof is added to 0.01 ml to 10 ml of the receptor solution. Also, $10^{-4}$ to $10^{-1}$ μM of the test compound are added to the mixture. To determine the amount of non-specific binding (NSB), a reaction tube containing an excessive amount of unlabeled MCH or a derivative thereof is also prepared. The reaction is carried out at approximately 0 to 50° C., preferably 4 to 37° C. for 20 minutes to 24 hours, preferably 30 minutes to 3 hours. After completion of the reaction, the reaction mixture is filtrated through glass fiber filter paper, etc. and washed with an appropriate volume of the buffer. The residual radioactivity on the glass fiber filter paper is then measured with a liquid scintillation counter or γ-counter. Taking $B_0$-NSB (the count obtained by subtracting the amount of non-specific binding (NSB) from the count in the absence of an antagonistic substance ($B_0$)) as 100%, if a test compound makes the specific binding amount (B-NSB), for example, to 50% or less, it can be selected as a candidate substance having an antagonistic activity.

For measuring the binding of SLT to MCH or a derivative thereof, BIAcore (Amasham pharmacia Biotech) may be used. In this method, MCH or a derivative thereof is fixed to a sensor chip according to the amino coupling method described in the protocol attached to the device. A buffer (such as phosphate buffer and Tris buffer) solution containing SLT purified from the cells containing SLT or a transformant having the DNA encoding SLT, or a membrane fraction having SLT, or a buffer solution containing the purified SLT or the membrane fraction having SLT and a test compound is run on the top of the sensor chip at 2-20 μl/min. By investigating whether the co-existing test compound can alter the surface plasmo resonance change which is induced by the binding of SLT with MCH or a derivative thereof on the sensor chip, a compound that alters the binding property of SLT to MCH can be screened. This method can also be carried out by fixing SLT on the sensor chip and running a buffer solution (such as phosphate buffer or Tris buffer) containing MCH or a derivative thereof, or a buffer solution containing MCH or a derivative thereof and a test compound on the top of the sensor chip. The test compounds are as described above.

To perform the above methods (4) and (5) for screening a compound that alters the binding property of MCH or a salt thereof to SLT or a salt thereof, SLT-mediated cell-stimulating activity (e.g., activities of promoting or inhibiting arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation, pH decrease, etc.) can be measured using a known method or a commercially available measuring kit. Specifically, at first, cells containing SLT are cultured on a multi-well plate. For the screening, the medium is replaced with a fresh medium or with an appropriate non-cytotoxic buffer, followed by incubation for a given period of time in the presence of a test compound. Subsequently, the resulting product is quantified by appropriate procedures in the cell extract or the supernatant. When it is difficult to detect the production of the index substance (e.g., arachidonic acid) for the cell-stimulating activity, due to the presence of a degrading enzyme in the cells, an inhibitor of the degrading enzyme may be added before the assay. For detecting an inhibitory activity, such as the inhibition of cAMP production, the basic production in the cells can be increased by forskolin or the like and then the inhibitory effect on the increased basic production can be detected.

The screening by assaying the cell-stimulating activity requires an appropriate cell expressing SLT. For the cells expressing SLT, the recombinant cells-expressing the SLT described above and the like are desirable. The transformed cells capable of expressing SLT may be either a stable expression strain or a transient expression strain. The types of animal cells used are as described above.

For test compounds, for example, peptides, proteins, non-peptide compounds, synthetic compounds, fermentation products, cell extracts, plant extracts, and animal tissue extracts may be used.

To describe the above-mentioned ligand/receptor assay more specifically, the following assay systems are used.

[1] When a receptor-expressing cell is stimulated by a receptor agonist, an intracellular G-protein becomes active and, as a result, GTP bonds with it. The same phenomena can be observed with a cell membrane of receptor expression cell. Generally, GTP is converted to GDP by hydrolysis. When GTPγS is added to the reaction solution, GTPγS bonds with G-protein as GTP does, and it does not suffer from hydrolysis with keeping the binding to the cell membrane containing the G-protein. Using the labeled GTPγS, it is possible to determine the activity of the receptor agonist to stimulate the receptor-expressing cell by measuring the radioactivity remaining in the cell membrane. Applying this reaction, a stimulating activity of MCH or a derivative thereof to SLT-expressing cells can be measured. This method does not use the cells containing SLT as described above (4)-(5). This method is an assay using the cell membrane containing SLT as described in (1)-(3), and is an assay to measure a cell stimulating activity as described in (4)-(5). In this assay, a substance which shows an activity to promote the binding of GTPγS to SLT-containing cell membrane fraction is an agonist. By adding MCH or a derivative thereof, or adding MCH or a derivative thereof and a test compound; and observing the change in the acceleration activity of GTPγS binding to an SLT-containing cell membrane fraction as compared with a single administration of MCH or a derivative thereof, a compound that alters the binding property of MCH to SLT can be screened. A compound which shows the activity to inhibit the acceleration activity of GTPγS binding to an SLT-containing cell membrane fraction by MCH or a derivative thereof can be selected as a candidate substance having an antagonistic activity. On the other hand, an agonist can be screened by adding a test compound alone and observing the acceleration activity of GTPγS binding to an SLT-containing cell membrane fraction as well.

Specifically, an example of the screening methods is described as follows. A cell membrane fraction containing SLT prepared by the method described above is diluted with a membrane dilution buffer solution (e.g. 50 mM Tris, 5 mM $MgCl_2$, 150 mM NaCl, 1 µM GDP, 0.1% BSA pH7.4). The dilution scale may vary according to the amount of receptor expression. 0.2 ml of the solution is transferred to Falcon 2053. MCH or a derivative thereof is added, or MCH or a derivative thereof and a test compound are added thereto, and then [$^{35}$S]GTPγS is added to make the final concentration of 200 pM. After the mixture is kept at 25° C. for an hour, an ice-cold buffer solution for washing (50 mM Tris, 5 mM $MgCl_2$, 150 mM NaCl, 0.1% BSA, 0.05% CHAPS pH7.4 1.5 ml) is added. Then, the solution is filtered with a glass fiber filtering paper GF/F. After drying the filtering paper at 65° C. for 30 min., the radioactivity of [$^{35}$S]GTPγS bound with the membrane fraction left on the filtering paper is measured on a liquid scintillation counter. The radioactivity in the experiment with a single administration of MCH or a derivative thereof is set as 100%, the radioactivity in the experiment without adding MCH or a derivative thereof is set as 0%, and an influence of a test compound on the acceleration activity of GTPγS binding by MCH or a derivative thereof is calculated. A test compound which makes the acceleration activity of GTPγS binding, for example 50% or less, can be selected as a candidate substance having an antagonistic activity.

[2] The amount of intracellular cAMP is reduced by the MCH stimulation in an SLT-expressing cell. Using this reaction, the cell stimulating activities of MCH to an SLT-expressing cell can be measured.

Using the anti-cAMP antibody obtained by immunized mice, rats, rabbits, goats and cows and $^{125}$I-labeled cAMP (both are commercially available), the amount of cAMP production in various animal cells expressing SLT can be measured by RIA or other EIA system such as the combination of anti-cAMP antibody and the labeled cAMP. It is also possible to conduct a quantification by the SPA method using beads containing the scintillant to which an anti-cAMP is fixed using Protein A or an antibody to IgG of an animal used for production of the anti-cAMP antibody, and $^{125}$I-labeled cAMP (using the kit produced by Amasham pharmacia Biotech).

The assay for inhibition of cAMP production is carried out using the method described in Example 5 or the modified method thereof. In this assay system, it is possible to conduct the screening of a compound that alters the binding property of MCH to SLT by increasing the amount of intracellular cAMP by ligand such as Calcitonin and Forskolin which increase the amount of intracellular cAMP; adding MCH or a derivative thereof, or adding MCH or a derivative thereof and a test compound; and observing the change in the amount of intracellular cAMP as compared to the case with a single administration of MCH or a derivative thereof. Then, a compound that shows an inhibitory activity on the cAMP production inhibition induced by MCH or a derivative thereof in the SLT-expressing cells can be selected as a candidate substance having an antagonistic activity. On the other hand, a compound that shows an agonist activity can be screened by adding a test compound alone and measuring the activity of cAMP production inhibition.

More specifically, the screening methods are described as follows. SLT-expressing CHO (CHO/SLT) cells are plated at $5\times10^4$ cells/well on a 24-well plate, and cultivated for about 48 hours. The cells are washed with Hanks' buffer containing 0.2 mM 3-isobutyl-methylxanthine, 0.05% BSA and 20 mM HEPES (pH7.4)(hereinafter referred to as reaction buffer). Then, 0.5 ml of the reaction buffer is added to the cells, and the cells are kept in an incubator for 30 minutes. Then, the reaction buffer is removed and 0.25 ml of fresh reaction buffer is added to the cells. Then, the reaction buffer (0.25 ml) containing 2 µM Forskolin with 1 nM of MCH or a derivative thereof, or with 1 nM of MCH or a derivative thereof and a test compound is added to the cells. The reaction is made at 37° C. for 24 minutes. 100 µl of 20% Perchloric acid is added to stop the reaction. Then, by placing it on ice, the intracellular cAMP is extracted. The amount of cAMP in the extraction is measured by using cAMP EIA kit (Amasham pharmacia biotech). The amount of cAMP produced by the Forskolin stimulation is set as 100%, the amount of cAMP inhibited by the addition of 1 nM of MCH or a derivative thereof is set as 0% and an influence of a test compound on the activity of cAMP production inhibition by MCH or a derivative thereof is calculated. A test compound which makes the cAMP production activity, for example, 50% or more by inhibiting the activity of the MCH or a derivative thereof can be selected as a candidate substance having an antagonistic activity.

To measure the activity to promote the cAMP production, cAMP produced by adding a test compound to the CHO/SLT cells without added Forskolin is measured according to the above-mentioned method.

[3] The DNA containing CRE (cAMP response element) is inserted into the multi-cloning site upstream of luciferase gene of Picagene basic vector or Picagene enhancer vector (Toyo Ink). It is named as CRE-reporter gene vector. In the cell transfected with the CRE-reporter gene vector, a stimulation which causes the increase in cAMP, induces an expression of luciferase gene through CRE and a production of luciferase protein. By measuring the luciferase activity, it is possible to detect the change in the amount of cAMP in the cells into which the CRE-reporter gene vector is introduced. Thus, a compound that alters the binding property of MCH to SLT can be screened using the SLT-expressing cells to which the CRE-reporter gene vector is transfected. The details of the screening method are as follows.

CRE-reporter gene introduced SLT-expressing cells is placed in a 24-well plate at a concentration of $5\times10^3$ cells/well, and cultivated for about 48 hours. The cells are washed with Hanks' buffer (pH7.4) containing 0.2 mM 3-isobutyl-methyl xanthine, 0.05% BSA and 20 mM HEPES (hereinafter, Hanks' buffer(pH7.4) containing 0.2 mM 3-isobutyl-methyl xanthine, 0.05% BSA and 20 mM HEPES, is referred to as reaction buffer). 0.5 ml of the reaction buffer is added to the cells. Then, the cells are kept warm in a cultivator for 30 minutes. Then, the reaction buffer is removed from the system. 0.25 ml of fresh reaction buffer is added to the cells. Then, the reaction buffer 0.25 ml containing 2 µM Forskolin with 1 nM of MCH or a derivative thereof, or with 1 nM of MCH or a derivative thereof and a test compound is added to the cells. The reaction is made at 37° C. for 24 minutes. The cells are dissolved in a decomposition solution for Picagene (Toyo Ink). To the decomposition solution, a luminescent substance (Toyo Ink) is added. The luminescence by luciferases is measured with a luminometer, a liquid scintillation counter, a top counter or the like. An influence of a compound that alters the binding property of MCH to SLT can be measured by comparing the luminescence by luciferases with the case where MCH or a derivative thereof is singly administrated. In this process, by administrating MCH or a derivative thereof, the increase of luminescence by the Folskolin stimulation is inhibited. A compound that recovers the inhibition may be selected as a candidate substance having an antagonistic activity. On the other hand, an agonist can be screened by adding a test compound alone and observing the inhibition of increase in luminescence caused by the Folskolin stimulation, as MCH or a derivative thereof inhibits the increase.

Alkaline phosphatase, chloramphenicol, acetyltransferase or β-galactosidase can be used as a reporter gene, besides luciferase. The activity of the product of reporter gene can be measured easily using commercially available measuring kit. The activity of alkaline phosphatase can be measured by Lumi-Phos 530(Wako); the activity of Chloramphenicol and acetyltransferase can be measured by FAST CAT chrolamphenicol Acetyltransferase Assay Kit (Wako); and the activity of β-galactosidase can be measured by Aurora Gal-XE (Wako).

[4] When SLT-expressing cells release the metabolic substance of arachidonic acid to the outside by the MCH stimulation, if arachidonic acid having radioactivity is taken into the cell beforehand, it is possible to measure a cell-stimulating activity by measuring the radioactivity released out of the cells. The measurement is carried out using the method described in Example 9 or the modified method thereof. In this process, by adding MCH or a derivative thereof, or adding MCH or a derivative thereof and a test compound and examining an influence of MCH or a derivative thereof on the activity to release arachidonic acid metabolite, a compound that has the influence on the binding of MCH to SLT can be screened. A compound that inhibits the activity to release arachidonic acid metabolite of MCH or a derivative thereof can be selected as a candidate substance having an antagonistic activity. Moreover, a compound that indicates an agonist activity can be screened by adding a test compound alone and investigating the activity to release arachidonic acid metabolites in SLT-expressing cells using the method described in Example 9 or the modified method thereof. The details of the screening method of a compound that has the influence on the binding of MCH to SLT are as follows.

CHO/SLT cells are placed at $5 \times 10^4$ cells/well on a 24-well plate, and cultivated for about 24 hours. After cultivation, 0.25 μCi/well of [$^3$H] arachidonic acid is added. 16 hours after adding [$^3$H] arachidonic acid, the cells are washed with Hanks' buffer (pH7.4) containing 0.05% BSA and 20 mM HEPES. Then, 500 μl of the Hanks' buffer (pH7.4) containing 0.05% BSA and 20 mM HEPES in the presence of the final concentration of 10 nM MCH or a derivative thereof, or of 10 nM MCH or a derivative thereof and a test compound is added to each well (hereinafter, Hanks' buffer (pH7.4) containing 0.05% BSA and 20 mM HEPES is referred to as reaction buffer). After incubating at 37° C. for 60 minutes, 400 μl of the reaction solution is added to a scintillator. Then, the amount of released [$^3$H] arachidonic acid metabolite is measured by a scintilation counter. The amount of [$^3$H] arachidonic acid metabolite in the medium without added MCH or a derivative thereof is set as 0%, the amount of [$^3$H] arachidonic acid metabolite in the medium with added 10 nM MCH or a derivative thereof is set as 100%, and an influence of a test compound on the binding of MCH or a derivative thereof to SLT is calculated. A test compound which makes the activity of arachidonic acid metabolite production, for example, 50% or less, can be selected as a candidate substance having an antagonistic activity.

[5] Stimulation by MCH causes the increase in intracellular $Ca^{2+}$ concentration in SLT-expressing cells. Using this fact, an influence of test compound on the binding of MCH to SLT can be examined, specifically using the method described in Example 8 or the modified method thereof.

SLT-expressing cells are placed on a sterilized cover glass for a microscope. After 2 days, the medium is replaced with HBSS in which 4 mM of Fura-2 AM (Dojin Kagaku) is suspended, and left for 2 and half hours at room temperature. After washing with HBSS, the cover glass is set to a cuvet. The increase in the ratio of intensity of fluorescence at 505 nm where the excited wave length is 340 nm and 380 nm, is measured by a spectrophotofluorometer when MCH or a derivative thereof is added, or MCH or a derivative thereof and a test compound are added. By measuring the change in the intensity of fluorescence caused by adding a test compound compared with that by the single administration of MCH or a derivative thereof, a compound which has the influence on the binding of MCH to SLT can be screened. Furthermore, FLIPR (Produced by Molecular device) can be also used as follows. Fluo-3 AM (Produced by Dojin Kagaku) is added to the cell suspension to let the cells take up Fluo-3AM. The cells are washed by centrifuging several times, and placed on a 96-well plate. The cells are set to a FLIPR device, and MCH or a derivative thereof is added, or MCH or a derivative thereof and a test compound are added in the same way as Fura-2AM. By measuring the change in the intensity of fluorescence caused by added a test compound as compared with that by single administration of MCH or a derivative thereof, a compound that has an influence on the binding of MCH or a derivative thereof to SLT can be screened. Above these, a compound that inhibits the increase in the intensity of fluorescence by MCH or a derivative thereof can be selected as a candidate substance having an antagonistic activity. On the other hand, by observing the increase in intensity of fluorescence by single administration of a test compound, an agonist can be screened.

To screen a compound that has an influence on the binding of MCH to SLT, first, SLT-expressing cells are allowed to co-express a gene of a protein such as Aequorin which radiates light when the intracellular Ca ion increases. The increase in the intracellular Ca ion causes Aequorin to become Ca binding type and radiates light. Using this fact, MCH or a derivative thereof is added, or MCH or a derivative thereof and a test compound are added and the change in intensity of luminescence when a test compound is added as compared with that by single administration of MCH or a derivative thereof is observed for the screening. The method is almost the same as the above-mentioned method except that this method does not require cells to take up a fluorescence substance.

[6] By adding an agonist to receptor-expressing cells, the intracellular concentration of inositol triphosphate rises. By observing the reaction in SLT-expressing cells caused by MCH, a compound that has an influence on the binding of MCH to SLT can be screened. Cells are placed in a 24-well plate, and incubated for one day, and incubated for one more day in a medium to which myo-[2-$^3$H]inositol (2.5 μCi/well) is added. After washing well, MCH or a derivative thereof is added, or MCH or a derivative thereof and a test compound are added thereto, and then 10% Perchloric acid is added to stop the reaction. The reaction solution is neutralized with 1.5M KOH and 60 mM HEPES solution, and passed through a column filled with AG1×8 resin (Bio Rad). After washing with 5 mM $Na_2BO_3$ and 60 mM $HCOONH_4$, the radioactivity, which is eluted by 1M $HCOONH_4$ and 0.1M HCOOH, is measured by a liquid scintillation counter. The radioactivity in the medium when MCH or a derivative thereof is not added, is set as 0%, the radioactivity in the medium when MCH or a derivative thereof is added, is set as 100%, and an influence on the binding of MCH or a derivative thereof to SLT can be calculated. A test compound which makes the activity of inositol triphosphate production, for example, 50% or less can be selected as a candidate substance having an antagonistic activity. On the other hand, by observing the increase in the activity of inositol triphosphate production by single administration of a test compound, an agonist can be screened.

[7] The DNA containing TRE (TPA response element) is inserted into the multi-cloning site upstream of luciferase gene of Picagene basic vector or Picagene enhancer vector (Toyo Ink). It is referred to as TRE-reporter gene vector. In the cell transfected with the TRE-reporter gene vector, a stimulation which causes the increase in intracellular $Ca^{2+}$ induces an expression of luciferase gene through TRE and a production of luciferase protein. By measuring the luciferase activity, it is possible to detect the change in amount of intracellular calcium ion in the cells into which the TRE-reporter gene vector is introduced. The details of the screening method of a compound that alters the binding of MCH to SLT using the SLT-expressing cells into which TRE-reporter gene vector is transfected are as follows.

The TRE-reporter gene introduced SLT-expressing cells are placed in a 24-well plate at $5\times10^3$ cells/well, and cultivated for about 48 hours. The cells are washed with Hanks' buffer(pH7.4) containing 0.05% BSA and 20 mM HEPES. 10 nM MCH or a derivative thereof is added or 10 nM MCH or a derivative thereof and a test compound are added thereto. Then, the reaction is made at 37° C. for 60 minutes. The cells are dissolved in a decomposition solution for Picagene (Toyo Ink). To the decomposition solution, a luminescence substance (Toyo Ink) is added. The luminescence by luciferases can be measured with a luminometer, a liquid scintillation counter, a top counter or the like. An influence of a compound that alters the binding of MCH or a derivative to SLT can be measured by comparing the luminescence by luciferases with that when MCH or a derivative thereof is singly administrated. In this process, by administrating MCH or a derivative thereof, the amount of luminescence increases via the increase in intracellular $Ca^{2+}$. A compound that inhibits the increase may be selected as a candidate substance having an antagonistic activity. On the other hand, an agonist can be screened by adding a test compound singly and observing the increase in luminescence like the increase by MCH or a derivative thereof.

Alkaline phosphatase, chloramphenicol, acetyltransferase or β-galactosidase can be used as a reporter gene, besides luciferase. The activity of the product of reporter gene can be measured easily using commercially available measuring kit. The activity of alkaline phosphatase can be measured by Lumi-Phos 530(Wako); the activity of Chloramphenicol and acetyltransferase can be measured by FAST CAT chrolamphenicol Acetyltransferase Assay Kit(Wako); and the activity of β-galactosidase can be measured by Aurora Gal-XE (Wako).

[8] Growth of SLT-expressing cells in response to MCH through activation of MAP kinase is observed. This growth can be quantified by measuring the activation of MAP kinase, thymidine incorporation, number of cells (e.g. MTT). Using these measurements, a compound that alters the binding of MCH or a derivative to SLT can be screened.

After adding MCH or a derivative thereof, or adding MCH or a derivative thereof and a test compound to the cells, and then obtaining MAP kinase fraction from a decomposed cell solution by immunoprecipitation with an anti-MAP kinase antibody, MAP kinase activity can be measured easily by using, for example, MAP Kinase Assay Kit (Wako) and $\gamma$-$[^{32}P]$-ATP. For thymidine incorporation activity, MCH or a derivative thereof is added, or MCH or a derivative thereof and a test compound are added to the inoculated SLT-expressing cells. Then, [methyl-$^3$H]-thymidine is added thereto. A radioactivity of a labeled thymidine that is taken up into the cells can be measured by dissolving the cells and counting the radioactivity with a liquid scintillation counter.

To measure the growth of SLT-expressing cells, the cells are inoculated at first, and then MCH or a derivative thereof is added, or MCH or a derivative thereof and a test compound are added to the cells. Then, MTT (3-(4,5-dimethyl-2-thiazolyl)-2,5-diphenyl-2H-tetrazolium bromide) is added thereto. After dissolving the cells in iso-propanol which acidified by hydrochloric acid, MTT fromazan which is formed from MTT in the cells was measured by absorption at 570 nm.

The details of screening method using the labeled-thymidine incorporation activity for a compound that alters the binding of MCH to SLT are as follows.

SLT-expressing cells are placed at $5\times10^3$ cells/well on a 24-well plate and cultivated for a day. Then, the cells are cultivated in the medium without serum to make the cells to become starved condition. MCH or a derivative thereof is added, or MCH or a derivative thereof and a test compound are added to the cells and the cells are cultivated for 24 hours. [methyl-$^3$H]-thymidine at 0.015 MBq/well is added thereto and the cells are cultivated for 6 hours. The cells are washed with PBS(−), methanol is added thereto and kept still for 10 minutes. Then, 5% trichloro acetate was added and kept still for 15 minutes. The fixed cells are washed with distilled water 4 times. The cells are dissolved in 0.3 N sodium hydroxide. A radioactivity in the decomposed cell solution is measured with a liquid scintillation counter. An influence of a compound that alters the binding of MCH to SLT can be measured by comparing the increase in the radioactivity in thymidine incorporation with the case with the single administration of MCH or a derivative thereof. A compound that inhibits the increase in the radioactivity by MCH or a derivative thereof administration can be selected as a candidate substance having an antagonistic activity. On the other hand, by administrating a test compound alone and observing the increase in radioactivity, like that with MCH or a derivative thereof, an agonist can be screened.

[9] On adding MCH to SLT-expressing cells, K-channel becomes activated, and K ions in the cells flow out of the cells. At this time, Rb ions which belong to the related element, flow out of the cells through K channel as well as K ions. A labeled Rb ($[^{86}RB]$) is added to the cells to make the cells incorporate it. Then, by measuring the efflux of $[^{86}RB]$, the activity of MCH can be measured. The details of screening method for a compound that alters the binding of MCH to SLT by using the efflux activity of $[^{86}RB]$ are as follows.

Two days after placing in a 24-well plate, SLT-expressing cells are kept warm for 2 hours in the medium containing $^{86}RBCl$ (1 mCi/ml). The cells were washed well to remove $^{86}RBCl$ completely from the extracellular solution. MCH or a derivative thereof is added, or MCH or a derivative thereof and a test compound are added to the cells, and the extracellular solution is collected after 30 minutes. A radioactivity therein is measured by a γ-counter. An influence of a compound that alters the binding of MCH or a derivative thereof to SLT can be measured by comparing the increase in the radioactivity by efflux of $[^{86}RB]$ with the case of a single administration of MCH or a derivative thereof. A compound that inhibits the increase in the radioactivity by administrating MCH or a derivative thereof can be selected as a candidate substance having an antagonistic activity. On the other hand, by administrating a test compound alone and by observing the increase in radioactivity, like that by MCH or a derivative thereof, an agonist can be screened.

[10] SLT-expressing cells changes extracellular pH (acidification rate) in response to MCH. By measuring such change with the Cytosensor device (Molecular Device), the activity of MCH can be measured. The details of screening method for a compound that alters the binding of MCH to SLT by measuring the extracellular pH change with the Cytosensor device are as follows.

SLT-expressing cells are cultivated in a capsule of the Cytosensor over night. The cells are set to the chamber of the device and they are refluxed with RMPI1640 medium supplemented with 0.1% BSA (Molecular Device) for 2 hours until the extracellular pH become stable. After the pH becomes stable, measured is the pH change of the medium caused by refluxing the medium containing MCH or a derivative thereof, or the medium containing MCH or a derivative thereof and a test compound on the cells. An influence of a compound that alter the binding of MCH to SLT can be measured by comparing the change of extracellular pH in SLT-expressing cells with that by the single administration of MCH or a derivative thereof. A compound that inhibits the change of extracellular pH by administrating MCH or a derivative thereof can be selected as a candidate substance having an antagonistic activity. On the other hand, by administrating a test compound singly and observing the extracellular pH change, like that by MCH or a derivative thereof, an agonist can be screened.

[11] A sex pheromone receptor STe2 of haploid α-mating Type (MATα) of yeast (Saccharomyces cerevisiae) is coupled with G-protein Gpa1. In response to sex pheromone α-mating factor, the receptor activates MAP kinase, and sequentially Far1 (cell-cycle arrest) and transcription activation factor Ste12. Ste12 induces the expression of various proteins related to the mating, including FUSI. On the other hand, the regulatory factor Sst2 works in an inhibitory manner in the above process. In this system, yeast into which the receptor gene is introduced is prepared. The intracellular signal transduction system in the yeast is activated by a receptor agonist stimulation, and an experiment for the measurement system of the reaction between the receptor agonist and the receptor is conducted by using the growth, etc. resulted from the activation of the intracellular signal transduction as an index (Pausch, M. H., Trends in Biotechnology, vol. 15, pp. 487-494 (1997)). Using such system of the receptor gene introduced yeast, a compound that alters the binding of MCH to SLT can be screened.

The genes encoding Ste2 and Gpa1 of MATα yeast are removed and the SLT gene and the gene encoding Gpa1-Gai2 fused protein are introduced instead. The gene encoding Far is removed to prevent cell cycle arrest and the gene encoding Sst is removed to increase the sensitivity of response to MCH. Moreover, the FUS1-HIS3 gene in which FUS1 is connected with a histidine biosynthesis gene HIS3 is introduced. The above-mentioned genetic recombinant method can be easily carried out according to, for example, the method reported by Price (Price, L. A. et al., Molecular and Cellular Biology, vol. 15, pp. 6188-6195 (1995)), using SLT gene in place of a somatostatin receptor type 2 (SSTR2). The transformant of yeast constructed according to the above-mentioned method responds to MCH that is a ligand of SLT with a high sensitivity, causing the activation of MAP kinase and production of a histidine biosynthetic enzyme so that it can grow in a histidine deficient medium. Using this system, the response of SLT expressing yeast to MCH can be observed by using the yeast growth in the histidine deficient medium as an index.

The above-prepared transformant of yeast is cultured in a complete synthetic medium liquid overnight, added at a concentration of $2\times10^4$ cells/ml to a melted agar from which histidine is removed, and plated on square Petri dish (9×9 cm). After the agar becomes hard, a sterilized filter paper absorbing MCH or a derivative thereof, or absorbing MCH or a derivative thereof and a test compound, is placed on the surface of agar and the transformant is cultured for 3 days at 30° C. An influence of a compound that alters the binding of MCH or a derivative thereof to SLT can be measured by comparing the growth of yeast around the filter paper with the case of single administration of MCH or a derivative thereof. A compound that inhibits yeast growth caused by administration of MCH or a derivative thereof can be selected as a candidate substance having an antagonistic activity. On the other hand, an agonist can be screened by administrating a test compound alone and observing yeast growth like the growth observed on administration of MCH or a derivative thereof. Furthermore, the transformant of yeast is cultured on the agar containing MCH or a derivative thereof, and by observing an influence on yeast growth over the surface in Petri dish around the filter paper absorbing a test compound, an influence of a compound that alters the binding of MCH to SLT can be measured.

[12] An oocyte of Xenopus Laevis is injected with RNA of SLT gene and stimulated by MCH. As a result, intracellular $Ca^{2+}$ concentration increases and calcium-activated chloride current occurs. This change can be detected as a change of membrane potential (similar to the case where K ion concentration gradient is changed). By observing the reaction caused in the SLT-introduced Xenopus Laevis oocytes by MCH, a compound that has an influence on the binding of MCH to SLT can be screened.

A block of oocytes, collected from a female Xenopus Laevis numbed by ice-cooling, was treated with collagenase (0.5 mg/ml) dissolved in MBS solution (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM HEPES, pH7.4), shaking at 150 rpm for 1-6 hours at 19° C. until the block of cells gets loose. After washing for three times with MBS, poly(A)$^+$ SLT cRNA (50 ng/50 nl) is microinjected into an oocyte with a micromanipulator. SLT mRNA can be prepared from tissues or cells, or by in vitro transcription from a plasmid. The oocyte is cultured in MBS solution for 3 days at 20° C., and placed in a pit of a voltage clamp devise where Ringer solution flows. Glass microelectrodes for voltage clamp and voltmeter are inserted into the cell and the cathode is placed outside of the cell. After the potential become stable, the change in potential is recorded after passing the Ringer solution containing MCH or a derivative thereof, or the solution containing MCH or a derivative thereof and a test compound. An influence of a compound that alters the binding of MCH to SLT is measured by comparing the membrane potential change of SLT introduced Xenopus Laevis oocyte with that on single administration of MCH or a derivative thereof. A compound that inhibits the cell membrane potential change can be selected as a candidate substance having an antagonistic activity. On the other hand, an agonist can be screened by administrating only a test compound and observing the cell membrane potential change, like the change observed on administration of MCH or a derivative thereof.

In this system, poly (A)+ RNA of various G-protein genes can be introduced to amplify the change so that the reaction can be measured easily. Also, the poly (A)+ RNA of protein gene, such as aequorin which radiates light in the presence of Ca ion is injected as well so that the reaction can be measured by observing the radiation of light instead of the membrane potential change.

The screening kit for a compound or a salt thereof that alters the binding property of MCH or a salt thereof to SLT or a salt thereof comprises SLT or a salt thereof, cells containing SLT, or a membrane fraction of the cells containing SLT; and MCH, a derivative or a salt thereof.

As described above, since MCH used in the present invention is known to have a ligand activity to SLC-1, it is possible to search for a compound or a salt thereof that alters the binding property of MCH to SLC-1 (SLC-1 antagonist, SLC-1 agonist) by carrying out the above-mentioned screening methods using MCH and SLC-1 in place of SLT.

Thus, "a compound or a salt thereof that alters preferentially the binding property of MCH to SLC-1 (an antagonist or agonist having a preferential action on SLC-1)" or "a compound or a salt thereof that alters preferentially the binding property of MCH to SLT (an antagonist or agonist having a preferential action on SLT)" can be obtained by comparing the activity of a compound or a salt thereof that alters the binding property of MCH to SLT (SLT antagonist, SLT agonist), which is obtained by the screening method of the present invention, with that of a compound or a salt thereof that alters the binding property of MCH to SLC-1 (SLC-1 antagonist, SLC-1 agonist), which is obtained by the screening method of the present invention using SLC-1 for SLT, or the modified method thereof.

As used herein, the "compound or a salt thereof that alters preferentially the binding property" refers to:

(1) a compound or a salt thereof, the activity of which on one of SLT and SLC-1 (the receptor (SLT or SLC-1)-mediated cell-stimulating activity (e.g. activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation, or pH change, etc.), etc) is quantitatively different, usually at least 2-times, preferably 10-times different from the activity on the other; and/or (2) a compound or a salt thereof, the binding activity (e.g. $IC_{50}$) of which to one of SLT and SLC-1 is different, usually at least 2-times, preferably at least 10-times, more preferably at least 100-times, from the binding activity to the other.

Thus, the "antagonist having a preferential action on SLC-1" refers to:

(1) a compound or a salt thereof, the activity of which on SLC-1 (the receptor (SLC-1)-mediated cell-stimulating activity (e.g. activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation, or pH change, etc.), etc) is usually at least 2-times, preferably 10-times weaker over the activity on SLT; and/or (2) a compound or a salt thereof, the binding activity (e.g. $IC_{50}$) of which to SLC-1 is usually at least 2-times, preferably at least 10-times, more preferably at least 100-times stronger over the binding activity to SLT.

The "agonist having a preferential action on SLC-1" refers to:

(1) a compound or a salt thereof, the activity of which on SLC-1 (the receptor (SLC-1)-mediated cell-stimulating activity (e.g. activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation, or pH change, etc.), etc) is usually at least 2-times, preferably 10-times stronger over the activity on SLT; and/or (2) a compound or a salt thereof, the binding activity (e.g. $IC_{50}$) of which to SLC-1 is usually at least 2-times, preferably at least 10-times, more preferably at least 100-times stronger over the binding activity to SLT.

The "antagonist having a preferential action on SLT" refers to:

(1) a compound or a salt thereof, the activity of which on SLT (the receptor (SLT)-mediated cell-stimulating activity (e.g. activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation, or pH change, etc.), etc) is usually at least 2-times, preferably 10-times weaker over the activity on SLC-1; and/or (2) a compound or a salt thereof, the binding activity (e.g. $IC_{50}$) of which to SLT is usually at least 2-times, preferably at least 10-times, more preferably at least 100-times stronger over the binding activity to SLC-1.

The "agonist having a preferential action on SLT" refers to:

(1) a compound or a salt thereof, the activity of which on SLT (the receptor (SLT)-mediated cell-stimulating activity (e.g. activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation, or pH change, etc.), etc) is usually at least 2-times, preferably 10-times stronger over the activity on SLC-1; and/or (2) a compound or a salt thereof, the binding activity (e.g. $IC_{50}$) of which to SLT is usually at least 2-times, preferably at least 10-times, more preferably at least 100-times stronger over the binding activity to SLC-1.

In view of the above, the present invention further provides the screening method for a compound or its salt that alters the binding property of (1) MCH, a derivative or a salt thereof to (2) (i) SLC-1 or a salt thereof, or a partial peptide thereof, an amide, an ester or a salt thereof; and/or (ii) SLT or a salt thereof, or a partial peptide thereof, an amide, an ester or a salt thereof; which is characterized by using (i) MCH, a derivative or a salt thereof; (ii) SLC-1 or a salt thereof, or a partial peptide thereof, an amide, an ester or a salt thereof; and (iii) SLT or a salt thereof, or a partial peptide thereof, an amide, an ester or a salt thereof.

According to the screening method of the present invention, it is possible to screen or select:

(a) a compound or a salt thereof that alters preferentially the binding property of MCH, a derivative or a salt thereof to SLC-1 or a salt thereof, or a partial peptide thereof, an amide, an ester or a salt thereof;

(b) a compound or a salt thereof that alters preferentially the binding property of MCH, a derivative or a salt thereof to SLT or a salt thereof, or a partial peptide thereof, an amide, an ester or a salt thereof; and (c) a compound or a salt thereof that alters (i) the binding property of MCH, a derivative or a salt thereof to SLC-1 or a salt thereof, or a partial peptide thereof, an amide, an ester or a salt thereof; and (ii) the binding property of MCH, a derivative or a salt thereof to SLT or a salt thereof, or a partial peptide thereof, an amide, an ester or a salt thereof.

In the above-mentioned screening method, it is preferred to screen a compound or a salt thereof that alters preferentially the binding property of MCH, a derivative or a salt thereof to SLT or a salt thereof, or a partial peptide thereof, an amide, an ester or a salt thereof.

An example of the screening kit of the present invention is as follows:

1. Reagents for screening:

(1) Assay Buffer and Wash Buffer

Hanks' balanced salt solution (Gibco Co.) supplemented with 0.05% bovine serum albumin (Sigma Co.). The solution is sterilized by filtration through a 0.45 μm filter, and stored at 4° C. or may be prepared at use.

(2) Standard SLT Preparation and Standard SLC-1 Preparation

CHO cells expressing SLT or SLC-1 which are plated on a 12-well plate at a density of $5 \times 10^5$ cells/well, and cultured at 37° C. under 5% $CO_2$ and 95% air for 2 days.

(3) Labeled Ligand

MCH labeled with $[^3H]$, $[^{125}I]$, $[^{14}C]$, $[^{35}S]$, etc., which is dissolved in an appropriate buffer, and stored at 4° C. or −20° C., and diluted to 1 μM with the measurement buffer at use.

(4) Standard Ligand Solution

MCH is dissolved in PBS containing 0.1% bovine serum albumin(Sigma Co.) at a final concentration of 1 mM, and stored at −20° C.

2. Assay method:

(1) The cells expressing SLT or SLC-1 are cultured in a 12-well culture plate and washed twice with 1 ml of the assay buffer, and 490 μl of the assay buffer is added to each well.

(2) After adding 5 μl of $10^{-3}$–$10^{-10}$ M test compound solution, and then 5 μl of the labeled MCH, the cells are incubated at room temperature for an hour. To determine the amount of the non-specific binding, 5 μl of $10^{-3}$ M ligand (MCH) is added in place of a test compound.

(3) The reaction solution is removed, and the wells are washed 3 times with the wash buffer. The labeled ligand (MCH) bound to the cells is dissolved in 0.2N NaOH-1% SDS, and mixed with 4 ml of liquid scintillator A (Wako Pure Chemical Industries, Ltd.).

(4) The radioactivity is measured using a liquid scintillation counter (Beckman Co.), and the percent maximum binding (PMB) is calculated by the following formula [equation 1].

$$PMB=[(B-NSB)/(B_0-NSB)] \times 100 \qquad \text{[equation 1]}$$

PMB: Percent maximum binding
B: Amount obtained in the presence of a test compound
NSB: Non-specific binding
$B_0$: Maximum binding A compound or a salt thereof, which is obtained by the screening method or the screening kit of the present invention, is a compound that alters (inhibits or enhances) the binding of MCH or a salt thereof to SLT or a salt thereof. Specifically, it is a compound or a salt thereof having the SLT-mediated cell-stimulating activity (so-called SLT agonist) or a compound not having the cell-stimulating activity (so-called SLT antagonist). The compounds include peptides, proteins, non-peptide compounds, synthetic compounds, and fermentation products, which may be novel or known compounds.

The evaluation as to whether a compound is an SLT agonist or SLT antagonist may be carried out as described in (i) and (ii) below.

(i) By conducting the binding assay according to the screening methods (1)-(3) above, a compound that alters (especially, inhibits) the binding property of MCH or a salt thereof to SLT or a salt thereof is obtained. Then, the obtained compound is assayed as to whether it has the above-mentioned SLT-mediated cell-stimulating activities or not. A compound or a salt thereof having the cell-stimulating activities is an SLT agonist, and a compound or a salt thereof not having the cell-stimulating activities is an SLT antagonist.

(ii)(a) The above-mentioned SLT-mediated cell-stimulating activity is measured after contacting a test compound to cells containing SLT. The compound having the cell-stimulating activity or salt hereof is an SLT agonist.

(b) The above-mentioned SLT-mediated cell-stimulating activity is measured and compared between when a compound that activates SLT (e.g. the polypeptide of the present invention or SLT agonist) is brought in contact with cells containing SLT and when the compound that activates SLT and a test compound are brought in contact with cells containing SLT. A compound or a salt thereof that can reduce the cell-stimulating activity induced by the compound that activates SLT is an SLT antagonist.

Since SLT agonists have the same physiological activity as that of MCH or a salt thereof to SLT, they are useful as safe and low-toxic pharmaceuticals, like MCH or a salt thereof.

On the other hand, since SLT antagonists can inhibit the physiological activity of MCH or a salt thereof to SLT, they are useful as safe and low-toxic pharmaceuticals for inhibiting the receptor activity.

A compound or a salt thereof, which is obtained by the screening method or the screening kit of the present invention using SLC-1, is a compound that alters (inhibits or enhances) the binding of MCH or a salt thereof to SLC-1 or a salt thereof. Specifically, it is a compound or a salt thereof having the SLC-1-mediated cell-stimulating activity (so-called SLC-1 agonist) or a compound not having the cell-stimulating activity (so-called SLC-1 antagonist). The compounds include peptides, proteins, non-peptide compounds, synthetic compounds, and fermentation products, which may be novel or known compounds.

The evaluation as to whether a compound is an SLC-1 agonist or an SLC-1 antagonist may be carried out as described in (i) and (ii) above.

Since SLC-1 agonists have the same physiological activity as that of MCH or a salt thereof to SLC-1, they are useful as safe and low-toxic pharmaceuticals, like MCH or a salt thereof.

On the other hand, since SLC-1 antagonists can inhibit the physiological activity of MCH or a salt thereof to SLC-1, they are useful as safe and low-toxic pharmaceuticals for inhibiting the receptor activity.

Since MCH or a salt thereof is involved in appetite (eating) promoting action and oxytocin secretion promoting action, it can be used as an agent for promoting appetite (eating) and oxytocin secretion. Thus, among compounds obtained by the above-mentioned screening methods or screening kits, SLT agonists and SLC-1 agonists can be used as an agent for promoting appetite (eating), and further can be used as a prophylactic and/or therapeutic agent for weak uterine contraction, atonic bleeding, delivery of placenta, uterine involution insufficiency, Caesarean operation, artificial abortion, lactic retention, anorexia, such as anorexia nervosa; and anemia and hypoproteinosis associated therewith; and the like. SLT antagonists and SLC-1 antagonists can be used as a prophylactic and/or therapeutic agent for obesity (e.g. malignant mastocytosis, exogenous obesity, hyperinsulinar obesity, hyperplasmic obesity, hypophyseal obesity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia, emotional disorder, sexual dysfunction; and further can be used as a prophylactic and/or therapeutic agent for too strong uterine contraction, tonic uterine contraction, fetal asphyxia, uterine rupture, endocervical canal laceration, premature delivery, Prader-Willi syndrome, diabetes mellitus and its complications (diabetic nephropathy, diabetic retinopathy, diabetic neuropathy, etc.) hypertension, hyperlipemia, coronary arterial sclerosis, gout, respiratory disease (Pickwick syndrome, sleep apnea syndrome), fatty liver, infertility, osteoarthritis, etc. (in particular, anti-obesity agents, appetite (eating) regulators).

For a salt of a compound that can be obtained according to the above-mentioned screening method or the screening kit, for example, a pharmacologically acceptable salt is used. Examples thereof include a salt with an inorganic base, a salt with an organic base, a salt with an inorganic acid, a salt with an organic acid, a salt with a basic or acidic amino acid and so on.

Preferred examples of the salt with an inorganic base include an alkali metal salt such as sodium salt, potassium salt; alkali earth metal salt, calcium salt and magnesium salt; and aluminum salt, ammonium salt, etc.

Preferred examples of the salt with an organic base include trimethylamine salt, triethylamine salt, pyridine salt, picoline salt, 2,6-lutidine salt, ethanolamine salt, diethanolamine salt, triethanolamine salt, cyclohexylamine salt, dicyclohexylamine salt, N,N'-dibenzylethylenediamine salt, etc.

Preferred examples of the salt with an inorganic acid include hydrochloric acid salt, hydrobromic acid salt, sulfuric acid salt, phosphoric acid salt, etc.

Preferred examples of the salt with an organic acid include formic acid salt, acetic acid salt, propionic acid salt, fumaric acid salt, oxalic acid salt, tartaric acid salt, maleic acid salt, citric acid salt, succinic acid salt, malic acid salt, methanesulfonic acid salt, benzenesulfonic acid salt, benzoic acid salt, etc.

Preferred examples of the salt with a basic amino acid include a salt with arginine, lysine, ornithine, etc. Preferred examples of the salt with an acidic amino acid include a salt with aspartic acid, glutamic acid, etc.

When a compound obtained using the screening method or the screening kit or a salt thereof is used as the above-mentioned pharmaceutical preparation, it can be prepared by a publicly known method. For example, the preparation can be used orally as a tablet having sugar coating or enteric coating as necessary, a capsule, an elixir and a microcapsule, or parenterally as an injection, such as an aseptic solution or suspension with water or other pharmaceutically acceptable. For example, the pharmaceutical preparation of the present invention can be produced by admixing physiologically acceptable carriers, flavors, excipients, vehicles, preservatives, stabilizers and binders with the compound or a salt thereof in a generally acceptable unit dose form. The amount of the active ingredient in these pharmaceutical preparations is designed to have a suitable dose in the designated range.

Additives which can be admixed in a tablet, a capsule, etc. include, for example, binders such as gelatin, corn starch, tragacanth, gum arabic; excipients such as crystalline cellulose; swelling agents such as corn starch, gelatin and alginic acid; lubricants such as magnesium stearate; sweeteners such as sucrose, lactose and saccharine; and flavors such as peppermint, akamono oil and cherry. When a capsule is in a unit dosage form, liquid carriers such as fats and oils can be contained in the materials described above. An aseptic composition for injection can be formulated according to conventional pharmaceutical formulation by dissolving or suspending the active material and naturally occurring vegetable oils such as sesame oil and coconut oil in vehicles such as injection water.

The aqueous liquid for injection includes, for example, a physiological saline or an isotonic solution containing glucose and other supplementary agents (e.g., D-sorbitol, D-mannitol, sodium chloride etc.), and may be used in combination with suitable solubilizer such as alcohols (e.g., ethanol etc.), polyalcohols (e.g., propylene glycol, polyethylene glycol etc.) and nonionic surfactants (e.g., Polysorbate 80™, HCO-50 etc.). The oily liquid includes, for example, sesame oil, soybean oil etc., and may be used in combination with solubilizer such as benzyl enzoate, benzyl alcohol etc.

Further, it may contain buffers (e.g., phosphate buffer, sodium acetate buffer etc.), soothing agents (e.g., benzalkonium chloride, procaine hydrochloride etc.), stabilizers (e.g., human serum albumin, polyethylene glycol etc.), preservatives (e.g., benzyl alcohol, phenol etc.), antioxidants etc. Usually, the prepared injection is filled into suitable ampoules.

The pharmaceutical preparation thus obtained is safe and low toxic so that it can be administered to a human or a mammal (e.g. mouse, rat, guinea pig, rabbit, sheep, pig, cow, cat, dog, monkey, chimpanzee).

The dose of the compound or a salt thereof obtained by the screening method or the screening kit of the present invention varies depending on conditions. In oral administration to an adult (60 kg body weight), the dose is normally about 0.1 to 1000 mg, preferably about 1.0 to 300 mg, and more preferably about 3.0 to 50 mg per day. In parenteral administration, the single dose also varies depending on subject to be administered, conditions, routes for administration, etc. For example, in an injection form, it is advantageous to inject intravenously SLC antagonist to an adult with obesity (60 kg body weight) in a daily does of about 0.01 to 30 mg, preferably about. 0.1 to 20 mg, and more preferably about 0.1 to 10 mg. The dose for other animal species can be calculated in proportion to the body weight on the basis of the dose per 60 kg.

In the specification and drawings, bases and amino acids are denoted in accordance with the IUPAC-IUB Commission on Biochemical Nomenclature or the conventional manner in the art, examples of which are shown below. The possible optical isomer of an amino acid is L form unless otherwise indicated.

| | |
|---|---|
| DNA: | deoxyribonucleic acid |
| cDNA: | complementary deoxyribonucleic acid |
| A: | adenine |
| T: | thymine |
| G: | guanine |
| C: | cytosine |
| Y: | thymine or cytosine |

-continued

| | |
|---|---|
| N: | adenine, guanine, cytosine or thymine |
| R: | adenine or guanine |
| M: | adenine or cytosine |
| W: | adenine or thymine |
| S: | guanine or cytosine |
| RNA: | ribonucleic acid |
| mRNA: | messenger ribonucleic acid |
| dATP: | deoxyadenosine triphosphate |
| dTTP: | deoxythymidine triphosphate |
| dGTP: | deoxyguanosine triphosphate |
| dCTP: | deoxycytidine triphosphate |
| ATP: | adenosine triphosphate |
| EDTA: | ethylenediaminetetraacetic acid |
| SDS: | sodium dodecyl sulfate |
| TFA: | trifluoroacetic acid |
| EIA: | enzyme immunoassay |
| Gly or G: | glycine |
| Ala or A: | alanine |
| Val or V: | valine |
| Leu or L: | leucine |
| Ile or I: | isoleucine |
| Ser or S: | serine |
| Thr or T: | threonine |
| Cys or C: | cysteine |
| Met or M: | methionine |
| Glu or E: | glutamic acid |
| Asp or D: | aspartic acid |
| Lys or K: | lysine |
| Arg or R: | arginine |
| His or H: | histidine |
| Phe or F: | phenylalanine |
| Tyr or Y: | tyrosine |
| Trp or W: | tryptophan |
| Pro or P: | proline |
| Asn or N: | asparagine |
| Gln or Q: | glutamine |
| pGlu: | pyroglutamic acid |
| Me: | methyl |
| Et: | ethyl |
| Bu: | butyl |
| Ph: | phenyl |
| TC: | thiazolidine-4(R)-carboxamide |
| Bom: | benzyloxymethyl |
| NMP: | N-methylpyrrolidone |
| PAM: | phenylacetoamidemethyl |

The substituents, protective groups and reagents, which are frequently used in the specification, are shown by the following abbreviations.

| | |
|---|---|
| Tos: | p-toluenesulfonyl |
| HONB: | 1-hydroxy-5-norbornene-2,3-dicarboximide |
| Bzl: | benzyl |
| Z: | benzyloxycarbonyl |
| Br-Z: | 2-bromobenzyloxycarbonyl |
| Cl-Z: | 2-chlorobenzyloxycarbonyl |
| Boc: | t-butoxycarbonyl |
| HOBt: | 1-hydroxybenztriazole |
| DCC: | N,N'-dicyclohexylcarbodiimide |
| TFA: | trifluoroacetic acid |
| Fmoc: | N-9-fluorenylmethoxycarbonyl |
| DNP: | dinitrophenyl |
| Bum: | t-butoxymethyl |
| Trt: | trityl |
| BSA: | bovine serum albumin |
| CHAPS: | 3-[(3-colamidepropyl)dimethylanmmonio]-1-propane sulfonate |
| PMSF: | phenylmethylsulfonylfluoride |
| E64: | (L-3-trans-carboxoirane-2-carbonyl)L-leucyl-agumatin |
| GDP: | Guanosine-5'-diphosphate |
| MEM α: | minimum essential medium alpha |
| Fura-2AM: | 1-[6-amino-2-(5-carboxy-2-oxazolyl)-5-benzofuranyloxy]-2-(2-amino-5-methylphenoxy)-ethane-N', N', N', N'-tetra acetic acid-pentaacetoxymethyl ester |

-continued

| | |
|---|---|
| HBSS: | Hanks' Balanced Salt Solution |
| Fluo-3AM: | 1-[2-amino-5-(2,7-dichloro-6-hydroxy-3-oxy-9-xanthenyl) phenoxy]-2-(2-amino-5-methylphenoxy)ethane-N', N', N', N'-tetra acetic acid pentaacetoxymethyl ester |
| HEPES: | 2-[4-(2-hydroxyethyl)-1-piperazinyl]ethanesulfonic acid |
| MeBzl: | 4-methylbenzyl |
| NMP: | N-methylpyrrolidone |

The sequence identification numbers in the Sequence Listing indicate the following sequences.

[SEQ ID NO: 1]
This shows a synthetic DNA used for cloning of cDNA encoding human SLT.

[SEQ ID NO: 2]
This shows a synthetic DNA used for cloning of cDNA encoding human SLT.

[SEQ ID NO: 3]
This shows the full amino acid sequence of human SLT.

[SEQ ID NO: 4]
This shows the full nucleotide sequence of human SLT cDNA having Sal I recognition sequence added to 5'-terminal and Spe I recognition sequence added to 3'-terminal.

[SEQ ID NO: 5]
This shows a riboprobe used for measuring the expression amount of SLT mRNA in each CHO cell clone expressing human SLT.

[SEQ ID NO: 6]
This shows the amino acid sequence of melanin-concentrating hormone, MCH.

[SEQ ID NO: 7]
This shows the nucleotide sequence of a synthetic DNA used for cloning of cDNA encoding human SLT.

[SEQ ID NO: 8]
This shows the nucleotide sequence of a synthetic DNA used for cloning of cDNA encoding human SLT.

[SEQ ID NO: 9]
This shows the nucleotide sequence of cDNA encoding human SLT having the amino acid sequence shown by SEQ ID NO: 3.

[SEQ ID NO: 10]
This shows the amino acid sequence of Des-$Asp^1$-MCH (MCH(2-19)).

[SEQ ID NO: 11]
This shows the amino acid sequence of Des-[$Asp^1$, $Phe^2$]-MCH (MCH(3-19)).

[SEQ ID NO: 12]
This shows the amino acid sequence of Des-[$Asp^1$, $Phe^2$, $Asp^3$]-MCH (MCH(4-19)).

[SEQ ID NO: 13]
This shows the amino acid sequence of Des-[$Asp^1$, $Phe^2$, $Asp^3$, $Met^4$]-MCH (MCH(5-19)).

[SEQ ID NO: 14]
This shows the amino acid sequence of Des-[$Asp^1$, $Phe^2$, $Asp^3$, $Met^4$, $Leu^5$]-MCH (MCH(6-19)).

[SEQ ID NO: 15]
This shows the amino acid sequence of Des-[$Asp^1$, $Phe^2$, $Asp^3$, $Met^4$, $Leu^5$, $Arg^6$]-MCH (MCH(7-19)).

[SEQ ID NO: 16]

This shows the full amino acid sequence of rat SLC-1.

[SEQ ID NO: 17]

This shows the whole amino acid sequence of human SLC-1.

[SEQ ID NO: 18]

This shows the nucleotide sequence of DNA encoding the amino acid sequence shown by SEQ ID NO: 16.

[SEQ ID NO: 19]

This shows the nucleotide sequence of DNA encoding the amino acid sequence shown by SEQ ID NO: 17.

*Escherichia coli* DH5α/pCR3.1-hSLT, which was obtained in Reference Example 1, was on deposit with the Ministry of International Trade and Industry, Agency of Industrial Science and Technology, National Institute of Bioscience and Human Technology (NIBH), located at 1-1-3, Higashi, Tsukuba-shi, Ibaraki, Japan, as the Accession Number FERM BP-6710 on Apr. 28, 1999; and with Institute for Fermentation (IFO), located at 2-17-85, Juso Honcho, Yodogawa-ku, Osaka-shi, Osaka, Japan, as the Accession Number IFO 16284 on Apr. 20, 1999.

EXAMPLES

The following examples and reference examples are intended to illustrate the present invention in detail, but not intended to limit the scope of the present invention.

Reference Example 1

Cloning of cDNA Encoding Human Receptor Protein SLT from Human Hippocampus cDNAs Using human hippocampus cDNAs (Clontech Laboratories, Inc.) as a template, PCR was carried out by use of 2 primers, namely, primer 1 (SEQ ID NO:7) and primer 2 (SEQ ID NO:8). The composition of the reaction solution in the reaction above was composed of 1/10 vol. of the cDNAs used as the template, 1/50 vol. of Advantage 2 Polymerase Mix (Clontech Laboratories, Inc.) and 0.2 μM each of primer 1 (SEQ ID NO:7) and primer 2 (SEQ ID NO:8), 200 μM of dNTPs, and the buffer attached to the enzyme to make the volume of 25 μl. In the PCR, (I) after reacting at 94° C. for 1 minute, (2) the cycle set at 94° C. for 20 seconds and at 72° C. for 2 minutes was repeated in 3 cycles, (3) the cycle set at 94° C. for 20 seconds, at 65° C. for 20 seconds and at 68° C. for 2 minutes was repeated in 3 cycles, (4) the cycle set at 94° C. for 20 seconds, at 58° C. for 20 seconds and at 68° C. for 2 minutes was repeated in 36 cycles, and (3) finally extension was performed at 68° C. for 7 minutes. After completion of the PCR, the reaction product was subcloned into plasmid vector pCR3.1 (Invitrogen, Inc.) in accordance with the protocol of TA Cloning Kit (Invitrogen, Inc.). The vector was then introduced into *Escherichia coli* DH5α. After the cDNA-bearing clones were selected in LB agar medium containing ampicillin, individual clones were analyzed for determining their sequences, giving a cDNA sequence (SEQ ID NO:9) encoding a novel G protein-coupled receptor protein. The novel G protein-coupled receptor protein comprising an amino acid sequence (SEQ ID NO:3) deduced from this cDNA was named hSLT and the transformant was named *Escherichia coli* DH5α/pCR3.1-hSLT.

Reference Example 2

Preparation of Des-[Asp$^1$, Phe$^2$, Asp$^3$]-MCH (MCH (4-19), Met-Leu-Arg-Cys-Met-Leu-Gly-Arg-Val-Tyr-Arg-Pro-Cys-Trp-Gln-Val)

Into a reaction vessel of a peptide synthesizer ABI 430A, 0.5 mmol of Boc-Val-OCH$_2$-PAM resin (0.77 mmol/g resin) commercially available was charged. Using the Boc-strategy (NMP-HOBt) peptide synthesis method, Boc-Gln, Boc-Trp (CHO), Boc-Cys (MeBzl), Boc-Pro, Boc-Arg (Tos), Boc-Tyr (Br-Z), Boc-Val, Boc-Arg(Tos), Boc-Gly, Boc-Leu, Boc-Met, Boc-Cys (MeBzl), Boc-Arg (Tos), Boc-Leu and Boc-Met were introduced in this order to give the objective protected peptide resin. After 0.6 g of this resin was stirred in 10 ml of anhydrous hydrogen fluoride together with 2 g of p-cresol and 1.2 ml of 1,4-butane-dithiol at 0° C. for 60 minutes, the hydrogen fluoride was removed by distillation in vacuum. Diethyl ether was added to the residue and the resulting precipitates were filtrated. Then the precipitates were extracted with 50% aqueous acetic acid solution added thereto, and insoluble matters were removed. The extract was well concentrated, and then applied to Sephadex (trade name) G-25 column (2.0×80 cm) in 50% aqueous acetic acid. By development with the solvent, the major fractions were collected and then applied to a reversed phase chromatography column (2.6×60 cm) packed with LiChroprep (trade name) RP-18. After the column was washed with 200 ml of 0.1% TFA in water, linear gradient elution was performed using 300 ml of 0.1% TFA in water and 300 ml of 40% acetonitrile in water containing 0.1% TFA. The major fractions were collected and concentrated. The concentrate was dissolved in about 4 ml of acetic acid. After the solution was diluted to 240 ml with distilled water, the dilution was adjusted to pH 7.5 using ammonia water, and then gently stirred with pumping air. The reaction was monitored with HPLC. After it was confirmed that the peak of SH form-peptide is all changed to the SS-form, acetic acid was added to adjust pH of the solution to 3, and the mixture was applied to the LiChroprep (trade name) RP-18 column described above for adsorption. After the column was washed with 200 ml of 0.1% TFA in water, linear gradient elution was performed using 300 ml of 0.1% TFA in water and 300 ml of 50% acetonitrile in water containing 0.1% TFA. The major fractions were pooled and lyophilized to give the objective peptide.

Mass spectrum (M+H)$^+$ 2009.9 (calcd. 2010.0) HPLC elution time: 17.9 mins. Column conditions: Column: Wakosil-II 5C18HG (4.6×150 mm) Eluent: Eluent A—0.1% TFA containing 10% acetonitrile in water, Eluent B—0.1% TFA containing 60% acetonitrile in water; linear gradient elution from A/B 20/80 to 80/20 (20 mins.) Flow rate: 1.0 ml/min.

Reference Example 3

Preparation of Radioisotope-labeled MCH (4-19)

MCH (4-19) prepared in REFERENCE EXAMPLE 2 that was a truncated form of MCH, in which the N-terminal 3 amino acid residues were deleted, was labeled with radioisotope in accordance with the Bolton-Hunter method. Dry nitrogen gas was blown into a solution of 9.25 MBq (0.11 nmol) of [$^{125}$I]-Bolton-Hunter reagent (N-succinimidyl 3-(4-hydroxy-3-iodophenyl) propionate) (NEN Life Science Products, Inc., 81.4 TBq/mmol) dissolved in benzene in a tube thereby to remove benzene by distillation. In the tube, 18 μl of 50 mM phosphate buffer (pH 7.5), a solution of 2.3 nmols of MCH (4-19) in 1.5 μl of dimethylsulfoxide and 0.5 μl of dimethylsulfoxide were charged and mixed thoroughly. After the mixture was kept at 37° C. for 2 hours, the radioactive derivative of MCH (4-19) prepared by the Bolton-Hunter reagent, i.e. [125I]-[N-3-(4-hydroxy-3-iodophenyl)propionyl)-Met$^4$]-MCH (4-19), was fractionated by reversed phase HPLC. [$^{125}$I]-[N-3-(4-hydroxy-3-iodophenyl)propionyl)-Met$^4$]-MCH (4-19) was eluted through ODS column (Toso, ODS-80™ (4.6 mm×150 mm)) at an acetonitrile concentration of about 43.6%.

6 times, MCH (3-19), MCH (4-19), MCH (5-19), MCH (6-19) and MCH (7-19), in which N-terminal amino group was truncated one by one, were obtained, respectively.

MCH (2-19), MCH (3-19), MCH (4-19), MCH (5-19), MCH (6-19) and MCH (7-19) obtained by the above degradation were purified by the following procedure, and their structures were confirmed by mass spectrometry and amino acid analysis. Hereinafter, the analysis of MCH (4-19) is described in detail but almost the same procedure was applied to the other derivatives as well. Analytical data of MCH (2-19), MCH (3-19), MCH (4-19), MCH (5-19), MCH (6-19) and MCH (7-19) thus obtained are shown in TABLE 1.

TABLE 1

Data of Mass spectrometry and Amino-Acid Analysis of of MCH(2-19), MCH(3-19), MCH(4-19), MCH(5-19), MCH(6-19) and MCH(7-19)

| Structure | Mass (M + H$^+$) found (calcd.) composition formula | Amino-Acid Analysis (No. of residues) |
|---|---|---|
| MCH(2-19) | 2272.3 (2272.1) $C_{101}H_{156}N_{29}O_{23}S_4$ | D 1.90 (1), E 2.28 (1), P 1.32 (1), G 2.33 (1), V 1.76 (2), C n.d. (1), M 0.46 (2), L 2.0 (2), Y 0.50 (1), F 0.93 (1), R 1.98 (3) |
| MCH(3-19) | 2124.8 (2125.0) $C_{92}H_{147}N_{28}O_{22}S_4$ | D 1.01 (1), E 1.05 (1), P 1.25 (1), G 1.02 (1), V 1.9 (2), C 0.30 (1), M 1.37 (2), L 2.0 (2), Y 0.20 (1), R 2.94 (3) |
| MCH(4-19) | 2009.9 (2010.0) $C_{88}H_{142}N_{27}O_{19}S_4$ | E 1.04 (1), P 1.12 (1), G 1.02 (1), V 1.88 (2), C 0.34 (1), M 1.42 (2), L 2.0 (2), Y 0.23 (1), R 2.93 (3) |
| MCH(5-19) | 1878.9 (1878.9) $C_{83}H_{133}N_{26}O_{18}S_3$ | E 1.51 (1), P 0.69 (1), G 2.16 (1), V 1.27 (2), C n. d. (1), M 0.38 (1), L 2.0 (2), Y 0.18 (1), R 1.80 (3) |
| MCH(6-19) | 1765.5 (1765.9) $C_{77}H_{122}N_{25}O_{17}S_3$ | E 0.69 (1), P 0.79 (1), G 0.70 (1), V 1.21 (2), C 0.15 (1), M 0.50 (1), L 1.0 (1), Y 0.20 (1), R 1.84 (3) |
| MCH(7-19) | 1609.2 (1608.8) $C_{71}H_{110}N_{21}O_{16}S_3$ | E 0.90 (1), P 0.62 (1), G 1.03 (1), V 1.05 (2), C 0.07 (1), M 0.33 (1), L 1.0 (1), Y 0.15 (1), R 1.04 (2) |

Reference Example 4

Preparation of MCH (2-19), MCH (3-19), MCH (4-19), MCH (5-19), MCH (6-19) and MCH (7-19) (SEQ ID NOS:10-15) by Manual Edman Degradation In 30 μl of 50% pyridine, 0.1 mg of MCH (Sigma, Inc.) was dissolved. After 1 μl of phenyl isothiocyanate (Wako Pure Chemical Industries, Ltd.) was added to the solution for nitrogen replacement, the mixture was kept at 45° C. After an hour passed with stirring every 10 minutes, it was stopped to keep warm and the mixture was evaporated to dryness under a nitrogen flow. The residue was again dissolved in 20 μl of ethanol and the solvent was removed under a nitrogen flow and then evaporated to dryness in vacuum. The reaction product, phenylthiocarbamoyl derivative, was dissolved in 20 μl of trifluoroacetic acid (Wako Pure Chemical Industries, Ltd.) for nitrogen replacement. The solution was warmed to 45° C. for 20 minutes to cut out the amino terminal amino acid of the peptide as the anilinothiazolinone derivative. After removing trifluoroacetic acid under a nitrogen flow, 30 μl of water and 100 μl of n-butyl acetate were added, whereby an excess of the reagent and the anilinothiazolinone derivative were removed by extraction with n-butyl acetate. The extraction with n-butyl acetate was repeated 3 times. The aqueous phase containing MCH (2-19) with the amino end truncated by one residue was evaporated to dryness under a nitrogen flow and then in vacuum.

This degradation process was carried out only once to give MCH (2-19) with the amino end deleted of one residue only. By repeating a similar degradation process 2, 3, 4, 5 or MCH (4-19) was purified on HPLC by the following procedure. By previously passing Eluent A (0.1% trifluoroacetic acid) through a Spheri-5 RP-18 reversed phase high performance liquid chromatography column (Brownlee Labs., 2.1 mm×30 mm) at a flow rate of 300 μl/min., the column was equilibrated at 25° C. The reaction product was dissolved in 270 μl of 0.1% trifluoroacetic acid and a 50 μl aliquot of the solution was loaded onto the column. While maintaining the flow rate of 300 μl/min., the concentration of Eluent B (0.1% trifluoroacetic acid/70% acetonitrile) was increased to 70% over 30 minutes. The eluate was monitored by an absorbance of 210 nm and the peaks were manually fractionated. MCH (4-19) was eluted at 17.1 minutes. MCH (4-19) collected in one test tube was concentrated to dryness and the concentrate was dissolved in 100 μl of DMSO.

Mass spectrometry was performed by the LSIMS method using JEOL JMS-HX110. That is, one μl of 3:2 matrix of 3-nitrobenzyl alcohol and glycerol was mixed with 1 μl of a sample on a probe chip and the mixture was introduced into an ionization source. Cesium ions accelerated to 15 kv was bombarded on the ionization source and the positive secondary ions generated were accelerated to 10 kv, which was led to a detector.

Hydrolysis for amino acid analysis was carried out by adding 5 μl of a sample into a glass tube, solidifying the sample to dryness in vacuum, charging the solid in a reaction vial, putting 200 μl of 6N azeotropic hydrochloric acid (Pierece Chemical, Sequenal Grade) to the bottom of the vial, effecting deaeration in Pico-Tag work station of Waters, Inc., by the method recommended by Waters, Inc., and maintaining at 110° C. for 24 hours.

Hydrochloric acid in the reaction vial was removed in vacuum using a vacuum pump, and the sample was then diluted with 150 µl of 20 mM hydrochloric acid. The dilution was charged in a vial for analysis and set on an amino acid analyzer. An aliquot of 100 µl was provided for the analysis. The amino acid analysis was carried out on a high performance amino acid analyzer, Hitachi L-8500, by fluorometry using ortho-phthalaldehyde reagent (Wako Pure Chemical Industries, Inc.) for derivatization. Preparation of the buffer for fluorometry, preparation of the reaction solution and conditions for analysis were followed as given in the instructions for the L-8500 amino acid analyzer. The molar ratios of measured values based on leucine are shown in TABLE 1.

MCH or MCH (2-19), MCH (3-19), MCH (4-19) and MCH (5-19) can also be prepared by the solid phase synthesis method described in REFERENCE EXAMPLES 7 through 11.

Reference Example 5

Derivatization of MCH, MCH (2-19), MCH (3-19), MCH (4-19) and MCH (5-19) with Non-isotope Bolton-Hunter Reagent Derivatization of MCH and, MCH (2-19), MCH (3-19), MCH (4-19), MCH (5-19) and MCH (6-19) was performed using non-isotope Bolton-Hunter reagent. The derivatization of MCH (4-19) is described below as an example.

To a solution of 1 nmol of MCH (4-19) in 50 µl of dimethylformamide, 100 nmols of non-isotope Bolton-Hunter reagent or N-succinimidyl 3-(4-hydroxy-3-iodophenyl)propionate (Wako Pure Chemical Industries, Ltd.) and 100 nmols of N,N-diisopropylethylamine (Wako Pure Chemical Industries, Ltd.) were added, and the mixture was incubated at 37° C. for 4 hours for the reaction.

After 450 µl of 10% acetonitrile containing 0.1% trifluoroacetic acid was added to the reaction mixture, the purification was performed on HPLC. Conditions for the chromatography were as follows. Wakosil-II 5C18HG (4.6×150 mm) was used as a column and the flow rate was maintained at 1.0 ml/min. Elution was carried out using acetonitrile in water containing 0.1% trifluoroacetic acid, by maintaining the acetonitrile concentration of 10% for 2 minutes, then increasing to 20% over 5 minutes and further increasing to 50% over 20 minutes. MCH (4-19) derivative with the non-isotope Bolton-Hunter reagent, namely, [N-(3-(4-hydroxy-3-iodophenyl)propionyl)-Met$^4$]-MCH (4-19), was eluted at 22.9 minutes and manually fractionated. MCH or MCH (2-19), MCH (3-19), MCH (5-19) and MCH (6-19) were derivatized in a similar manner by introducing the 3-(4-hydroxy-3-iodophenyl)propionyl group into the amino group of the N-terminal amino acid, and then fractionated through HPLC. After acid hydrolysis, these derivatives were provided for amino acid analysis. The results are shown in TABLE 2.

TABLE 2

Data of Amino-Acid Analysis of derivatives of MCH(2-19), MCH(3-19), MCH(4-19), MCH(5-19) and MCH(6-19)

| Structure | Amino-Acid Analysis (No. of residues) |
|---|---|
| Derivative of MCH(2-19) | D 1.01 (1), E 1.05 (1), P 0.86 (1), G 1.09 (1), V 1.69 (2), C n.d. (1), M 1.01 (2), L 2.0 (2), Y 0.27 (1), F 0.90 (1), R 2.59 (3) |
| Derivative of MCH(3-19) | D 1.20 (1), E 1.58 (1), P 1.12 (1), G 2.07 (1), V 1.60 (2), C n.d. (1), M 0.94 (2), L 2.0 (2), Y 0.19 (1), R 2.24 (3) |
| Derivative of MCH(4-19) | E 1.09 (1), P 1.46 (1), G 1.09 (1), V 1.83 (2), C n.d. (1), M 1.14 (2), L 2.0 (2), Y 0.27 (1), R 2.78 (3) |
| Derivative of MCH(5-19) | E 1.10 (1), P 0.90 (1), G 1.34 (1), V 1.55 (2), C n.d. (1), M 0.32 (1), L 2.0 (2), Y 0.32 (1), R 2.28 (3) |

Reference Example 6

Preparation of Radio-iodinated MCH, MCH (2-19), MCH (3-19), MCH (4-19), MCH (5-19), MCH (6-19) and MCH (7-19)

Isotope-labeled MCH, MCH (2-19), MCH (3-19), MCH (4-19), MCH (5-19), MCH (6-19) and MCH (7-19) can also be prepared by radio-iodination of Tyr$^{13}$ in the amino acid sequences, as follows. An example will be given below with respect to MCH (4-19), but MCH, MCH (2-19), MCH (3-19), MCH (5-19), MCH (6-19) and MCH (7-19) can also be radio-iodinated in a similar manner.

In 25 µl of 0.4 M sodium acetate (pH 5.6), 5 µg of MCH (4-19) was dissolved. After adding 200 ng of lacto-peroxidase (Wako Pure Chemical Industries, Ltd.) to the solution, 1 mCi of [$^{125}$I]-sodium iodide (Amersham Pharmacia Biotech, Inc.) and 200 ng of hydrogen peroxide (10 µl) were added to the mixture. The mixture was allowed to stand at room temperature for 10 minutes, and 200 ng of hydrogen peroxide (10 µl) was further added to the mixture, which was then kept still for 10 minutes. The mixture was purified by HPLC using TSKgel ODS-80Ts column (4.6 mm×25 cm, Toso) to give [$^{125}$I]-labeled MCH (4-19).

Reference Example 7

Preparation of MCH (Asp-Phe-Asp-Met-Leu-Arg-Cys-Met-Leu-Gly-Arg-Val-Tyr-Arg-Pro-Cys-Trp-Gln-V al)

Into a reaction vessel of a peptide synthesizer ABI 430A, 0.5 mmol of Boc-Val-OCH$_2$-PAM resin (0.77 mmol/g resin) commercially available was charged. Using the Boc-strategy (NP-HOBt) peptide synthesis method, Boc-Gln, Boc-Trp (CHO), Boc-Cys (MeBzl), Boc-Pro, Boc-Arg (Tos), Boc-Tyr (Br-Z), Boc-Val, Boc-Arg(Tos), Boc-Gly, Boc-Leu, Boc-Met, Boc-Cys (MeBzl), Boc-Arg (Tos), Boc-Leu, Boc-Met, Boc-Asp (OcHex), Boc-Phe and Boc-Asp (OcHex) were introduced in this order to give the objective peptide resin protected. After 0.6 g of this resin was stirred in 10 ml of anhydrous hydrogen fluoride together with 2 g of p-cresol and 1.2 ml of 1,4-butanedithiol at 0° C. for 60 minutes, the hydrogen fluoride was removed by distillation in vacuum. Diethyl ether was added to the residue, and the resulting precipitates were filtrated. Then, the precipitates were extracted with 50% aqueous acetic acid solution added thereto, and insoluble matters were removed. The extract was thoroughly concentrated, and then applied to Sephadex (trade name) G-25 column (2.0×80 cm) in 50% aqueous acetic acid. By development with the solvent, the major fractions were collected and then applied to a reversed phase chromatography column (2.6×60 cm) packed with LiChroprep (trade name) RP-18. After the column was washed with 200 ml of 0.1% TFA in water, linear gradient elution was performed using 300 ml of 0.1% TFA in water and 300 ml of 40% acetonitrile in water containing 0.1% TFA. The major fractions were collected and concentrated. The concentrate was dissolved in about 4 ml of acetic acid. After the solution was diluted to 240 ml with distilled water, the dilution was adjusted to pH 7.5 using ammonia water, and then gently stirred with pumping air. The reaction was monitored with HPLC. After it was confirmed that the peak of SH form-peptide is all changed to the SS-form, acetic acid was added to adjust pH of the solution to 3, and the mixture was applied to the LiChroprep (trade name) RP-18 column described above for adsorption. The column was washed with 200 ml of 0.1% TFA in water, and then linear gradient elution was performed using 300 ml of 0.1% TFA in water and 300 ml of 50% acetonitrile in water containing 0.1% TFA. The major fractions were pooled and lyophilized to give the objective peptide.

Mass spectrum (M+H)$^+$ 2387.3 (calcd. 2387.9) HPLC elution time: 20.9 mins. Column conditions: Column: Wakosil-II 5C18HG (4.6×150 mm) Eluent: Eluent A—0.1% TFA containing 10% acetonitrile in water, Eluent B—0.1% TFA containing 60% acetonitrile in water;linear gradient elution from A/B 20/80 to 80/20 (20 mins.) Flow rate: 1.0 ml/min.

Reference Example 8

Preparation of Des-Asp$^1$-MCH (MCH (2-19), Phe-Asp-Met-Leu-Arg-Cys-Met-Leu-Gly-Arg-Val-Tyr-Arg-Pro-Cys-Trp-Gln-Val)

Into a reaction vessel of peptide synthesizer ABI 430A, 0.5 mmol of Boc-Val-OCH$_2$-PAM resin (0.77 mmol/g resin) commercially available was charged. Using the Boc-strategy (NMP-HOBt) peptide synthesis method, Boc-Gln, Boc-Trp (CHO), Boc-Cys (MeBzl), Boc-Pro, Boc-Arg (Tos), Boc-Tyr (Br-Z), Boc-Val, Boc-Arg(Tos), Boc-Gly, Boc-Leu, Boc-Met, Boc-Cys (MeBzl), Boc-Arg (Tos), Boc-Leu, Boc-Met, Boc-Asp (OcHex) and Boc-Phe were introduced in this order to give the objective protected peptide resin. This resin was subjected to removal of the protective groups, cyclization and purification in a manner similar to REFERENCE EXAMPLE 7 to give the objective peptide.

Mass spectrum (M+H)$^+$ 2272.3 (calcd. 2272.1) HPLC elution time: 20.6 mins. Column conditions: Column: Wakosil-II 5C18HG (4.6×150 mm) Eluent: Eluent A—0.1% TFA containing 10% acetonitrile in water, Eluent B—0.1% TFA containing 60% acetonitrile in water; Linear gradient elution from A/B 20/80 to 80/20 (20 mins.) Flow rate: 1.0 m/min.

Reference Example 9

Preparation of Des-[Asp$^1$, Phe$^2$]-MCH (MCH (3-19), Asp-Met-Leu-Arg-Cys-Met-Leu-Gly-Arg-Val-Tyr-Arg-Pro-Cys-Trp-Gln-Val)

Into a reaction vessel of peptide synthesizer ABI 430A, 0.5 mmol of Boc-Val-OCH$_2$-PAM resin (0.77 mmol/g resin) commercially available was charged. Using the Boc-strategy (NMP-HOBt) peptide synthesis method, Boc-Gln, Boc-Trp (CHO), Boc-Cys (MeBzl), Boc-Pro, Boc-Arg (Tos), Boc-Tyr (Br-Z), Boc-Val, Boc-Arg(Tos), Boc-Gly, Boc-Leu, Boc-Met, Boc-Cys (MeBzl), Boc-Arg (Tos), Boc-Leu, Boc-Met and Boc-Asp (OcHex) were introduced in this order to give the objective peptide resin protected. This resin was subjected to removal of the protective groups, cyclization and purification in a manner similar to REFERENCE EXAMPLE 7 to give the objective peptide.

Mass spectrum (M+H)$^+$ 2124.8 (calcd. 2125.0) HPLC elution time: 19.2 mins. Column conditions: Column: Wakosil-II 5C18HG (4.6×150 mm) Eluent: Eluent A—0.1% TFA containing 10% acetonitrile in water, Eluent B—0.1% TFA containing 60% acetonitrile in water; Linear gradient elution from A/B 20/80 to 80/20 (20 mins.) Flow rate: 1.0 ml/min.

Reference Example 10

Preparation of Des-[Asp$^1$, Phe$^2$, Asp$^3$, Met$^4$]—MCH (MCH (5-19), Leu-Arg-Cys-Met-Leu-Gly-Arg-Val-Tyr-Arg-Pro-Cys-Trp-Gln-Val-OH)

Into a reaction vessel of peptide synthesizer ABI 430A, 0.5 mmol of Boc-Val-OCH$_2$-PAM resin (0.77 mmol/g resin) commercially available was charged. Using the Boc-strategy (NMP-HOBt) peptide synthesis method, Boc-Gln, Boc-Trp (CHO), Boc-Cys (MeBzl), Boc-Pro, Boc-Arg (Tos), Boc-Tyr (Br-Z), Boc-Val, Boc-Arg(Tos), Boc-Gly, Boc-Leu, Boc-Met, Boc-Cys (MeBzl), Boc-Arg (Tos) and Boc-Leu were introduced in this order to give the objective peptide resin protected. This resin was subjected to removal of the protective groups, cyclization and purification in a manner similar to REFERENCE EXAMPLE 7 to give the objective peptide.

Mass spectrum (M+H)$^+$ 1878.9 (calcd. 1878.9) HPLC elution time: 17.4 mins. Column conditions: Column: Wakosil-II 5C18HG (4.6×150 mm) Eluent: Eluent A—0.1% TFA containing 10% acetonitrile in water, Eluent B—0.1% TFA containing 60% acetonitrile in water; Linear gradient elution from A/B 20/80 to 80/20 (20 mins.) Flow rate: 1.0 ml/min.

Example 1

Amplification of cDNA of a Human Receptor SLT

Using as a template pCR3.1-hSLT described in REFERENCE EXAMPLE 1, amplification was performed by PCR using the synthetic DNA primers of SEQ ID NOS. 1 and 2. The synthetic DNA primers were constructed to amplify the gene in the region to be translated into the receptor protein. In this case, in order to add the base sequence recognized by restriction enzyme Sal I to the amplified gene at the 5' end and to add the base sequence recognized by restriction enzyme Spe I at the 3' end, the respective recognition sequences of these restriction enzymes were added at the 5'- and 3'-primers. The reaction solution was composed of 5 μl of pCR3.1-hSLT as a template, 0.4 μM each of the synthetic DNA primers, 0.2 mM dNTPs, 1 μl of pfu (Stratagene) DNA polymerase, and the buffer attached to the enzyme to make the total volume 50 μl. Using a Thermal Cycler (PE Biosystems), the amplification cycle was performed by heating at 94° C. for 60 seconds; and then 25 cycles of heating at 94° C. for 60 seconds, at 57° C. for 60 seconds and at 72° C. for 150 seconds; and finally heating at 72° C. for 10 minutes. The amplified products were confirmed by 0.8% agarose gel electrophoresis followed by ethidium bromide staining.

Example 2

Subcloning of the PCR Product into a Plasmid Vector and Confirmation of the Amplified cDNA Sequence by Determining the Base Sequence of the Inserted cDNA Part The reaction product obtained by PCR in EXAMPLE 1 was separated using 0.8% low melting agarose gel, and the banded part was excised from the gel with a razor blade and minced, followed by extraction with phenol and with phenol-chloroform. The extract was precipitated in ethanol to recover the DNA. According to the protocol attached to PCR-Script™ Amp SK (+) Cloning Kit (Stratagene), the recovered DNA was subcloned into the plasmid vector, PCR-Script Amp SK (+). The vector was introduced into Escherichia coli DH5α competent cells (Toyobo) to produce a transformant. The transformed clones having a cDNA-inserted fragment were then selected in an LB agar culture medium containing ampicillin, IPTG and X-gal. Only transformant clones exhibiting white color were picked with a sterilized toothstick to give the transformant E. coli DH5α/hSLT. The individual clones were cultured overnight in an LB culture medium containing ampicillin, and plasmid DNA was prepared using QIAwell 8 Plasmid Kit (Qiagen). An aliquot of the DNA thus prepared was cleaved with restriction enzymes Sal I and Spe I to confirm the size of the receptor cDNA fragment inserted. The reaction for determining base sequence was carried out using a DyeDeoxy Terminator Cycle Sequencing Kit (PE Biosystems), and the DNAs were decoded by a fluorescent automatic sequencer. It was confirmed by sequence analysis of the 2 clones thus obtained that all the sequences (SEQ ID NO:4) are consistent to the gene sequence, in which the Sal I recognition sequence was added to the 5' end and the Spe I recognition sequence was added to the 3' end of the cDNA sequence encoding human protein SLT (SEQ ID NO:3) as already reported. The amino acid sequence of human receptor protein SLT and the DNA sequence encoding the same are shown in FIG. 1.

Example 3

Preparation of Human SLT-expressing CHO Cells

By using Plasmid Midi Kit (Qiagen), a plasmid was prepared from E. coli clone transformed by the plasmid containing the gene encoding the full-length amino acid sequence of human SLT, the sequence of which was confirmed in EXAMPLE 2, and bearing the Sal I and Spe I recognition sequences added at the 5' and 3' ends of the gene, respectively. The plasmid was cleaved with restriction enzymes Sal I and Spe I to excise the inserted part. After electrophoresis, the inserted DNA was excised from the agarose gel with a razor blade and minced, followed by extraction with phenol and with phenol-chloroform. The extract was precipitated in ethanol for recovery. The inserted DNA was ligated to the vector plasmid pAKKO-111H (the same plasmid as pAKKO1.11 H described in Hinuma, S. et al., Biochim. Biophys. Acta, vol. 1219, pp. 251-259 (1994)) for expression in an animal cell, cleaved with Sal I and Spe I, using T4 ligase (Takara Shuzo Co., Ltd.). Plasmid pAKKO-hSLT for protein expression was thus constructed.

After incubation of E. coli DH5a competent cells (Toyobo) transformed by pAKKO-hSLT, the plasmid DNA of pAKKO-hSLT was prepared from the cells using Plasmid Midi Kit (Qiagen). Using CellPhect Transfection Kit (Amersham Pharmacia Biotech), the plasmid DNA was introduced into CHO dhfr⁻ cells according to the protocol attached. A suspension of 6 μg of DNA co-precipitated with calcium phosphate was prepared and added to a 6 cm Petri dish, on which $5 \times 10^5$ or $1 \times 10^6$ of CHO dhfr⁻ cells had been inoculated 24 hours before the addition. After incubation for a day in MEMα medium containing 10% cow fetal serum, the cells were subcultured in a selection medium or nucleic acid-free MEMA medium containing 10% dialyzed cow fetal serum. From the transformant colonies of human SLT-expressing CHO cells grown in the selection medium, 46 clones were selected.

Example 4

Selection of CHO/hSLT Cell Clone Having a High Expression Level of the Full-length Human Receptor Protein SLT mRNA The expression level of the full-length human SLT receptor protein mRNA in 46 clones of CHO/hSLT cell established in EXAMPLE 3 was determined by the following procedure, using Cytostar T Plate (Amersham Pharmacia Biotech), according to the protocol attached. These CHO/hSLT cell clones were inoculated on each well of Cytostar T plate, respectively, at $2.5 \times 10^4$ cells/well, and incubated for 24 hours. The cells were then fixed in 10% formalin. To each well, 0.25% Triton X-100 was added to enhance permeability of the cells, and $^{35}$S-labeled riboprobe of SEQ ID NO:5 was added thereto for hybridization. After 20 mg/ml of RNase A was added to each well to digest free riboprobe, the plate was thoroughly washed and the radioactivity of hybridized riboprobe was measured with a Topcounter. The clone showing a higher radioactivity has a higher expression level of mRNA. In the following experiments, 6 clones (#1, 3, 4, 13, 26 and 36) having a higher mRNA expression level were employed, especially clone #1 being mainly used.

Example 5

Activity of MCH to Inhibit cAMP Production in Human SLT-expressing CHO Cells

Commercially available synthetic human MCH (SEQ ID NO:6, Bachem Ltd.) was diluted at various concentrations and the inhibition of cAMP production in human SLT-expressing CHO cells was determined by the following procedure. The CHO/hSLT cells selected in EXAMPLE 4 were inoculated on a 24-well plate at $5 \times 10^4$ cells/well, and incubated for 48 hours. The cells were washed with HANKS' buffer (pH 7.4) containing 0.2 mM 3-isobutylmethylxanthine, 0.05% BSA and 20 mM HEPES (hereinafter HANKS' buffer (pH 7.4) containing 0.2 mM 3-isobutylmethylxanthine, 0.05% BSA and 20 mM HEPES is referred to as a reaction buffer). Thereafter, 0.5 ml of the reaction buffer was added to the cells and the mixture was kept warm in an incubator for 30 minutes. After the reaction buffer was removed, 0.25 ml of the reaction buffer was newly added to the cells, and then 0.25 ml of the reaction buffer containing MCH in various amounts and 2 μM forskolin was added to the cells. The reaction was performed at 37° C. for 30 minutes. The reaction was terminated by adding 100 μl of 20% perchloric acid. The reaction mixture was then put on ice for an hour to extract the intracellular cAMP. The amount of cAMP in the extract was measured using cAMP EIA Kit (Amersham Pharmacia Biotech). The results reveal that MCH clearly decreased the intracellular cAMP at the concentration of 30 pM, and as the peptide concentration increased, the amount of intracellular cAMP decreased in a dose-dependent manner (FIG. 2). In this figure, the activity of inhibiting cAMP production was expressed in terms of percentage for the amount obtained by subtracting the intracellular cAMP amount when the reaction buffer was added, from the intracellular cAMP amount when MCH was added, taking as 100% the amount obtained by subtracting the intracellular cAMP amount when the reaction buffer was added, from the intracellular cAMP amount when the reaction buffer containing forskolin was added.

Example 6

Preparation of Cell Membrane Fraction of Human SLT-expressing CHO Cell

After 10 ml of a homogenate buffer (10 mM $NaHCO_3$, 5 mM EDTA, 0.5 mM PMSF, 1 µg/ml pepstatin, 4 µg/ml E64 and 20 µg/ml leupeptin) was added to $1 \times 10^8$ CHO/hSLT cells, the cells was homogenized by using Polytron (12,000 rpm, 1 min.). The cell homogenate was centrifuged (1,000 g, 15 mins.) to give a supernatant. Next, the supernatant was subjected to ultracentrifugation (Beckman type 30 rotor, 30,000 rpm, 1 hour). The resulting precipitate was used as a cell membrane fraction of human SLT-expressing CHO cell.

Example 7

Receptor Binding Assay with [$^{125}$I]-labeled MCH (4-19) Prepared Using Bolton-Hunter Reagent Receptor binding assay was performed using [$^{125}$I]-labeled MCH (4-19) prepared in REFERENCE EXAMPLE 3 using Bolton-Hunter reagent and the cell membrane fraction prepared from human SLT-expressing CHO cells.

Figure 3:
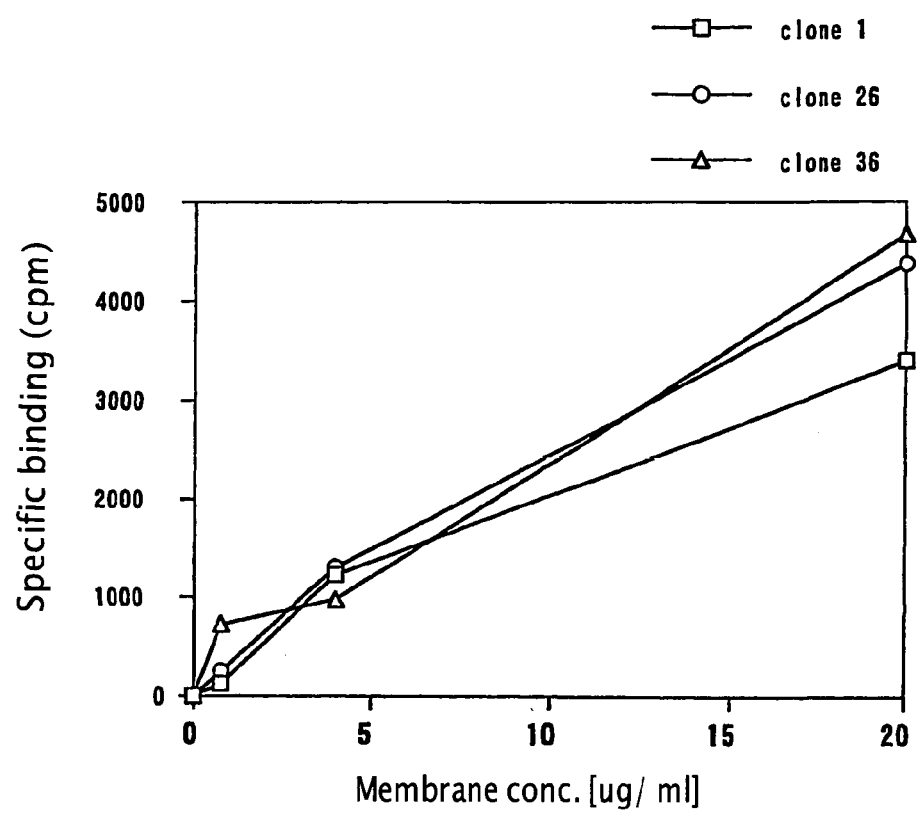
FIG. 3 shows the specific binding of [$^{125}$I]-labeled MCH (4-19), which is prepared using Bolton-Hunter reagent, to cell membrane fractions, which are prepared from CHO cells expressing human SLT. The membrane fractions are prepared from 3 different expression cell clones (#1, 26, 36) and used for the measurement.

The cell membrane fraction prepared from human SLT-expressing CHO cells according to EXAMPLE 6 was diluted at various concentrations with the assay buffer (50 mM Tris-HCl, 5 mM EGTA (ethyleneglycol-bis(aminoethylether) tetraacetic acid), 5 mM magnesium acetate, 0.05% CHAPS, 0.1% BSA (bovine serum albumin), 0.25 mM PMSF (phenylmethylsulfonyl fluoride), 1 µg/ml pepstatin, 20 µg/ml leupeptin, pH 7.4). A 200 µl aliquot of each dilution was then dispensed in a polypropylene testing tube (Falcon, Inc., 2053). Two µl of DMSO and 2 µl of 20 nM [$^{125}$I]-labeled MCH (4-19) were added to the membrane fraction solution to determine the amount of total binding (TB), and 2 µl of a solution of 100 µM MCH in DMSO and 2 µl of 20 µM [$^{125}$I]-labeled MCH (4-19) were added thereto to determine the amount of non-specific binding (NSB). After reaction at 25° C. for 60 minutes, the reaction solution was filtered with suction through a polyethyleneimine-treated glass filter (Whatman Co., GF-F). Following the filtration, the radioactivity of [$^{125}$I]-labeled MCH (4-19) remaining on the filter paper was measured with a γ-counter. As shown in FIG. 3, the specific binding of [$^{125}$I]-labeled MCH (4-19) dependent on the concentration of membrane fraction was observed.

Figure 4:
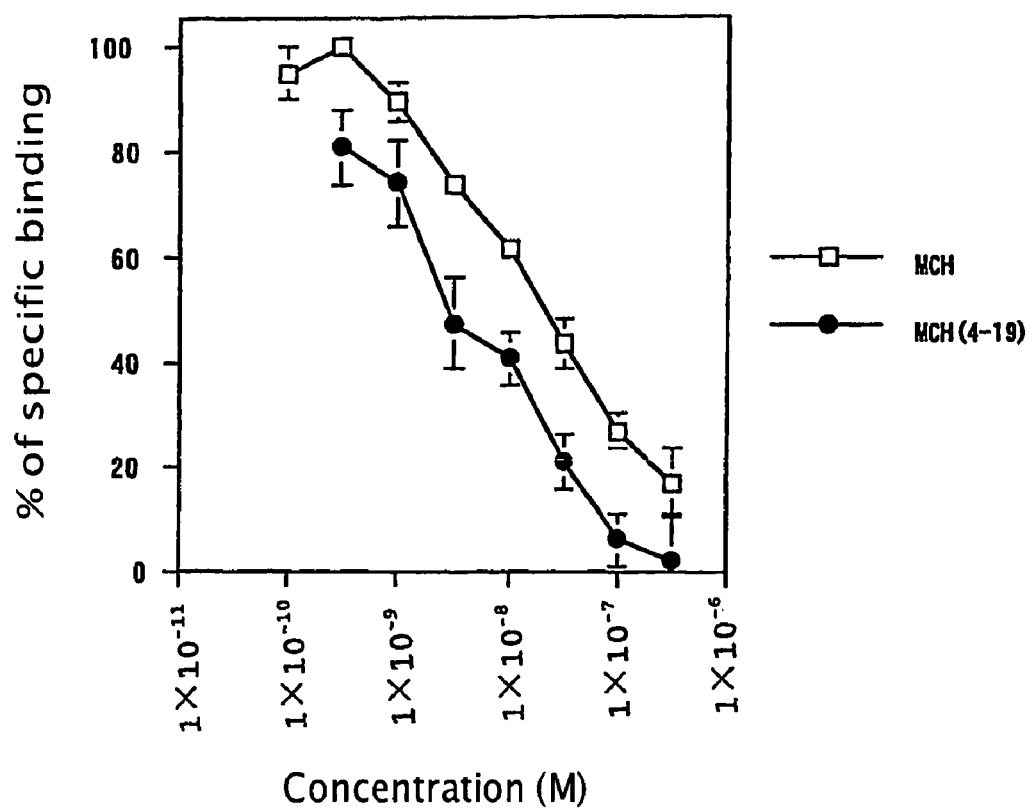
FIG. 4 shows the inhibitory effect of MCH and MCH (4-19), an N-terminal truncated form thereof on the specific binding of [$^{125}$I]-labeled MCH (4-19), which is prepared using Bolton-Hunter reagent, to a cell membrane fraction, which is prepared from CHO cells expressing human SLT.

Also, the concentration of membrane fraction was set at 30 µg/ml, and 50% inhibitory concentration ($IC_{50}$) of MCH was calculated from the inhibition rate (%). As a result, the $IC_{50}$ value was approximately 20 nM (FIG. 4). The $IC_{50}$ value of MCH (4-19), namely, an amino terminal-truncated form of MCH was 3.3 nM (FIG. 4).

Example 8

Figure 5:
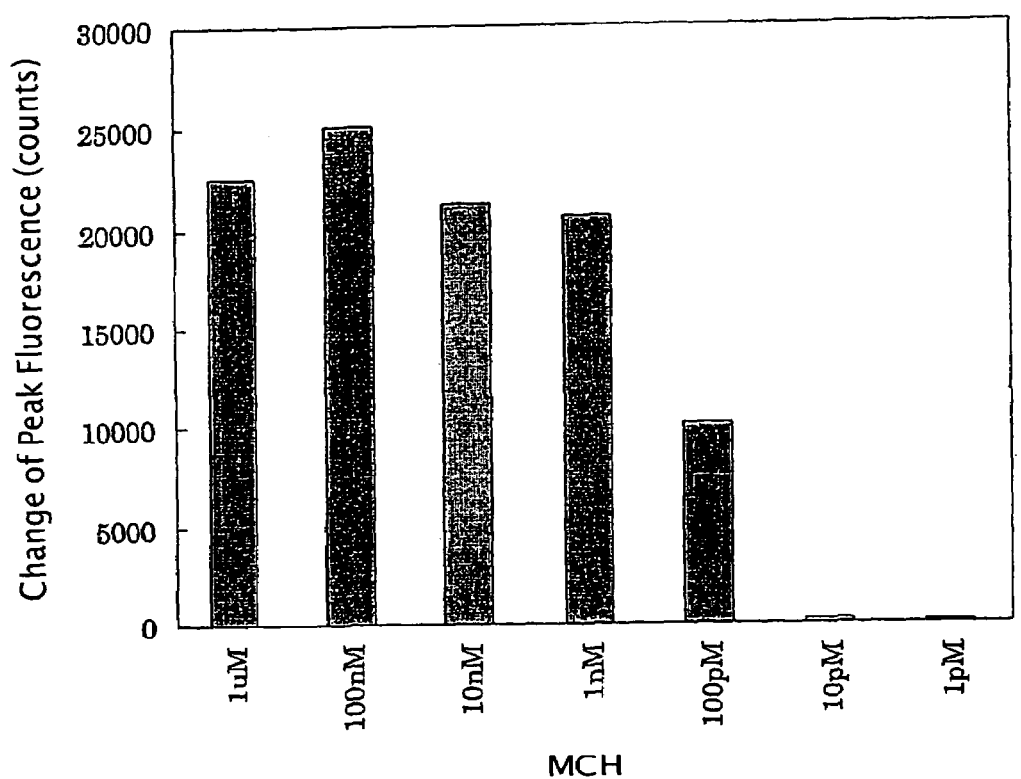
FIG. 5 shows the activity of MCH at various concentrations to increase the intracellular Ca ions in CHO cells expressing human SLT, which is measured with FLIPR.

Assay Using FLIPR for the Activity of MCH to Increase the Intracellular Ca ion Level in Human SLT-expressing CHO Cells Using FLIPR (Molecular Device), the MCH-induced increase in intracellular Ca ion level in human SLT-expressing CHO cells was assayed. CHO/hSLT cells were suspended in DMEM containing 10% dialyzed cow fetal serum at $15 \times 10^4$ cells/ml, and plated on each well of a 96-well plate (Black plate clear bottom, Costar, Inc.) in 200 µl each ($3.0 \times 10^4$ cells/200 µl/well) using a dispenser. After incubation overnight at 37° C. under 5% $CO_2$, the plate was used for assay (hereinafter this plate is referred to as a cell plate). To a mixture of 20 ml of HANKS'/HBSS (9.8 g of Nissui HANKS 2 (Nissui Seiyaku K. K.), 0.35 g of sodium hydrogen carbonate, 4.77 g of HEPES; adjusted to pH7.4 with 6M sodium hydroxide solution, and sterilized through filter), 200 µl of 250 mM probenecid and 200 µl of fetal bovine serum (FBS), added was a solution of 2 vials (50 µg) of Fluo 3-AM (Dojin Kagaku Kenkyusho) in 40 µl of dimethylsulfoxide and 40 µl of 20% Pluronic acid (Molecular Probe, Inc.). After the culture medium was removed from the cell plate, 100 µl of the mixed solution was dispensed to each well using an 8-channel pipette. By incubation at 37° C. for an hour in a 5% $CO_2$ incubator, the dye was loaded into the cells. To each well of another 96-well plate for FLIPR (V-Bottom plate, Coster, Inc.), 150 µl of HANKS'/HBSS containing 2.5 mM Probenecid and 0.05% BSA was added and MCH was further added thereto at various concentrations to prepare a sample plate. After completion of dye-loading in the cell plate, the cell plate was washed 4 times using a plate washer with wash buffer containing 2.5 mM Probenecid in HANKS'/HBSS, finally to leave 100 µl of wash buffer after the washing. The cell plate and the sample plate were set in FLIPR for assay (50 µl of each sample from the sample plate was transferred to the cell plate in FLIPR). The results show that MCH increases the intracellular Ca ion level in human SLT-expressing CHO cells in a manner dependent on the concentration (FIG. 5).

Example 9

Figure 6:
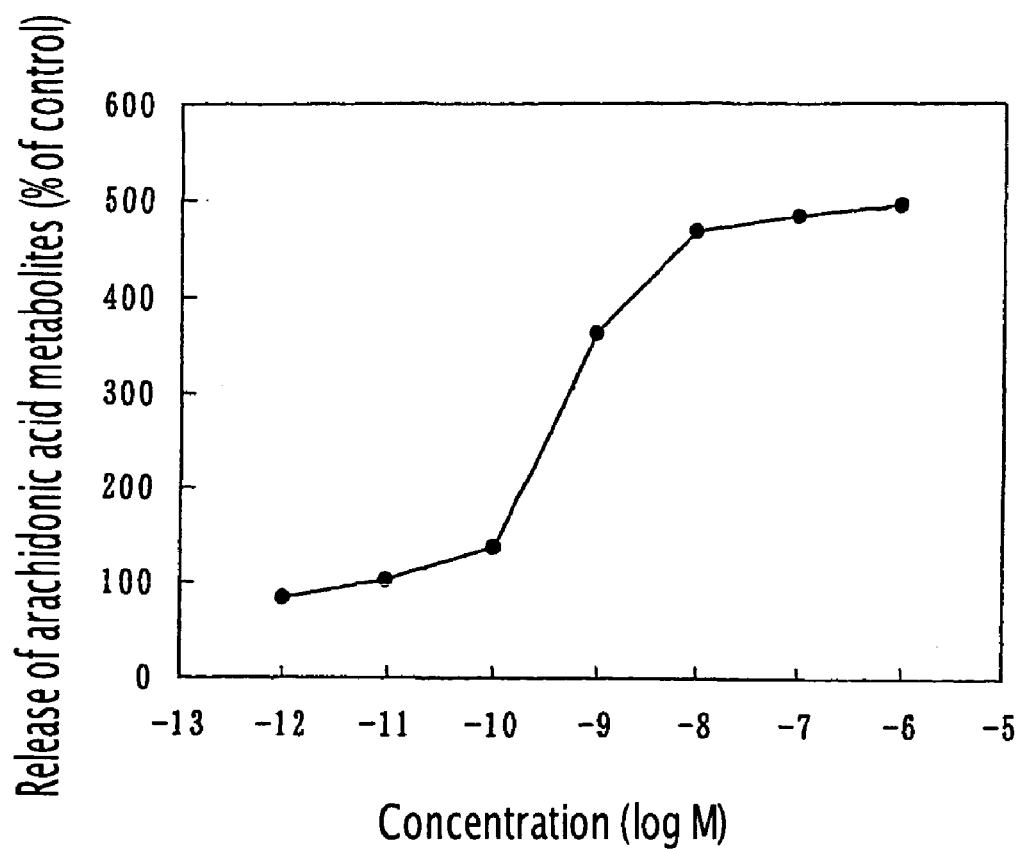
FIG. 6 shows the activity of MCH at various concentrations to release metabolites of arachidonic acid in CHO cells expressing human SLT.

Activity of MCH to Induce the Release of Arachidonic Acid Metabolite in Human SLT-expressing CHO Cells The release of arachidonic acid metabolite induced by MCH at various concentrations in human SLT-expressing CHO cells was determined by the following procedure. The CHO/hSLT cells or human SLT-expressing CHO cells, acquired in EXAMPLE 4, were inoculated on a 24-well plate at $5 \times 10^4$ cells/well. After incubation for 24 hours, [$^3$H] arachidonic acid was added to each well at 0.25 µCi/well. Sixteen hours after the addition of [$^3$H] arachidonic acid, the cells were washed with HANKS' buffer (pH 7.4) containing 0.05% BSA and 20 mM HEPES. Then, to each well added was 500 µl of HANKS' buffer (pH 7.4) containing 0.05% BSA and 20 mM HEPES, together with MCH at various concentrations. Following incubation at 37° C. for 60 minutes, 400 µl of the reaction solution was taken and added to a scintillator and the amount of [$^3$H] arachidonic acid metabolites released into the reaction solution was measured using a scintillation counter. The results reveal that MCH has the activity to induce the release of the arachidonic acid metabolite in human SLT-expressing cells in a does-dependent manner, and that the $EC_{50}$ value was 0.57 nM. The activity of MCH to induce the release of arachidonic acid metabolite at various concentrations in human SLT-expressing CHO cells is shown in FIG. 6.

DESCRIPTION FOR THE SEQUENCE LISTING

SEQ ID NO: 6
Other information regarding the sequence: Two Cys residues at the 7th position and the 16th position form an intramolecular disulfide bond.

SEQ ID NO: 10
Other information regarding the sequence: Two Cys residues at the 6th position and the 15th position form an intramolecular disulfide bond.

SEQ ID NO: 11
Other information regarding the sequence: Two Cys residues at the 5th position and the 14th position form an intramolecular disulfide bond.

SEQ ID NO: 12
Other information regarding the sequence: Two Cys residues at the 4th position and the 13th position form an intramolecular disulfide bond.

SEQ ID NO: 13
Other information regarding the sequence: Two Cys residues at the 3rd position and the 12th position form an intramolecular disulfide bond.

SEQ ID NO: 14
Other information regarding the sequence: Two Cys residues at the 2nd position and the 11th position form an intramolecular disulfide bond.

SEQ ID NO: 15
Other information regarding the sequence: Two Cys residues at the 1st position and the 10th position form an intramolecular disulfide bond.

INDUSTRIAL APPLICABILITY

The method of the present invention for screening a compound or a salt thereof that alters the binding property of MCH, a derivative or a salt thereof to SLT or a salt thereof comprises using MCH, a derivative or a salt thereof and SLT or a salt thereof. The method is useful for screening an SLT agonist, which can be used as an agent for promoting appetite (eating), and further as a prophylactic and/or therapeutic agent for weak uterine contraction, atonic bleeding, delivery of placenta, uterine involution insufficiency, Caesarean operation, artificial abortion, lactic retention, and the like; and the method is useful for screening an SLT antagonist, which can be used as a prophylactic and/or therapeutic agent for obesity (e.g. malignant mastocytosis, exogenous obesity, hyperinsulinar obesity, hyperplasmic obesity, hypophyseal obesity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), hyperphagia, emotional disorder, sexual dysfunction, and further for too strong uterine contraction, tonic uterine contraction, fetal asphyxia, uterine rupture, endocervical canal laceration, premature delivery, Prader-Willi syndrome, and the like.

The invention claimed is:

1. A method for screening a compound or a salt thereof that alters the binding property of Melanin Concentrating Hormone (MCH) or a salt thereof to a protein having the amino acid sequence of SEQ ID NO: 3, an amide, an ester or a salt thereof, said method comprising:

combining a MCH derivative or a salt thereof, a protein having the amino acid sequence of SEQ ID NO: 3, an amide, an ester or a salt thereof, and a test compound in an assay;

determining the amount of MCH derivative or a salt thereof that binds to a protein having the amino acid sequence of SEQ ID NO: 3 in the presence of said compound or in the absence of said compound; and comparing the amount of binding in the presence of said compound with the amount of binding in the absence of said compound;

wherein said MCH derivative is a peptide comprising an amino acid sequence selected from the group consisting of:

the $2^{nd}$ residue through the $19^{th}$ residue, the $3^{rd}$ residue through the $19^{th}$ residue, the $4^{th}$ residue through the $19^{th}$ residue, the $5^{th}$ residue through the $19^{th}$ residue, the $6^{th}$ residue through the $19^{th}$ residue, and the $7^{th}$ residue through the $19^{th}$ residue of the amino acid sequence of SEQ ID NO: 6, an amide or an ester thereof, with the proviso that said MCH derivative is not a peptide comprising the $1^{st}$ residue through the $19^{th}$ residue of the amino acid sequence of SEQ ID NO: 6.

2. The screening method of claim 1, wherein said Melanin Concentrating Hormone (MCH) is a peptide comprising the amino acid sequence of SEQ ID NO: 6.

3. The screening method of claim 1, wherein said Melanin Concentrating Hormone (MCH) derivative is a peptide comprising the $5^{th}$ residue through the $19^{th}$ residue of the amino acid sequence of SEQ ID NO: 6, an amide or an ester thereof.

4. The screening method of claim 1, wherein said Melanin Concentrating Hormone (MCH) derivative is prepared using Bolton-Hunter reagent.

5. The screening method of claim 1, wherein said Melanin Concentrating Hormone (MCH) derivative or salt thereof is

[$^{125}$I]-[N-(3-(4-hydroxy-3-iodophenyl)propionyl)-Phe$^2$]-MCH(2-19),

[$^{125}$I]-[N-(3-(4-hydroxy-3-iodophenyl)propionyl)-Asp$^3$]-MCH(3-19),

[$^{125}$I]-[N-(3-(4-hydroxy-3-iodophenyl)propionyl)-Met$^4$]-MCH(4-19),

[$^{125}$I]-[N-(3-(4-hydroxy-3-iodophenyl)propionyl)-Leu$^5$]-MCH(5-19),

[$^{125}$I]-[N-(3-(4-hydroxy-3-iodophenyl)propionyl)-Arg$^6$]-MCH(6-19),

[$^{125}$I]-[N-(3-(4-hydroxy-3-iodophenyl)propionyl)-Asp$^7$]-MCH(7-19), or a salt thereof.

6. The screening method of claim 1, wherein said Melanin Concentrating Hormone (MCH) derivative is [$^{12}$I]-[N-(3-(4-hydroxy-3-iodophenyl)propionyl)-Met$^4$]-MCH(4-19).

7. A kit for screening a compound or a salt thereof that alters the binding property of Melanin Concentrating Hormone (MCH) or a salt thereof to a protein having the amino acid sequence of SEQ ID NO: 3, an amide, an ester or a salt thereof, where said kit comprises;
  a Melanin Concentrating Hormone (MCH) derivative or a salt thereof, wherein said MCH derivative is a peptide comprising an amino acid sequence selected from the group consisting of:
  the $2^{nd}$ residue through the $19^{th}$ residue, the $3^{rd}$ residue through the $19^{th}$ residue, the $4^{th}$ residue through the $19^{th}$ residue, the $5^{th}$ residue through the $19^{th}$ residue, the $6^{th}$ residue through the $19^{th}$ residue, and the $7^{th}$ residue through the $19^{th}$ residue of the amino acid sequence of SEQ ID NO: 6, an amide or an ester thereof,
  with the proviso that said MCH derivative is not a peptide comprising the $1^{st}$ residue through the $19^{th}$ residue of the amino acid sequence of SEQ ID NO: 6;
  and a protein having the amino acid sequence of SEQ ID NO: 3, an amide, an ester or a salt thereof.

8. The screening kit described in claim 7, which further comprises a polypeptide comprising the amino acid sequence of SEQ ID NO: 16 or 17 an amide, an ester or a salt thereof.

9. The screening kit of claim 7, wherein said Melanin Concentrating Hormone (MCH) is a peptide comprising the amino acid sequence of SEQ ID NO: 6.

10. The screening kit of claim 7, wherein said Melanin Concentrating Hormone (MCH) derivative is a peptide comprising the $5^{th}$ residue through the $19^{th}$ residue of the amino acid sequence of SEQ ID NO: 6, an amide or an ester thereof.

11. The screening kit of claim 7, wherein said Melanin Concentrating Hormone (MCH) derivative is prepared using Bolton-Hunter reagent.

12. The screening kit of claim 7, wherein said Melanin Concentrating Hormone (MCH) derivative or salt thereof is
  [$^{125}$I]-[N-(3-(4-hydroxy-3-iodophenyl)propionyl)-Phe$^2$]-MCH(2-19),
  [$^{125}$I]-[N-(3-(4-hydroxy-3-iodophenyl)propionyl)-Asp$^3$]-MCH(3-19),
  [$^{125}$I]-[N-(3-(4-hydroxy-3-iodophenyl)propionyl)-Met$^4$]-MCH(4-19),
  [$^{125}$I]-[N-(3-(4-hydroxy-3-iodophenyl)propionyl)-Leu$^5$]-MCH(5-19),
  [$^{125}$I]-[N-(3-(4-hydroxy-3-iodophenyl)propionyl)-Arg$^6$]-MCH(6-19),
  [$^{125}$I]-[N-(3-(4-hydroxy-3-iodophenyl)propionyl)-Asp$^7$]-MCH(7-19), or a salt thereof.

13. The screening kit of claim 7, wherein said Melanin Concentrating Hormone (MCH) derivative is [$^{125}$I]-[N-(3-(4-hydroxy-3-iodophenyl)propionyl)-Met$^4$]-MCH(4-19).

14. A method for screening a compound or a salt thereof that alters the binding property of Melanin Concentrating Hormone (MCH) or a salt thereof, to a polypeptide comprising the amino acid sequence of SEQ ID NO: 16 or 17, an amide, an ester or a salt thereof or a protein having the amino acid sequence of SEQ ID NO: 3, an amide, ester or salt thereof, for any preferential agonist or antagonist effect on the binding of Melanin Concentrating Hormone (MCH) to a polypeptide comprising the amino acid sequence of SEQ ID NO: 16 or 17, or a protein having the amino acid sequence of SEQ ID NO: 3, said method comprising:
  (i) combining a Melanin Concentrating Hormone (MCH) derivative or a salt thereof, a polypeptide comprising the amino acid sequence of SEQ ID NO: 16 or 17, an amide, ester or a salt thereof, and a test compound in an assay;
  (ii) combining a Melanin Concentrating Hormone (MCH) derivative or a salt thereof, a protein having the amino acid sequence of SEQ ID NO: 3, an amide, ester or salt thereof, and a test compound in an assay;
  (iii) determining the amount of a Melanin Concentrating Hormone (MCH) derivative that binds to a polypeptide comprising the amino acid sequence of SEQ ID NO: 16 or 17 in the presence of said compound as compared with in the absence of said compound;
  (iv) determining the amount of a Melanin Concentrating Hormone (MCH) derivative that binds to a protein having the amino acid sequence of SEQ ID NO: 3 in the presence of said compound as compared with in the absence of said compound; and
  (v) comparing the amount of binding between (iii) and (iv);
wherein said Melanin Concentrating Hormone (MCH) derivative is a peptide comprising an amino acid sequence selected from the group consisting of:
  the $2^{nd}$ residue through the $19^{th}$ residue, the $3^{rd}$ residue through the $19^{th}$ residue, the $4^{th}$ residue through the $19^{th}$ residue, the $5^{th}$ residue through the $19^{th}$ residue, the $6^{th}$ residue through the $19^{th}$ residue, and the $7^{th}$ residue through the $19^{th}$ residue of the amino acid sequence of SEQ ID NO: 6,
  an amide, an ester or a salt thereof,
    with the proviso that said MCH derivative is not a peptide comprising the $1^{st}$ residue through the $19^{th}$ residue of the amino acid sequence of SEQ ID NO: 6.

* * * * *